(12) United States Patent
Roberts et al.

(10) Patent No.: US 11,285,169 B2
(45) Date of Patent: Mar. 29, 2022

(54) METHODS FOR MODULATING CHEMOTHERAPEUTIC CYTOTOXICITY

(71) Applicant: The United States of America, as represented by the Secretary, Dept. of Health and Human Services, Bethesda, MD (US)

(72) Inventors: David D. Roberts, Bethesda, MD (US); David R. Soto Pantoja, Rockville, MD (US)

(73) Assignee: The United States of America, as represented by the Secretary, Department of Health and Human Services, Bethesda, MD (US)

( * ) Notice: Subject to any disclaimer, the term of this patent is extended or adjusted under 35 U.S.C. 154(b) by 137 days.

(21) Appl. No.: 14/775,428

(22) PCT Filed: Mar. 13, 2014

(86) PCT No.: PCT/US2014/025989
§ 371 (c)(1),
(2) Date: Sep. 11, 2015

(87) PCT Pub. No.: WO2014/160183
PCT Pub. Date: Oct. 2, 2014

(65) Prior Publication Data
US 2016/0045532 A1 Feb. 18, 2016

Related U.S. Application Data

(60) Provisional application No. 61/779,587, filed on Mar. 13, 2013.

(51) Int. Cl.
*A61K 31/713* (2006.01)
*A61K 31/704* (2006.01)
(Continued)

(52) U.S. Cl.
CPC .......... *A61K 31/713* (2013.01); *A61K 31/137* (2013.01); *A61K 31/351* (2013.01);
(Continued)

(58) Field of Classification Search
CPC ........................ C07K 16/2803; A61K 31/713; A61K 31/137; A61K 31/437; A61K 31/52;
(Continued)

(56) References Cited

U.S. PATENT DOCUMENTS 6,121,236 A * 9/2000 Ben-Sasson ......... C07K 14/515
530/324
6,235,716 B1 * 5/2001 Ben-Sasson ......... C07K 14/515
424/185.1
(Continued)

FOREIGN PATENT DOCUMENTS

WO  WO 2008/060785  5/2008
WO  WO 2010/017332  2/2010
(Continued)

OTHER PUBLICATIONS (R) Ramanathan et al., "Thrombospondin-1 and Angiotensin II inhibit Soluble Guanylyl Cyclases through an Increase in Intracellular Calciuim Concentration," Biochemistry, 50(36), 7787-7799 (2011).*
(Continued)

*Primary Examiner* — Eric Olson
(74) *Attorney, Agent, or Firm* — Klarquist Sparkman, LLP

(57) ABSTRACT

Methods of reducing cytotoxicity of a chemotherapeutic agent to non-cancer cells by administering to a subject with cancer an effective amount of an agent that inhibits CD47 signaling and a DNA damaging agent, such as an anthracycline, topoisomerase inhibitor, or nucleotide synthesis inhibitor, are provided. Example disclosed methods reduce
(Continued)

cardiotoxicity. In one example, the methods include administering to a subject with cancer an effective amount of a CD47 antisense morpholino oligonucleotide and an anthracycline such as doxorubicin. Methods of increasing cytotoxicity of a chemotherapeutic agent in cancer cells by administering to a subject with a tumor an effective amount of an agent that inhibits CD47 signaling and a DNA damaging agent such as an anthracycline, topoisomerase inhibitor, or nucleotide synthesis inhibitor, are also provided. In some embodiments, the inhibitor of CD47 signaling is administered to the subject before, during, or after the administration of the DNA damaging agent.

13 Claims, 26 Drawing Sheets

Specification includes a Sequence Listing.

(51) Int. Cl.

| A61K 31/437 | (2006.01) |
| A61P 39/00 | (2006.01) |
| A61K 31/351 | (2006.01) |
| A61P 35/00 | (2006.01) |
| A61K 31/52 | (2006.01) |
| A61K 31/137 | (2006.01) |
| A61K 31/365 | (2006.01) |
| A61K 31/65 | (2006.01) |
| A61K 31/706 | (2006.01) |
| A61K 39/395 | (2006.01) |
| A61K 31/711 | (2006.01) |
| A61K 31/7064 | (2006.01) |
| A61K 31/505 | (2006.01) |
| A61K 31/712 | (2006.01) |
| C07K 16/28 | (2006.01) |
| A61K 31/787 | (2006.01) |
| A61K 31/513 | (2006.01) |
| A61K 45/06 | (2006.01) |

(52) U.S. Cl.
CPC .......... *A61K 31/365* (2013.01); *A61K 31/437* (2013.01); *A61K 31/505* (2013.01); *A61K 31/513* (2013.01); *A61K 31/52* (2013.01); *A61K 31/65* (2013.01); *A61K 31/704* (2013.01); *A61K 31/706* (2013.01); *A61K 31/7064* (2013.01); *A61K 31/711* (2013.01); *A61K 31/712* (2013.01); *A61K 31/787* (2013.01); *A61K 39/39558* (2013.01); *A61K 45/06* (2013.01); *A61P 35/00* (2018.01); *A61P 39/00* (2018.01); *C07K 16/2803* (2013.01)

(58) Field of Classification Search
CPC .............. A61K 31/704; A61K 31/7064; A61K 31/712; A61K 31/505; A61K 31/65; A61K 31/706; A61K 31/365; A61K 31/711; A61K 39/39558; A61K 31/513; A61K 45/06; A61K 2300/00
See application file for complete search history.

(56) References Cited

U.S. PATENT DOCUMENTS

| 7,083,789 | B2* | 8/2006 | Ramakrishna | C07K 14/47 424/185.1 |
| 7,435,589 | B2* | 10/2008 | Mack | C07K 14/47 435/252.3 |
| 7,514,229 | B2* | 4/2009 | Jamieson | C12Q 1/6883 435/373 |
| 7,601,358 | B2* | 10/2009 | Fox | C12N 9/0083 424/184.1 |
| 7,655,411 | B2* | 2/2010 | Williams | C07K 14/78 435/4 |
| 7,919,467 | B2* | 4/2011 | Ramakrishna | A61K 38/19 514/19.3 |
| 8,014,957 | B2* | 9/2011 | Radich | C12Q 1/6886 702/19 |
| 8,044,178 | B2* | 10/2011 | Boghaert | A61K 47/6849 530/387.1 |
| 8,236,313 | B2* | 8/2012 | Isenberg | C07K 14/78 424/144.1 |
| 8,557,788 | B2* | 10/2013 | Isenberg | C07K 14/78 514/44 A |
| 8,609,383 | B2* | 12/2013 | Young | C07K 19/00 435/163 |
| 8,613,922 | B2* | 12/2013 | Clemmons | C07K 16/2896 424/139.1 |
| 8,617,561 | B2* | 12/2013 | Mevorach | C07K 14/78 424/184.1 |
| 8,691,780 | B2* | 4/2014 | Lih | C07K 14/4747 514/337 |
| 8,759,495 | B2* | 6/2014 | Boghaert | A61K 47/6849 530/388.85 |
| 8,865,672 | B2* | 10/2014 | Isenberg | C07K 14/78 424/184.1 |
| 8,951,527 | B2* | 2/2015 | Isenberg | A61K 38/39 424/172.1 |
| 9,109,022 | B2* | 8/2015 | Young | C07K 19/00 |
| 9,198,949 | B2* | 12/2015 | Susin | C07K 14/78 |
| 2006/0188508 | A1 | 8/2006 | Cohen et al. | |
| 2006/0241067 | A1 | 10/2006 | Varner et al. | |
| 2007/0041981 | A1 | 2/2007 | Howard et al. | |
| 2007/0154931 | A1 | 7/2007 | Radich et al. | |
| 2007/0209082 | A1 | 9/2007 | Lih et al. | |
| 2007/0231333 | A1 | 10/2007 | Boghaert et al. | |
| 2009/0191202 | A1 | 7/2009 | Jamieson et al. | |
| 2010/0092467 | A1 | 4/2010 | Isenberg et al. | |
| 2010/0215640 | A1 | 8/2010 | Clemmons et al. | |
| 2011/0014119 | A1* | 1/2011 | Jaiswal | A61P 35/00 424/1.49 |
| 2011/0135641 | A1 | 6/2011 | Isenberg et al. | |
| 2011/0206696 | A1* | 8/2011 | Frazier | A61P 35/00 424/172.1 |
| 2015/0111768 | A1* | 4/2015 | Roberts | C12N 5/0696 506/9 |

FOREIGN PATENT DOCUMENTS

| WO | WO 2011/034969 | 3/2011 |
| WO | WO 2011/076781 | 6/2011 |
| WO | WO 2011/143624 A2 | 11/2011 |
| WO | WO 2012/170250 A1 | 12/2012 |
| WO | WO 2014/012479 | 1/2014 |

OTHER PUBLICATIONS (S) Soto-Pantoja et al., "CD47 Deficiency Confers Cell and Tissue Radioprotection by Activation of Autophagy," Autophagy, 8(11), 1628-1642 (Nov. 2012).*
Tripathi, Essentials of Medical Pharmacology, Seventh Edition, Chapter 62 ("Anticancer Drugs," in part), Jaypee Bros. Medical Publisher, Ltd., Philadelphia, PA, 2013, pp. 858-869.*
Sick et al., "CD47 update: a multifaceted actor in the tumour microenvironment of potential therapeutic interest" British Journal of Pharmacology vol. 167 pp. 1415-1430 (Year: 2012).*
Cheung et al., "Abstract 3453: CD47 is a novel therapeutic target for hepatocellular carcinoma" Cancer Research vol. 71 issue 8 supplement, Proceedings of the 102nd Annual Meeting of the American Association for Cancer Research, DOI:10.1158/1538-7445. AM2011-2453 (Year: 2011).*
Soto-Pantoja et al., "Radioprotection in Normal Tissue and Delayed Tumor Growth by Blockade of CD47 signaling" Journal of Immunotherapy vol. 32 No. 9 p. 992 (Year: 2009).*

(56) References Cited

OTHER PUBLICATIONS

Isenberg et al., "Increasing Survival of Ischemic Tissue by Targeting CD47" Circulation Research vol. 100 pp. 712-720 DOI: 10.1161/01.RES.0000259579.35787.4e (Year: 2007).*

Hatzis et al., "A Genomic Predictor of Response and Survival Following Taxane-Anthracycline Chemotherapy for Invasive Breast Cancer" JAMA, May 11, 2011—vol. 305, No. 18 pp. 1873-1880 (Year: 2011).*

Barazi et al., "Regulation of Integrin Function by CD47 Ligands: Differential Effects on $\alpha_v\beta_3$ and $\alpha_4\beta_1$ Integrin-Mediated Adhesion," *J. Biol. Chem.*, vol. 277, No. 45, pp. 42859-42866, 2002.

Leclair et al., "CD47-Independent Effects Mediated by the TSP-Derived 4N1K Peptide," *PLoS One*, vol. 9, e98358, 2014 (8 pages).

Tulasne et al., "C-terminal peptide of thrombospondin-1 induces platelet aggregation through the Fc receptor γ-chain-associated signaling pathway and by agglutination," *Blood*, vol. 98, No. 12, pp. 3346-3352, 2001.

Ayla et al., "Doxorubicin Induced Nephrotoxicity: Protective Effect of Nicotinamide," *International Journal of Cell Biology*, vol. 2011, Article ID 390238, 2011 (9 pages).

Chao et al., "Anti-CD47 Antibody Synergizes with Rituximab to Promote Phagocytosis and Eradicate Non-Hodgkin Lymphoma," *Cell*, vol. 142, pp. 699-713, 2010.

Chao et al., "Therapeutic antibody targeting of CD47 eliminates human acute lymphoblastic leukemia," *Cancer Research*, vol. 71, No. 4, pp. 1374-1384, 2011.

Deng et al., "Differential roles of nitric oxide synthase isozymes in cardiotoxicity and mortality following chronic doxorubicin treatment in mice," *Naunyn-Schmied Arch Pharmacol*, vol. 380, pp. 25-34, 2009.

Franco et al., "Cardiovascular Effects in Childhood Cancer Survivors Treated with Anthracyclines," *Cardiology Research and Practice*, vol. 2011, Article ID 134679, 2011 (13 pages).

Herrmann et al., "Susceptibility of rhabdomyosarcoma cells to macrophage-mediated cytotoxicity," *OncoImmunology*, vol. 1, No. 3, pp. 279-286, 2012.

Huelsenbeck et al., "Inhibition of Rac1 signaling by lovastatin protects against anthracycline-induced cardiac toxicity," *Cell Death and Disease*, vol. 2, e190, 2011 (10 pages).

Isenberg et al., "Thrombospondin-1 is a Central Regulator of Nitric Oxide Signaling in Vascular Physiology," *Cell Mol. Life Sci.*, vol. 65, No. 5, pp. 728-742, 2008 (NIH Public Access version, 23 pages).

Majeti et al., "CD47 is an adverse prognostic factor and therapeutic antibody target on human acute myeloid leukemia stem cells," *Cell*, vol. 138, No. 2, pp. 286-299, 2010 (NIH Public Access Version, 24 pages).

Manna et al., "CD47 Mediates Killing of Breast Tumor Cells via Gi-Dependent Inhibition of Protein Kinase A," *Cancer Research*, vol. 64, pp. 1026-1036, 2004.

Maxhimer et al., "Radioprotection in Normal Tissue and Delayed Tumor Growth by Blockade of CD47 Signaling," *Science Translational Medicine*, vol. 1, No. 3, 3ra7, 2009 (11 pages).

Medline Accession No. NLM15818399, 1 page, 2005.

Rath et al., "The C-terminal CD47/IAP-binding domain of thrombospondin-1 prevents camptothecin- and doxorubicin-induced apoptosis in human thyroid carcinoma cells," *Biochimica et Biophysica Acta*, vol. 1763, pp. 1125-1134, 2006.

Sawyer et al., "Mechanisms of Anthracycline Cardiac Injury: Can we identify strategies for cardio-protection?" *Prog. Cardiovasc. Dis.*, vol. 53, No. 2, pp. 105-113, 2011 (NIH Public Access Version, 13 pages).

Soto-Pantoja et al., "Blockade of CD47 increases survival of mice exposed to lethal total body irradiation," *Scientific Reports*, vol. 3, 1038, 2013 (6 pages).

Soto-Pantoja et al., "CD47 deficiency confers cell and tissue radioprotection by activation of autophagy," *Autophagy*, vol. 8, No. 11, pp. 1628-1642, 2012.

Tsai et al., "Self inhibition of phagocytosis: the affinity of 'Marker of Self' CD47 for SIRPα dictates potency of inhibition but only at low expression levels," *Blood Cells Mol. Dis.*, vol. 45, No. 1, pp. 67-74, 2010 (NIH Public Access version, 17 pages).

Quesada et al., "In vivo upregulation of CD95 and CD95L causes synergistic inhibition of angiogenesis by TSP1 peptide and metronomic doxorubicin treatment," *Cell Death and Differentiation*, vol. 12, pp. 649-658, 2005.

Maxhimer et al., "Thrombospondin-1-CD47 Blockade Following Ischemia Reperfusion Injury is Tissue Protective," *Plast. Reconstr. Surg.* 124:1880-1889, 2009 (Author Manuscript version, 18 pages).

* cited by examiner

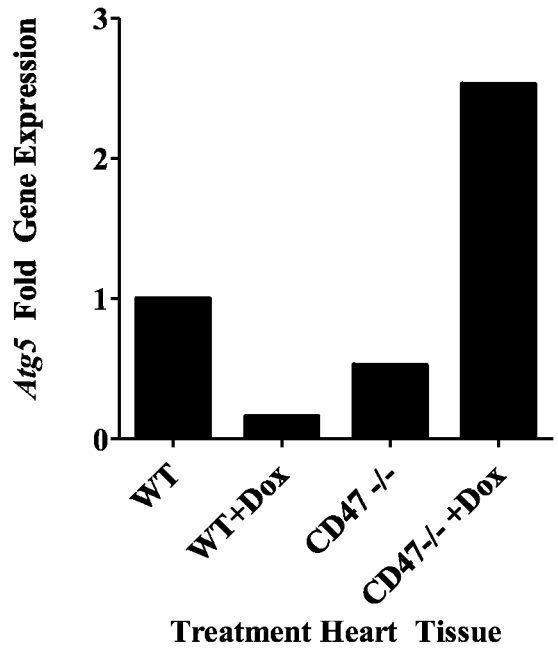
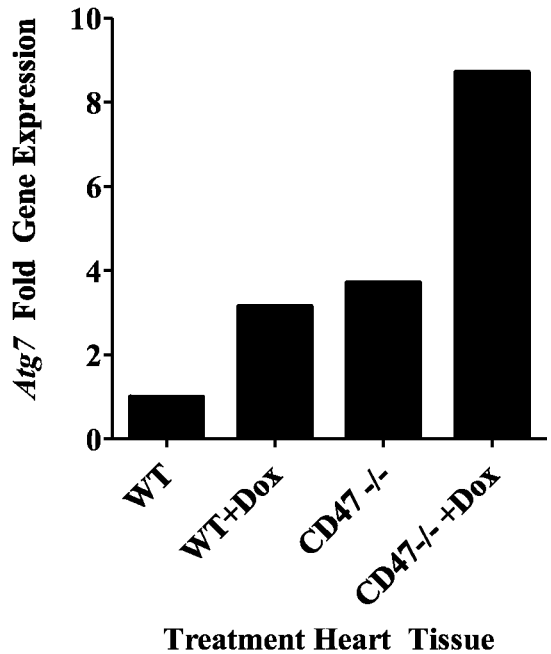
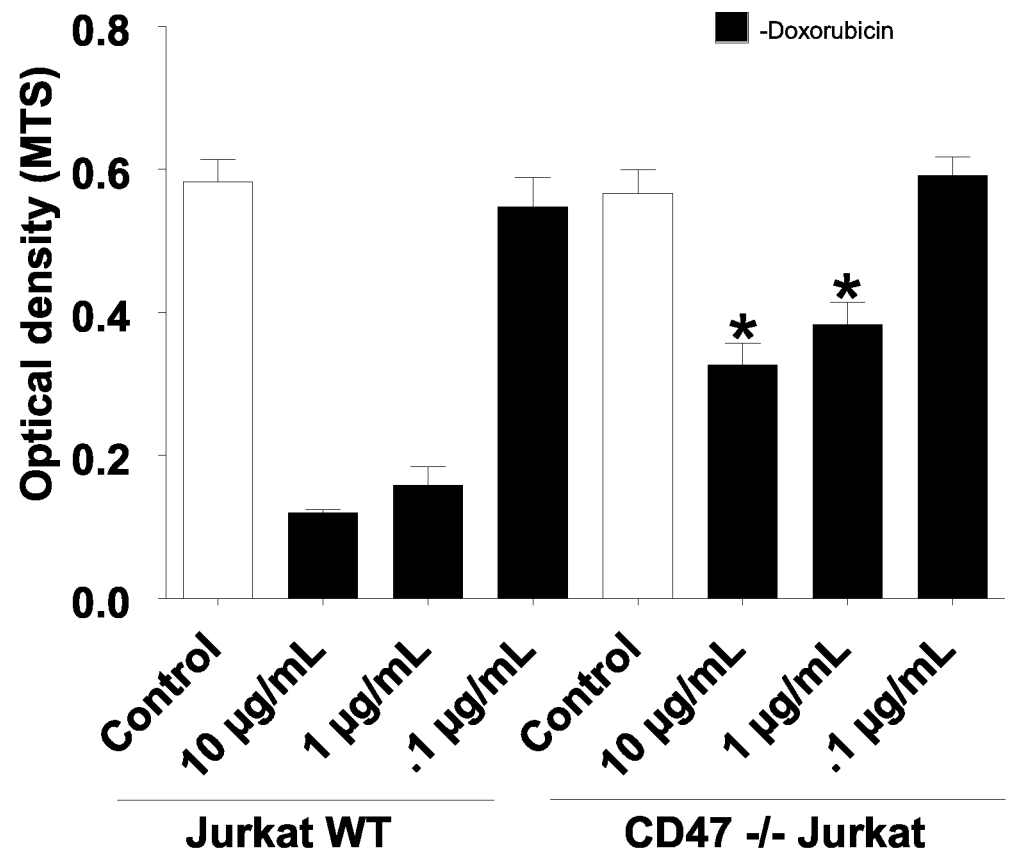

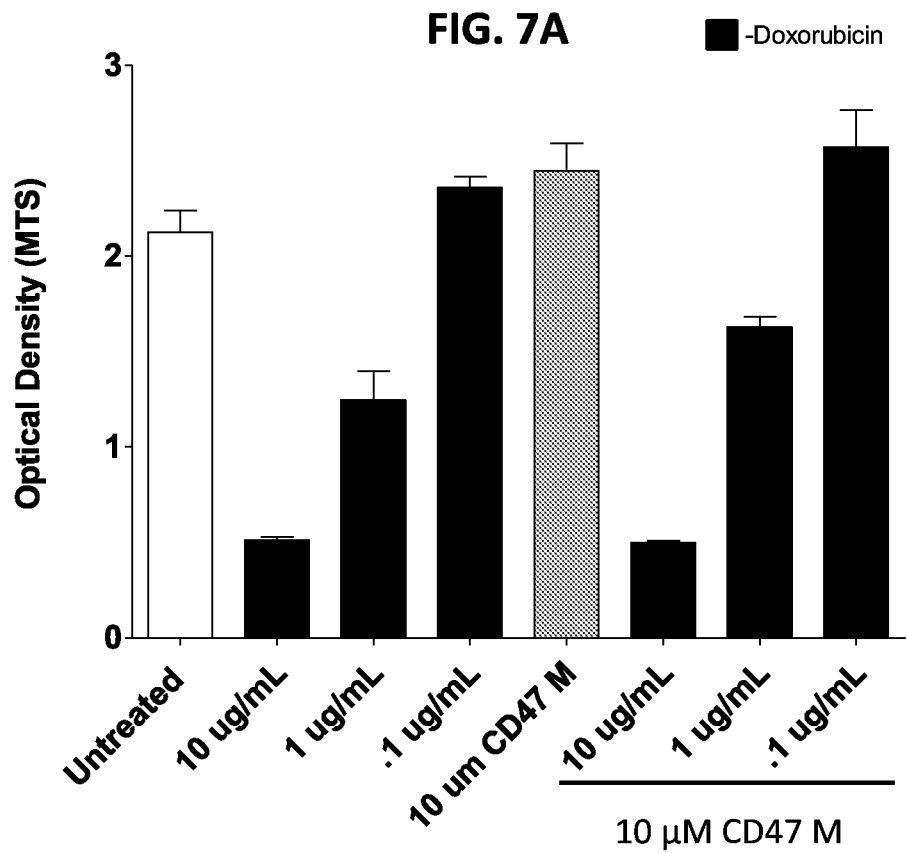
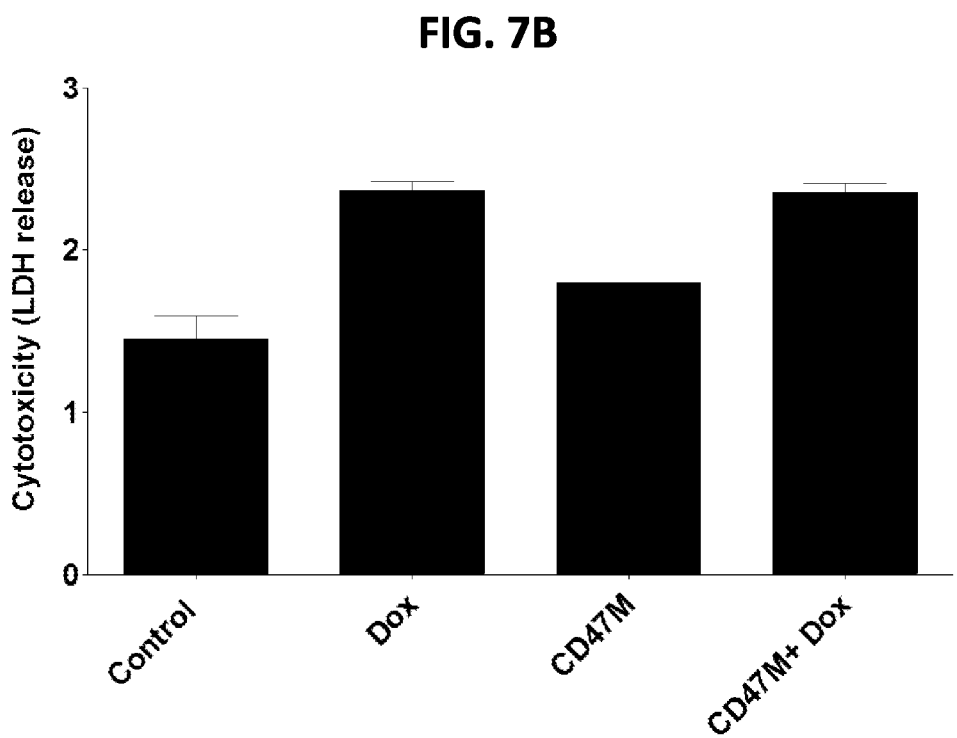

Saline          Dox+CD47M

FIG. 14A
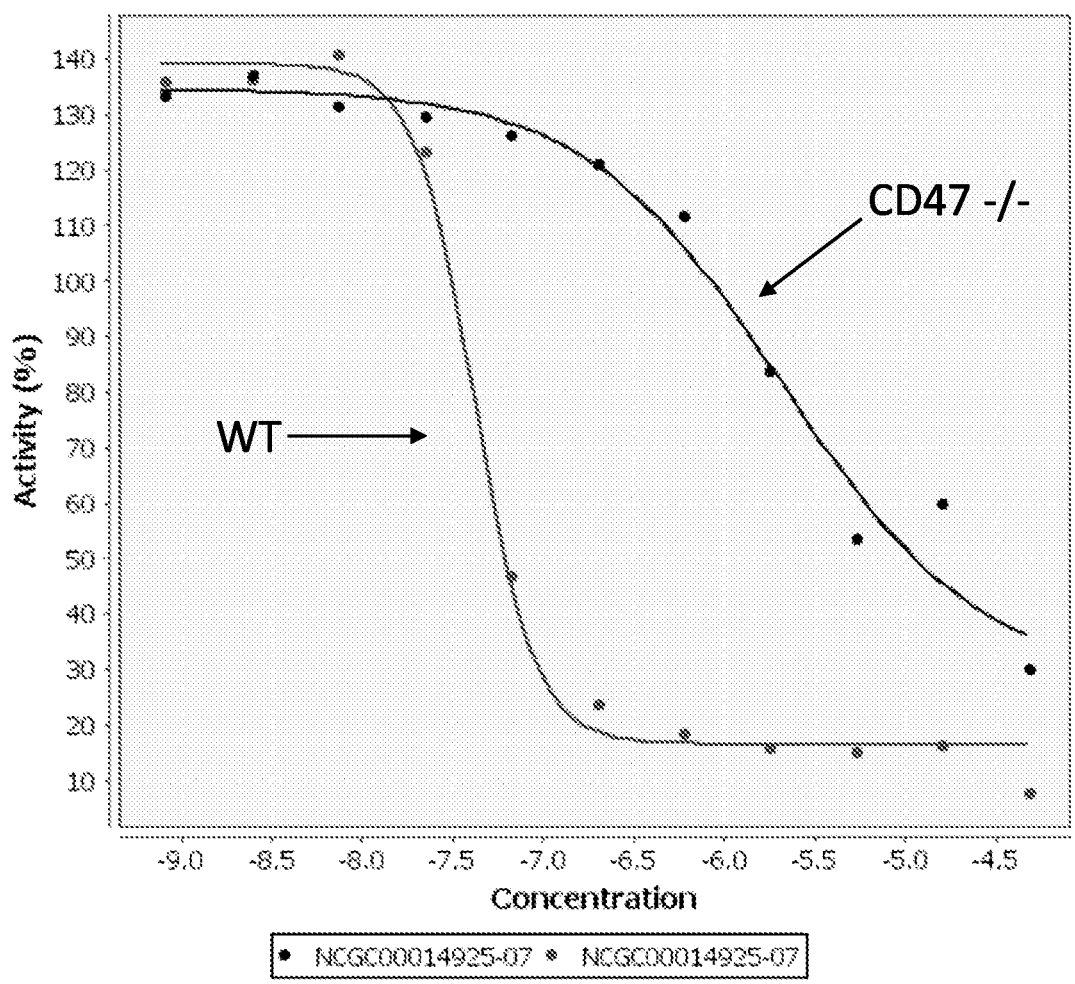
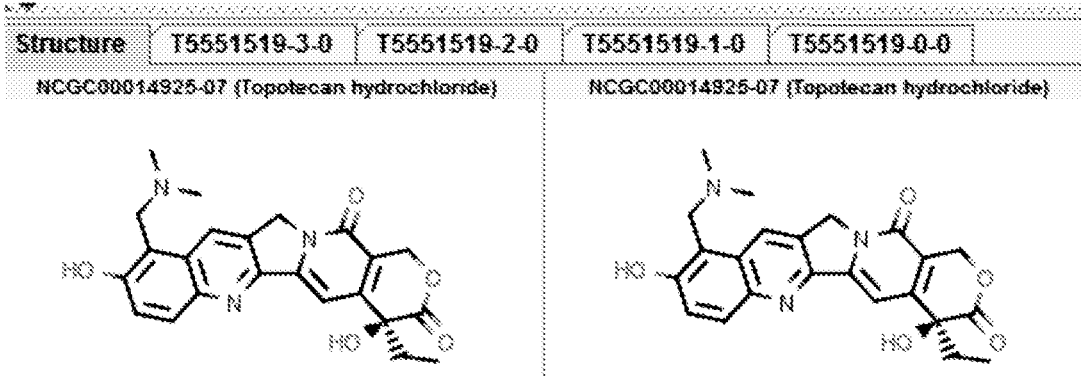

FIG. 14C
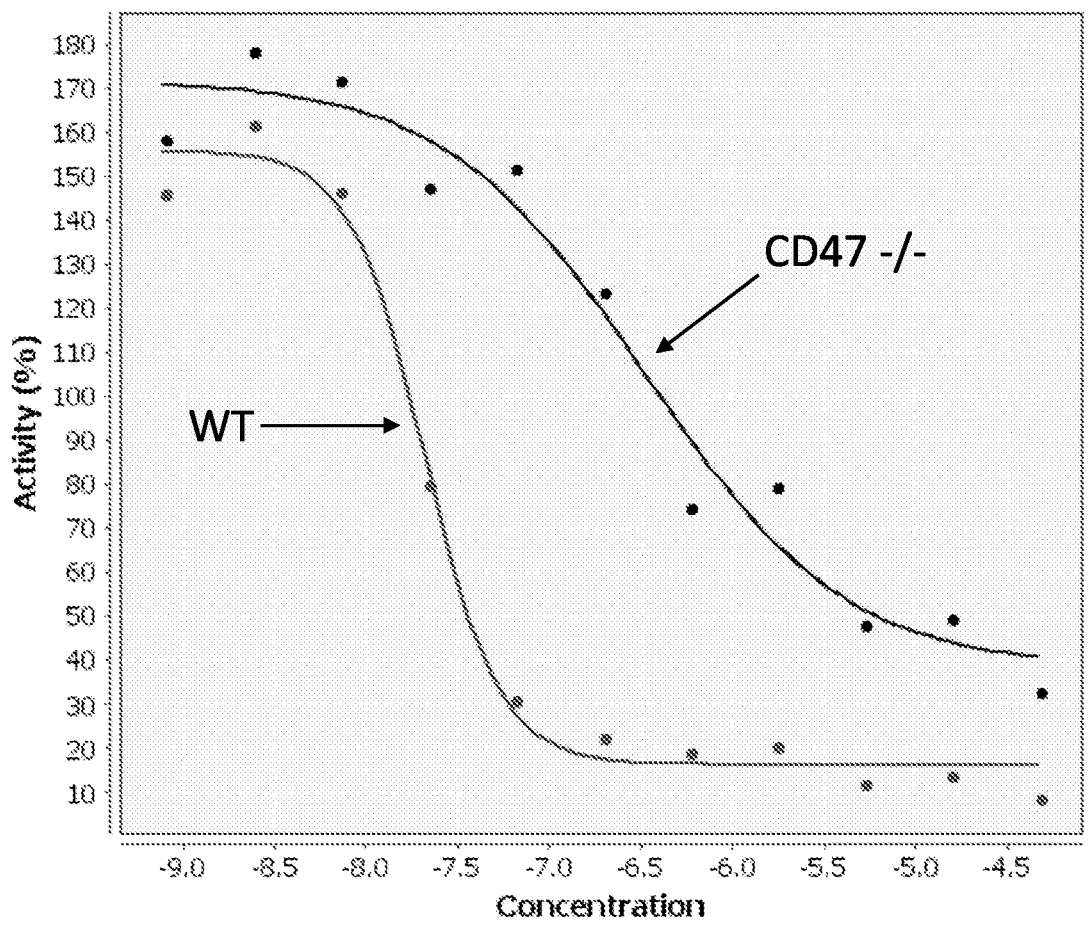
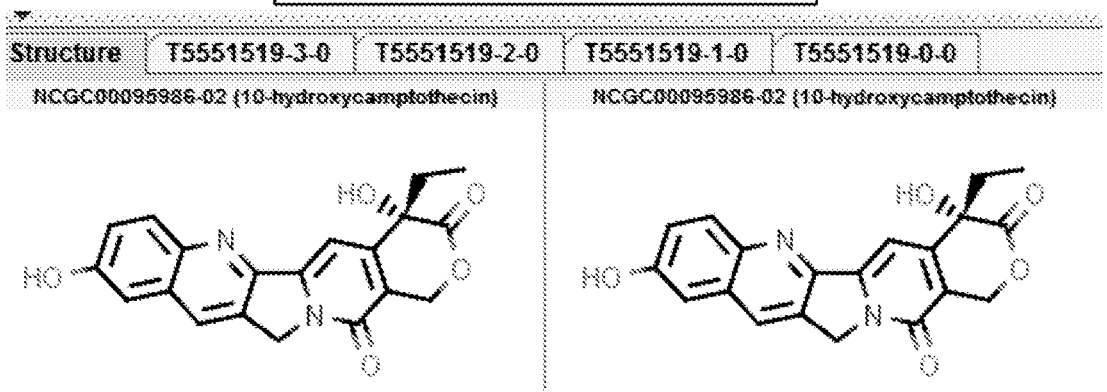

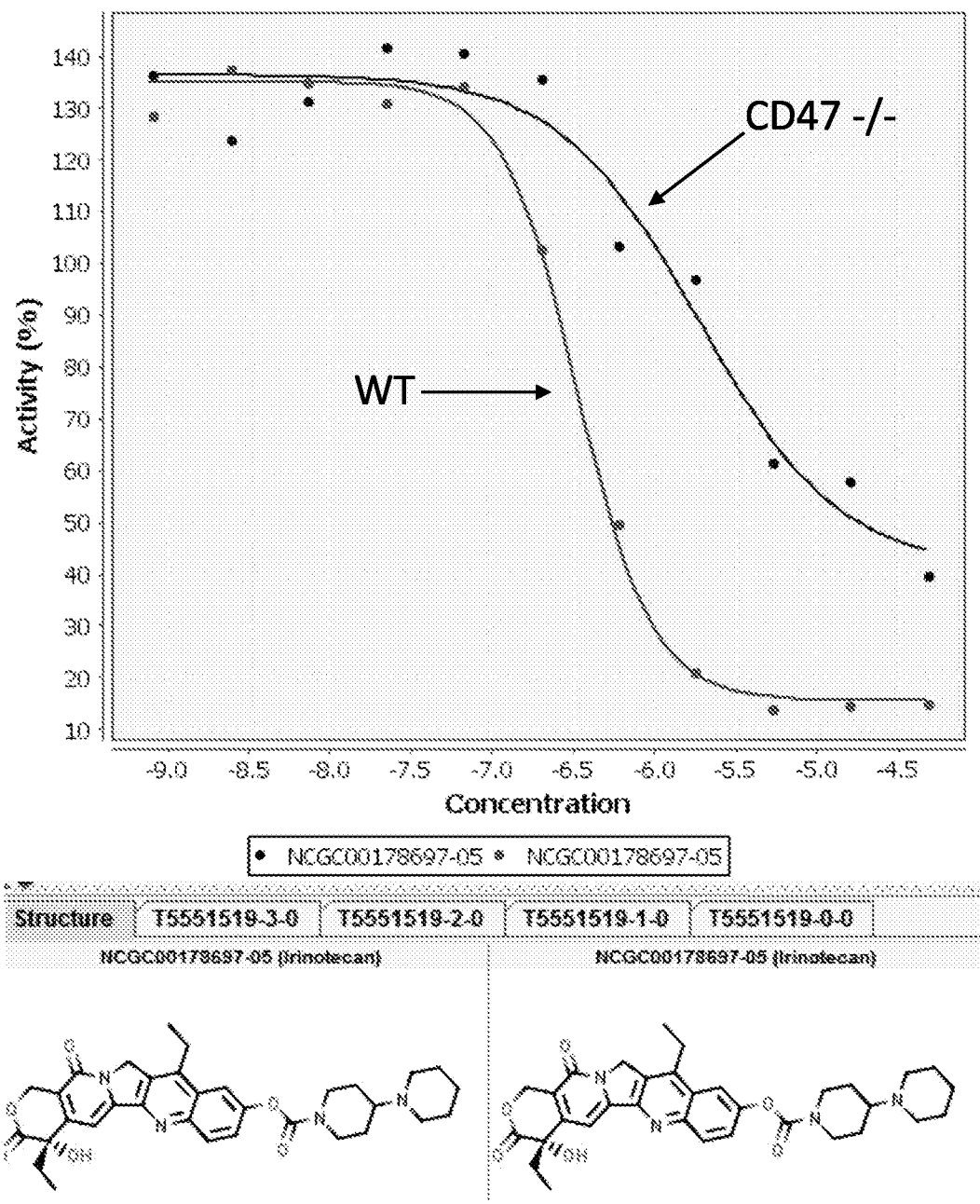

FIG. 15A
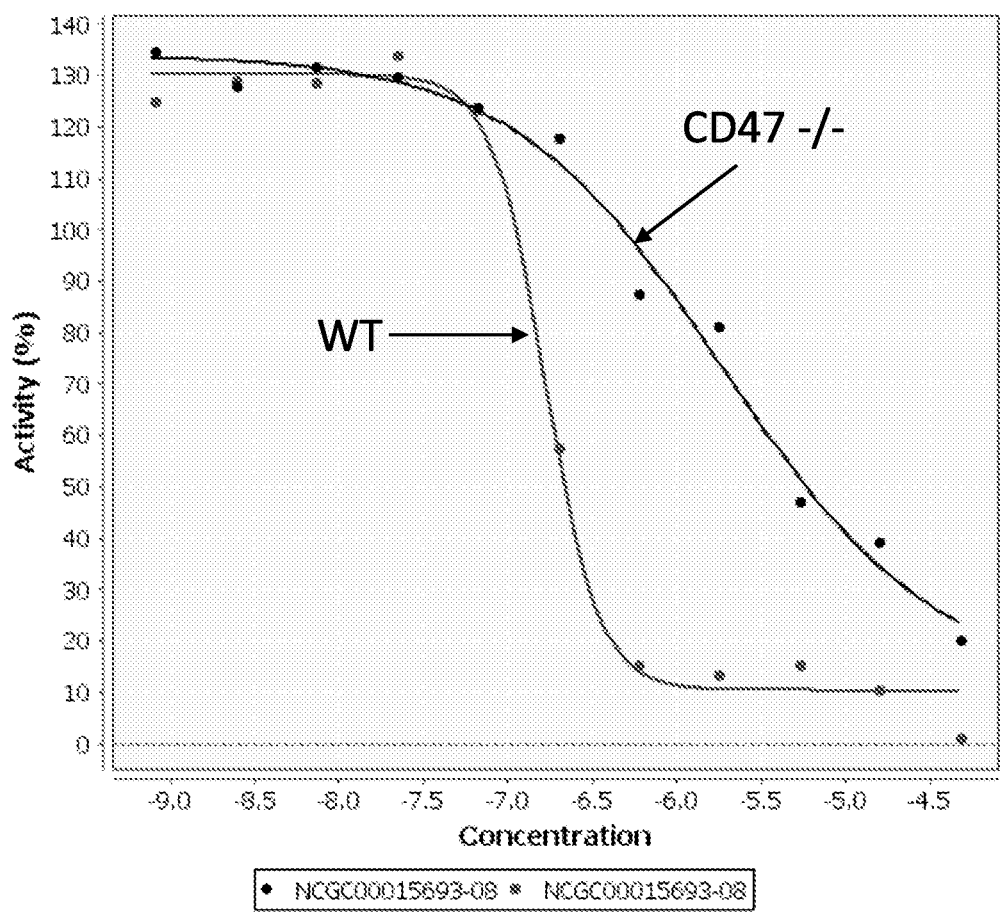
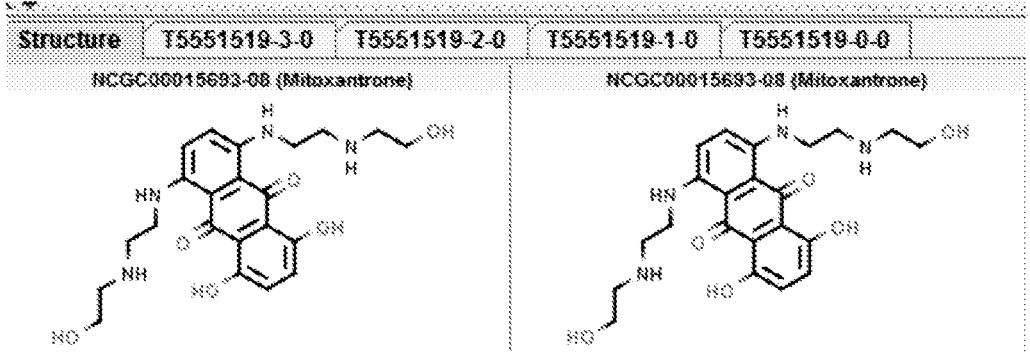

FIG. 15E
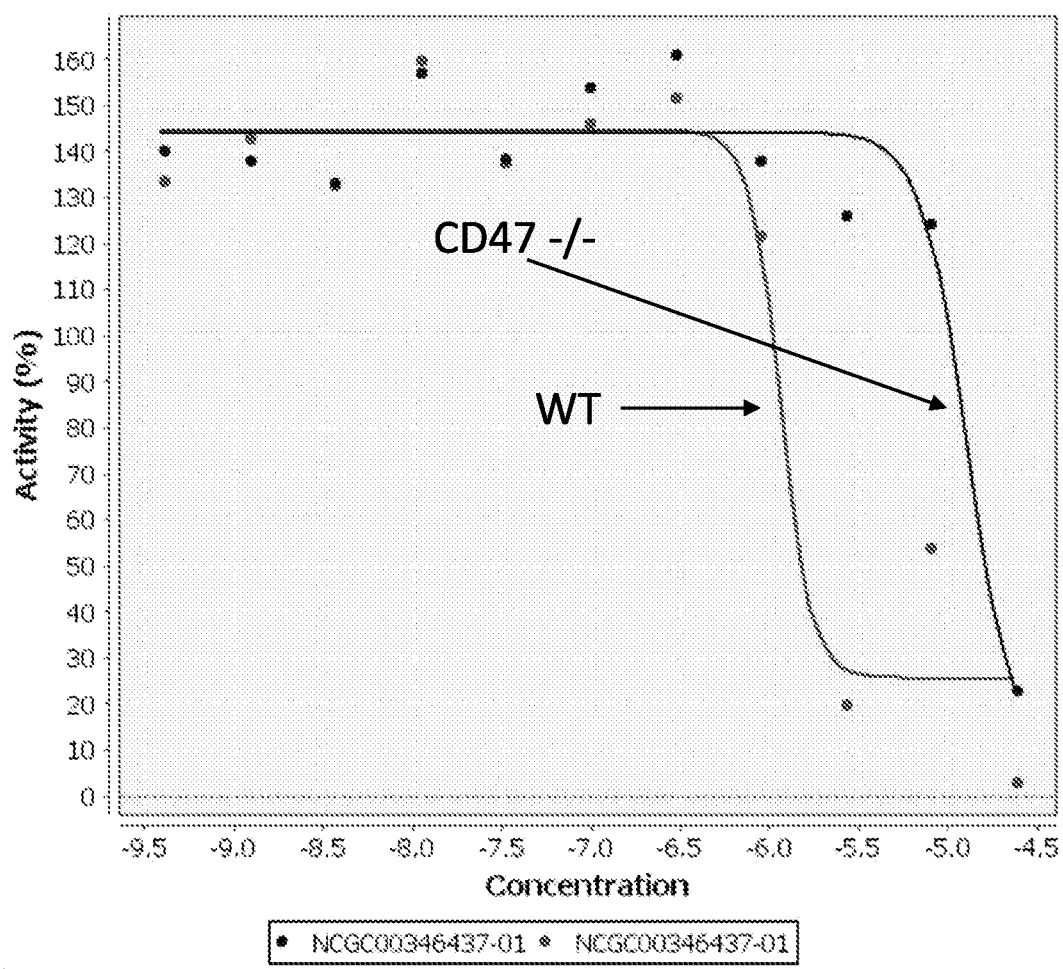
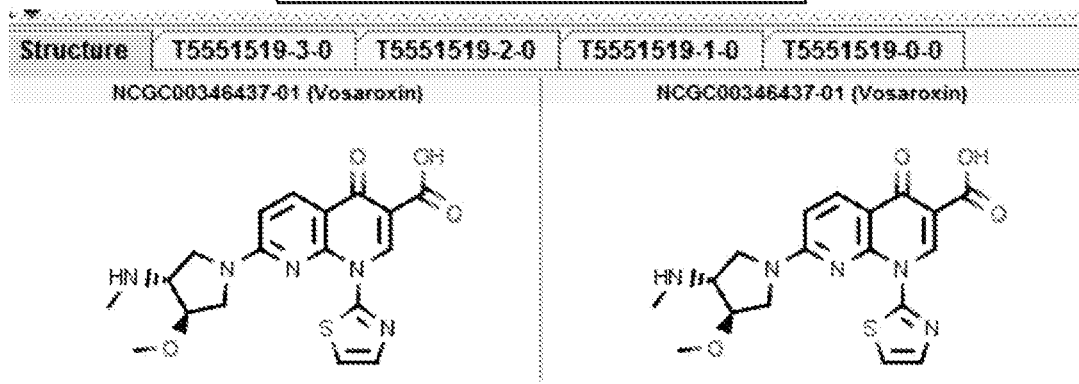

FIG. 15F
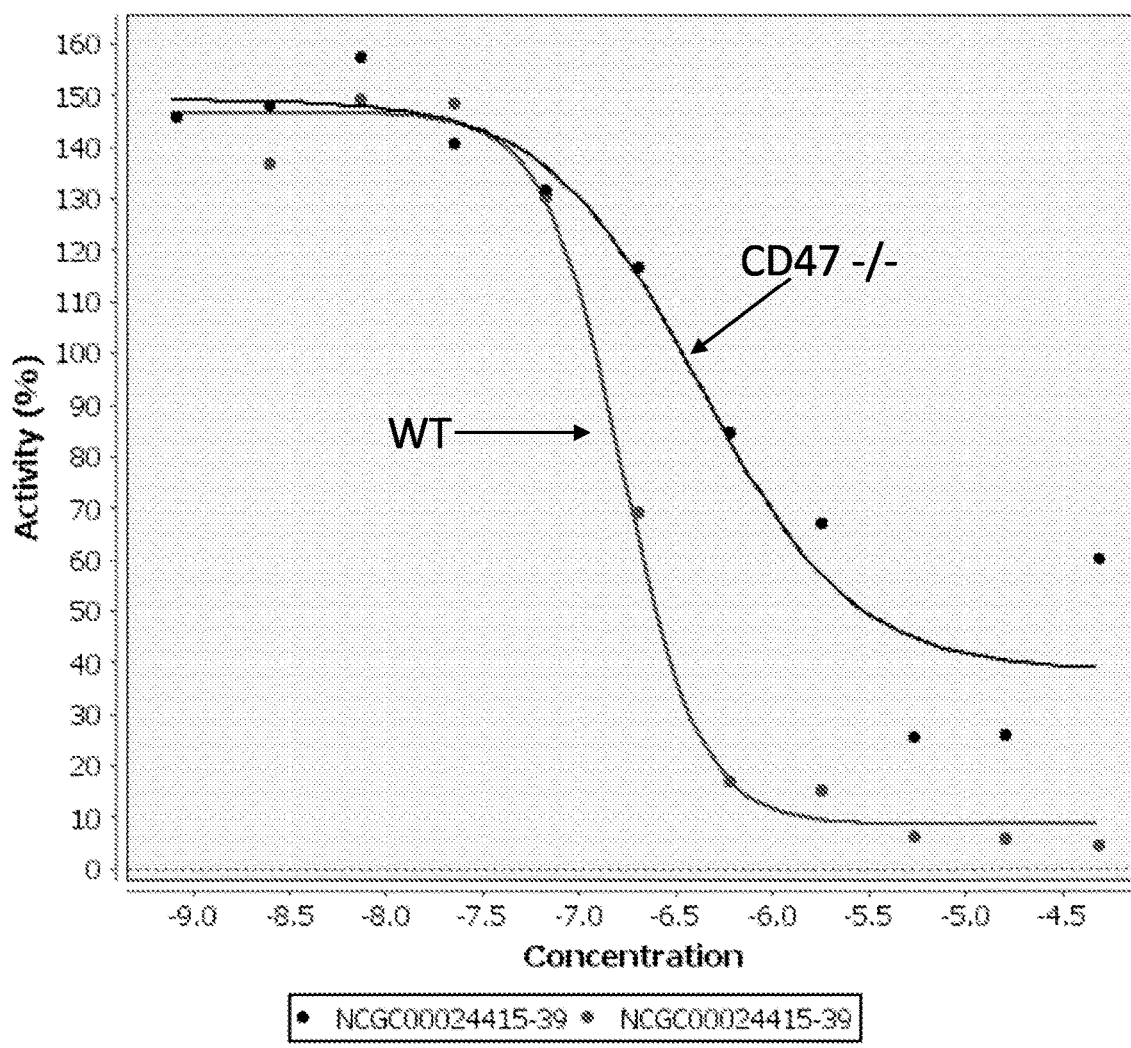
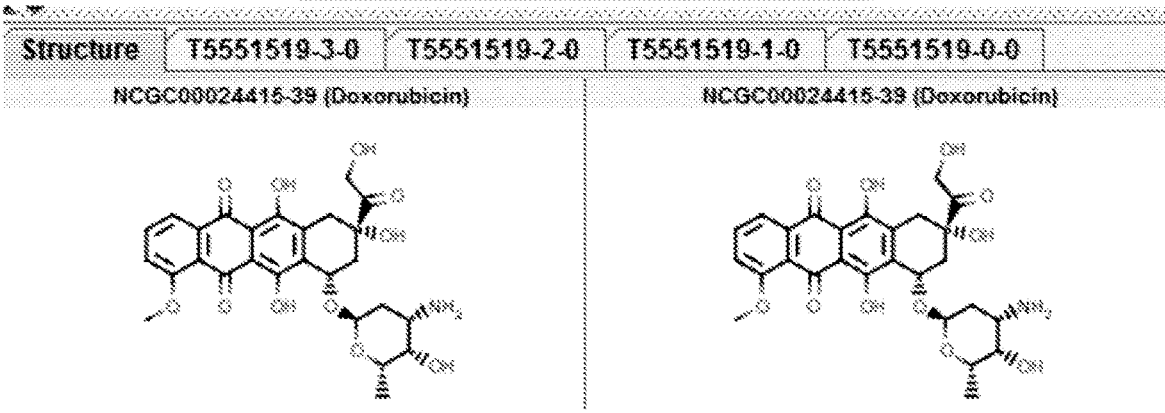

CD47M+Dox

Dox

METHODS FOR MODULATING CHEMOTHERAPEUTIC CYTOTOXICITY

CROSS REFERENCE TO RELATED APPLICATIONS

This is the § 371 U.S. National Stage of International Application No. PCT/US2014/025989, filed Mar. 13, 2014, which was published in English under PCT Article 21(2), which in turn claims the benefit of U.S. Provisional Application No. 61/779,587, filed Mar. 13, 2013, which is incorporated by reference herein in its entirety.

FIELD

This disclosure relates to methods of modulating cytotoxicity of chemotherapeutic agents, particularly reducing cytotoxicity of chemotherapeutic agents to non-cancer cells and/or increasing cytotoxicity of chemotherapeutic agents to cancer cells.

BACKGROUND

Traditional chemotherapeutic agents act by killing rapidly dividing cells, as is typical of cancer cells. However, this means that chemotherapy also damages or kills non-cancer cells that are rapidly dividing (such as cells in bone marrow, the digestive tract, and hair follicles) and this is responsible for many of the side effects of chemotherapy. Many chemotherapy agents damage DNA, for example by intercalating into DNA, interfering with DNA synthesis or replication, or by causing oxidative damage to DNA. For example, DNA intercalating agents such as anthracyclines are widely used in cancer chemotherapy. Even though DNA intercalating agent-based therapies are effective in the treatment of a wide array of cancers, administration of these agents is accompanied by harmful side effects, mainly damaging replicating cells in normal tissue.

Although chemotherapeutic treatment is widely used and effective, it is limited by its detrimental side effects, particularly cardiac toxicity. These toxicities limit the cumulative dose of many chemotherapeutics (particularly anthracyclines) that can safely be administered to a patient. To overcome cardiotoxicity, researchers have introduced modifications to the structure of many chemotherapeutics, but these either decrease efficacy or do not improve the side effect profile. Therefore, the off-target effects of these agents limit their use and there is a continuing need for alternative agents or treatment regimens that can be used in the treatment of diverse cancers to improve survival and quality of life for those with cancer.

SUMMARY

It has surprisingly been discovered that inhibition of CD47 signaling modulates cytotoxic effects of chemotherapeutic agents. In particular, cytotoxicity of chemotherapeutic agents to non-cancer cells (e.g., non-tumor cells) can be dramatically decreased through inhibition of CD47 signaling. This effect is specific to non-cancer cells. Moreover, it has also been discovered that inhibition of CD47 signaling increases the cytotoxicity of chemotherapeutic agents to cancer cells in a subject being treated with chemotherapy. In some embodiments, CD47 signaling blockade reduces cytotoxicity to non-cancer cells and/or increases cytotoxicity to cancer cells of chemotherapeutic agents, particularly those that damage DNA (for example, directly or through interfering with DNA synthesis or replication) or that cause oxidative damage to cells.

Disclosed herein are methods of reducing cytotoxicity of a chemotherapeutic agent to non-cancer cells by administering to a subject with cancer an effective amount of an agent that inhibits CD47 signaling and one or more chemotherapeutic agents. In some embodiments, the inhibitor of CD47 signaling is administered to the subject before, during, or after the administration of the chemotherapeutic agent(s). In some examples, administering to a subject with cancer an effective amount of an agent that inhibits CD47 signaling and a chemotherapeutic agent reduces cardiotoxicity of the chemotherapeutic agent in the subject.

Also disclosed are methods of increasing cytotoxicity of a chemotherapeutic agent to cancer cells or a tumor by administering to a subject with a tumor an effective amount of an agent that inhibits CD47 signaling and a chemotherapeutic agent. In some examples, the inhibitor of CD47 signaling is administered to the subject before, during, or after the administration of the chemotherapeutic agent (for example, a DNA damaging chemotherapeutic agent).

In various embodiments, the agent that inhibits CD47 signaling includes a CD47-binding peptide; a thrombospondin 1 (TSP1)-binding peptide; a CD47 antisense oligonucleotide (such as a CD47 morpholino); a TSP1 antisense oligonucleotide; an anti-CD47 antibody or a fragment thereof, an anti-TSP1 antibody or a fragment thereof; an isolated or recombinant CD47 or TSP1 molecule or soluble fragment thereof, or molecule that binds thereto; an agent that decreases the expression of CD47 or TSP; a small molecule capable of binding to CD47; a small molecule capable of binding to TSP1; or a mixture of two or more thereof. In some examples, the CD47 signaling is TSP1-dependent signaling.

The foregoing and other features of the disclosure will become more apparent from the following detailed description, which proceeds with reference to the accompanying figures.

BRIEF DESCRIPTION OF THE DRAWINGS

FIGS. 5A and 5B are a pair of graphs showing Atg5 (A) and Atg7 (B) gene expression in heart tissue from wild type (WT) or CD47 null (CD47 −/−) mice treated with 10 μg/kg doxorubicin. Samples were collected after 24 hours of treatment.

FIG. 6 is a graph showing cell viability measured by 3-(4,5-dimethylthiazol-2-yl)-5-(3-carboxymethoxyphenyl)-2-(4-sulfophenyl)-2H-tetrazolium (MTS) reduction in wild type (WT) or CD47 null (CD47−/−) Jurkat cells 72 hours after treatment with the indicated concentrations of doxorubicin. n=3, in triplicate. * p<0.005.

FIGS. 7A-D are a series of graphs showing cell viability of 4T1 breast cancer cells (A), B16 mouse melanoma cells (B), CT26 mouse colon carcinoma cells (C), or human umbilical vein endothelial cells (D) in the presence or absence of CD47 blockade. Cells were plated in the presence or absence of 10 μM CD47 morpholino. After 48 hours, cells were treated with the indicated amounts of doxorubicin (10 μg/ml in FIGS. 7B and C). Cell viability was measured 72 hours after treatment by MTS reduction (FIGS. 7A and D) or 24 hours after treatment by lactate dehydrogenase (LDH) release (FIGS. 7B and C). * p<0.001. Control cells were untreated and Endoporter indicates treatment with vehicle without morpholino in FIGS. 7B and C.

FIGS. 14A-F are a series of graphs showing viability of wild-type and CD47 −/− Jurkat cells cultured for 48 hours in the presence of the indicated concentrations of mitoxantrone (FIG. 14A), idarubicin hydrochloride (FIG. 14B), pirarubicin (FIG. 14C), epirubicin hydrochloride (FIG. 14D), vosaroxin (FIG. 14E), and doxorubicin (FIG. 14F).

FIGS. 15A-F are a series of graphs showing viability of wild-type and CD47 −/− Jurkat cells cultured for 48 hours in the presence of the indicated concentrations of topotecan hydrochloride (FIG. 15A), camptothecin (FIG. 15B), 10-hydroxycamptothecin (FIG. 15C), SN-38 (FIG. 15D), irinotecan (FIG. 15E), and rebeccamycin (FIG. 15F).

SEQUENCE LISTING

Figure 1A:
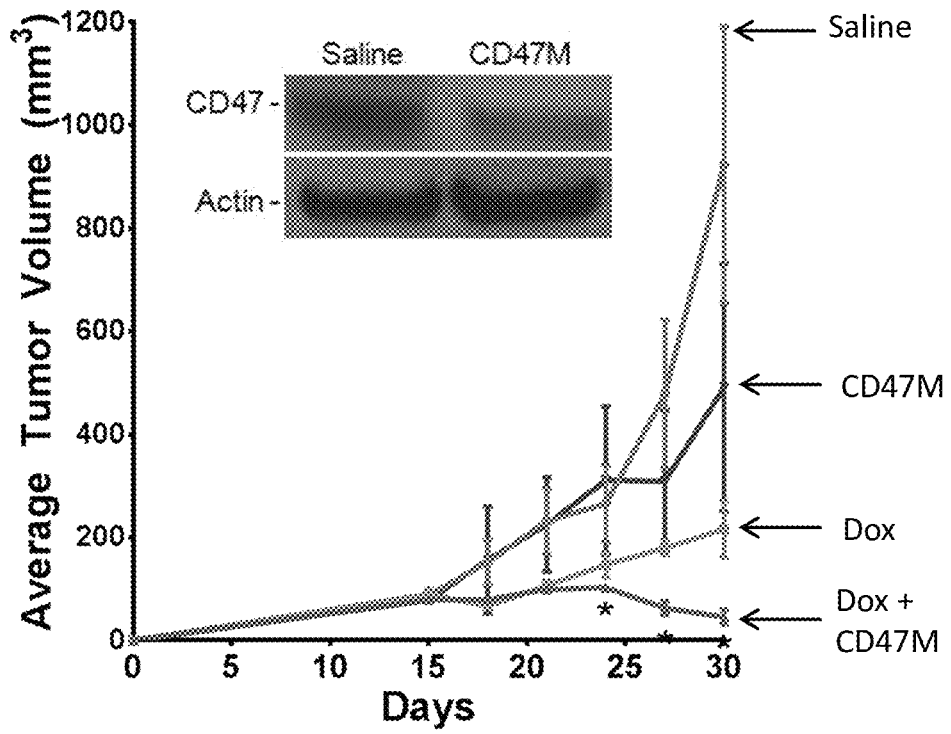
FIG. 1A is a graph showing tumor volume in Balb/c mice injected with 4T1 breast cancer cells in the mammary fat pad and treated with saline (circles), 10 µg/mL Dox (squares), 10 µM CD47 morpholino (CD47M; inverted triangles) or 10 µg/mL Dox plus 10 µM CD47M (triangles). Tumor volume was measured every other day and was calculated using the formula ½ (length×width$^2$). Results are mean±SD, 5 mice per group. *p<0.05. The inset is a digital image of a Western blot showing a decrease in CD47 protein in tumors 48 hours after treatment with CD47 morpholino.

The nucleic acid and/or amino acid sequences provided herewith and in the accompanying sequence listing are shown using standard letter abbreviations for nucleotide bases and amino acids, as defined in 37 C.F.R. 1.822. Only one strand of each nucleic acid sequence is shown, but the complementary strand is understood as included by any reference to the displayed strand.

The Sequence Listing is submitted as an ASCII text file in the form of the file named Sequence_Listing.txt, which was created on Sep. 10, 2015, and is 1077 bytes, which is incorporated by reference herein.

SEQ ID NO: 1 is a thrombospondin 1-derived CD47-binding peptide 7N3 (1102-1112).

SEQ ID NO: 2 is a CD47-binding peptide (also known as peptide 459 or 4N1).

SEQ ID NO: 3 is an antisense morpholino phosphorodiamidate oligonucleotide complementary to human and murine CD47.

DETAILED DESCRIPTION

Thrombospondin 1 (TSP1; also known as THBS1) is an extracellular secreted protein that is involved in a myriad of cellular processes, including platelet aggregation, neurite outgrowth, cell motility, cell survival, and cellular proliferation. Among TSP1's best-characterized functions is inhibition of angiogenesis. Agents that mimic the ability of TSP1 to inhibit angiogenesis are therefore considered possible therapies for cancer. In vitro studies have shown the ability of such agents to block tumor driven angiogenesis. In vivo results in animals have also been encouraging and have led to clinical trials in people. See Rusk et al., *Clin Cancer Res* 12:7456-7464, 2006; Markovic et al., *Am J Clin Oncol* 30:303-309, 2007.

Overexpression of TSP1 has been observed in ischemic tissue, and is proposed to regulate angiogenesis within ischemic tissue (Favier et al., *J Pathol.* 207(3): 358-366, 2005), since TSP1 preferentially interferes with wound healing-associated angiogenesis (Streit et al., *EMBO J.* 19(13): 3272-3282, 2000) and limits revascularization in a model of hind limb ischemia (Kopp et al., *J. Clin. Invest.* 116(12): 3277-3291, 2006). Peptides derived from the type 1 repeats inhibit angiogenesis (Shafiee et al., *IOVS* 41(8): 2378-2388, 2000; Yee et al., *Am J. Pathol.* 165(2): 541-552, 2004; Tolsma et al., *J. Cell Biol.* 122: 497-511, 1993; Armstrong and Bornstein, *Mat. Biol.* 22(1): 63-71, 2003; Guo et al., *Cancer Res.* 58(14): 3154-3162, 1998; Guo et al., *J. Peptide Res* 50:210-221, 1997). Additional TSP1 peptides (e.g., 4N1 and 7N3 classes) have previously been described; see, e.g., U.S. Pat. Nos. 5,399,667; 5,627,265; 6,469,138; 5,357,041; 5,491,130; 5,770,563; 5,849,701; 6,051,549; 6,384,189; 6,458,767; and 7,129,052.

Although identified earlier as "integrin associated protein" (IAP), CD47 was discovered to be a receptor for the C-terminal domain of TSP1 in 1996 (Gao et al., *J. Biol. Chem.* 271: 21-24, 1996). Two members of the signal inhibitory receptor protein family, SIRPα (also known as BIT, SHPS-1 and p84) and SIRPγ are cell-bound counter receptors for CD47 (van Beek et al., *J. Immunol.* 175:7781-87, 2005). CD47 is expressed on many if not all normal cells, and signals in part through coupling to heterotrimeric G proteins of the $G_i$ class (Frazier et al., *J. Biol Chem.* 274:8554-8560, 1999).

TSP1, via binding to CD47, potently limits physiologic NO signaling in all vascular cell types including endothelial cells, vascular smooth muscle cells, and platelets. TSP1-CD47 signaling also directly and acutely regulates tissue blood flow and arterial tone by inhibiting NO-driven vasorelaxation, and exerts anti-vasorelaxive effects on smooth muscle by antagonizing the ability of NO to stimulate cGMP synthesis (Isenberg et al., *Proc Natl Acad Sci USA.* 102(37): 13141-13146, 2005; Isenberg et al., *Cardiovasc Res.,* 71(4): 785-793, 2006; Isenberg et al., *J Biol Chem* 281:26069-26080, 2006, Isenberg et al., *Blood,* 109(5):1945-1952, 2007). Though inhibition of NO signaling may be induced by TSP1 interacting with CD36, this effect occurs at doses 100- to 1000-fold greater than the doses of TSP1 that drive inhibition through CD47. Also, TSP1 inhibition of NO signaling through CD36 cannot occur in the absence of CD47 at any dose; thus, the physiologically relevant pathway is via CD47 (Isenberg et al., *J Biol Chem.* 281(36): 26069-26080, 2006). See also International Patent Publication No. WO 2008/060785, which is incorporated herein by reference in its entirety.

The structure and function of CD47 has been explored using anti-CD47 antibodies and peptide ligands of the receptor. Certain anti-CD47 and TSP1-derived CD47 ligands initiate cell death in breast cancer cell lines (Manna and Frazier, *Cancer Res.* 64:1026-1036, 2004) and Jurkat T cells (Manna and Frazier, *J Immunol.* 170(7):3544-3553, 2003). These, and similar experiments, led to the hypothesis that CD47 is necessary for FAS-mediated apoptosis of Jurkat T cells (Manna et al., *J Biol. Chem.* 280(33):29637-29644, 2005). Synthetic peptides derived from the full-length sequence of CD47 have been used to probe its structure (Rebres et al., *J. Biol. Chem.* 276(37):34607-34616, 2001). Ligation of CD47 induces actin polymerization (Rebres et al., *J. Biol. Chem.* 276(10):7672-7680, 2001), and its ligation by peptides derived from the carboxy-terminus of TSP1 stimulates the integrin-mediated adhesion of melanoma cells to specific substrates (Barazi et al., *J. Biol. Chem.* 277(45):42859-42866, 2002; Gao et al., *J. Cell Biol.* 135(2):533-544, 1996).

Different antibodies engaging CD47 can exert opposing stimulatory and inhibitory effects on cells (Li et al., *J Immunol* 166:2427-2436, 2001; Waclavicek et al., *J Immunol* 159:5345-5354, 1997; Pettersen et al., *J Immunol* 162: 7031-7040, 1999; Ticchioni et al., *J Immunol* 158:677-684, 1997). Likewise, a specific CD47 ligand can act as an agonist or an antagonist in different contexts. For instance, CD47 ligation by a particular ligand may have different effects in isolated cells than in vivo. Therefore, some effects of CD47 antibodies that have been defined using isolated cells do not extrapolate to in vivo activities, and the function of a specific CD47 ligand in vivo cannot be predicted solely on the basis of in vitro testing. However, agents that block CD47 function in vitro consistently show protective activities in mouse, rat, and pig models of stress. These include fixed ischemia, ischemia-reperfusion, and radiation injury (Maxhimer et al., *Plast Reconstr. Surg.* 124:1880-1889, 2009; Maxhimer et al., *Sci. Transl. Med.* 1:3ra7, 2009; International Patent Publication Nos. WO 2008/060785 and WO 2010/017332, which are incorporated herein by reference in their entirety).

Some of this tissue protection is mediated by increased NO/cGMP signaling, but additional cytoprotective pathways are also involved. For example, radioprotection caused by CD47 blockade involves activation of a protective autophagy pathway (Soto-Pantoja et al., *Autophagy* 8:1628-1642, 2012). This protective autophagy response is evident in isolated cells and in tissues of an irradiated mouse. In addition to these cell autonomous effects of CD47 blockade on tumor cells, enhanced ablation of tumors by a CD47 antibody in mouse xenograft models or in conjunction with irradiation in syngeneic tumor models has been proposed to involve increased clearance of damaged tumor cells by phagocytes (Maxhimer et al., *Sci. Transl. Med.* 1:3ra7, 2009; Majeti et al. *Cell.* 138:286-299, 2009). CD47 blockade using an antibody is also known to enhance the efficacy of the CD20 antibody rituximab to treat non-Hodgkin's lymphoma (Chao et al., *Cell* 142:699-713, 2010), and this was proposed to involve a similar enhancement of SIRP-dependent phagocytic clearance and/or enhanced antibody-dependent cellular cytotoxicity rather than direct CD47-dependent effects on the tumor cells.

It is shown herein that blockade of CD47 signaling in cancer cells surprisingly enhances sensitivity of cancer cells to chemotherapy treatment in vitro and tumor in vivo, whereas blockade of CD47 signaling in non-cancer cells reduces cytotoxicity of the chemotherapy treatment in these cells and tissues. Without being bound by theory, contrary to the existing theory invoking SIRPα-dependent phagocyte activity to explain effects of CD47 blocking antibodies on tumor growth, the increased sensitivity of cancer cells to chemotherapy in combination with inhibition of CD47 signaling appears to be cell-autonomous and associated with an increase in mitophagy. Similarly, the reduced cytotoxicity of chemotherapeutic agents to non-cancer cells in combination with inhibition of CD47 signaling in those cells appears to be associated with an increase in autophagy that may be regulated directly by CD47 or involve disruption of the interaction of CD47 with its soluble ligand TSP1.

I. Abbreviations

5-FU 5-fluorouracil
CD47 M CD47 morpholino
CPT camptothecin
Dox doxorubicin
ECAR extracellular acidification rate
ECG electrocardiogram
LDH lactate dehydrogenase
LVEF left ventricular ejection fraction
MTS 3-(4,5-dimethylthiazol-2-yl)-5-(3-carboxymethoxyphenyl)-2-(4-sulfophenyl)-2H-tetrazolium
OCR oxygen consumption rate SIRPα signal-regulatory protein α
TSP1 thrombospondin 1
TUNEL terminal deoxynucleotidyl transferase dUTP nick end labeling

II. Terms

Unless otherwise noted, technical terms are used according to conventional usage. Definitions of common terms in molecular biology can be found in Benjamin Lewin, Genes V, published by Oxford University Press, 1994 (ISBN 0-19-854287-9); Kendrew et al. (eds.), *The Encyclopedia of Molecular Biology*, published by Blackwell Science Ltd., 1994 (ISBN 0-632-02182-9); and Robert A. Meyers (ed.), *Molecular Biology and Biotechnology: a Comprehensive Desk Reference*, published by VCH Publishers, Inc., 1995 (ISBN 1-56081-569-8).

Administration: Administration of an active compound or composition can be by any route known to one of ordinary skill in the art. Administration can be local or systemic. Examples of local administration include, but are not limited to, topical administration, subcutaneous administration, intramuscular administration, intrathecal administration, intrapericardial administration, intra-ocular administration, topical ophthalmic administration, or administration to the nasal mucosa or lungs by inhalational administration. In addition, local administration includes routes of administration typically used for systemic administration, for example by directing intravascular administration to the arterial supply for a particular organ. Thus, in particular embodiments, local administration includes intra-arterial administration and intravenous administration when such administration is targeted to the vasculature supplying a particular organ. Local administration also includes the incorporation of active compounds and agents into implantable devices or constructs, such as vascular stents or other reservoirs, which release the active agents and compounds over extended time intervals for sustained treatment effects.

Systemic administration includes any route of administration designed to distribute an active compound or composition widely throughout the body via the circulatory system. Thus, systemic administration includes, but is not limited to intra-arterial and intravenous administration. Systemic administration also includes, but is not limited to, oral administration, topical administration, subcutaneous administration, intramuscular administration, transdermal administration, or administration by inhalation, when such administration is directed at absorption and distribution throughout the body by the circulatory system.

Antibody: A protein (or protein complex) that includes one or more polypeptides substantially encoded by immunoglobulin genes or fragments of immunoglobulin genes. The recognized immunoglobulin genes include the kappa, lambda, alpha, gamma, delta, epsilon and mu constant region genes, as well as the myriad immunoglobulin variable region genes. Light chains are classified as either kappa or lambda. Heavy chains are classified as gamma, mu, alpha, delta, or epsilon, which in turn define the immunoglobulin classes, IgG, IgM, IgA, IgD and IgE, respectively.

The basic immunoglobulin (antibody) structural unit is generally a tetramer. Each tetramer is composed of two identical pairs of polypeptide chains, each pair having one light (about 25 kD) and one heavy chain (about 50-70 kD). The N-terminus of each chain defines a variable region of about 100 to 110 or more amino acids primarily responsible for antigen recognition. The terms variable light chain ($V_L$) and variable heavy chain ($V_H$) refer, respectively, to these light and heavy chains.

As used herein, the term antibody includes intact immunoglobulins as well as a number of well-characterized fragments produced by digestion with various peptidases, or genetically engineered artificial antibodies. Thus, for example, pepsin digests an antibody below the disulfide linkages in the hinge region to produce F(ab)'$_2$, a dimer of Fab which itself is a light chain joined to $V_H$-$C_H$ by a disulfide bond. The F(ab)'$_2$ may be reduced under mild conditions to break the disulfide linkage in the hinge region thereby converting the F(ab)'$_2$ dimer into an Fab' monomer. The Fab' monomer is essentially a Fab with part of the hinge region (see, *Fundamental Immunology*, W. E. Paul, ed., Raven Press, N.Y., 1993). While various antibody fragments are defined in terms of the digestion of an intact antibody, it will be appreciated that Fab' fragments may be synthesized de novo either chemically or by utilizing recombinant DNA methodology. Thus, the term antibody as used herein also includes antibody fragments either produced by the modification of whole antibodies or synthesized de novo using recombinant DNA methodologies.

Antibodies for use in the methods, compositions, and systems of this disclosure can be monoclonal or polyclonal. Merely by way of example, monoclonal antibodies can be prepared from murine hybridomas according to the classical method of Kohler and Milstein (*Nature* 256:495-497, 1975) or derivative methods thereof. Detailed procedures for monoclonal antibody production are described in Harlow and Lane (*Using Antibodies, A Laboratory Manual*, CSHL, New York, 1998).

The terms "bind specifically" and "specific binding" refer to the ability of a specific binding agent (such as, an antibody) to bind to a target molecular species in preference to binding to other molecular species with which the specific binding agent and target molecular species are admixed. A specific binding agent is said specifically to recognize a target molecular species when it can bind specifically to that target.

A single-chain antibody (scFv) is a genetically engineered molecule containing the $V_H$ and $V_L$ domains of one or more antibody(ies) linked by a suitable polypeptide linker as a genetically fused single chain molecule (see, for example, Bird et al., *Science*, 242:423-426, 1988; Huston et al., *Proc. Natl. Acad. Sci.*, 85:5879-5883, 1988). Diabodies are bivalent, bispecific antibodies in which $V_H$ and $V_L$ domains are expressed on a single polypeptide chain, but using a linker that is too short to allow for pairing between the two domains on the same chain, thereby forcing the domains to pair with complementary domains of another chain and creating two antigen binding sites (see, for example, Holliger et al., *Proc. Natl. Acad. Sci.*, 90:6444-6448, 1993; Poljak et al., *Structure*, 2:1121-1123, 1994). One or more complementarity determining regions (CDRs) may be incorporated into a molecule either covalently or noncovalently to make the resultant molecule an immunoadhesin. An immunoadhesin may incorporate the CDR(s) as part of a larger polypeptide chain, may covalently link the CDR(s) to another polypeptide chain, or may incorporate the CDR(s) noncovalently. The CDRs permit the immunoadhesin to specifically bind to a particular antigen of interest. A chimeric antibody is an antibody that contains one or more regions from one antibody and one or more regions from one or more other antibodies.

An antibody may have one or more binding sites. If there is more than one binding site, the binding sites may be identical to one another or may be different. For instance, a naturally-occurring immunoglobulin has two identical binding sites, a single-chain antibody or Fab fragment has one binding site, while a bispecific or bifunctional antibody has two different binding sites.

A neutralizing antibody or an inhibitory antibody is an antibody that inhibits at least one activity of a target, usually a polypeptide, such as by blocking the binding of the polypeptide to a ligand to which it normally binds, or by disrupting or otherwise interfering with a protein-protein interaction of the polypeptide with a second polypeptide. An activating antibody is an antibody that increases an activity of a polypeptide. Antibodies may function as mimics of a target protein activity, or as blockers of the target protein activity, with therapeutic effect derived therein.

Antisense, Sense, and Antigene: Double-stranded DNA (dsDNA) has two strands, a 5'→3' strand, referred to as the plus strand, and a 3'→5' strand (the reverse compliment), referred to as the minus strand. Because RNA polymerase adds nucleic acids in a 5'→3' direction, the minus strand of the DNA serves as the template for the RNA during transcription. Thus, the RNA formed will have a sequence complementary to the minus strand and identical to the plus strand (except that U is substituted for T).

Antisense molecules are molecules that are specifically hybridizable or specifically complementary to either RNA or plus strand DNA. Sense molecules are molecules that are specifically hybridizable or specifically complementary to the minus strand of DNA. Antigene molecules are either antisense or sense molecules complimentary to a dsDNA target. In one embodiment, an antisense molecule specifically hybridizes to a target mRNA and inhibits translation of the target mRNA.

Anthracycline: A class of chemotherapeutic agents that are DNA intercalators. Anthracyclines were originally isolated from *Streptomyces peucetius*. Anthracyclines include daunorubicin (trade names: Cerubidine, DaunoXome®), doxorubicin (trade names: Adriamycin, Rubex, Doxil®, Caelyx, Myocet™) epirubicin (trade name: Ellence®), idarubicin (trade name: Idamycin), pirarubicin, and valrubicin (trade name: Valstar®). Analogs of anthracyclines, such as mitoxantrone (trade name: Novantrone®) and vosaroxin, are also considered to be anthracycline-like compounds, and are part of the class of anthracycline chemotherapeutic agents.

Cancer: A malignant neoplasm that has undergone characteristic anaplasia with loss of differentiation, increased rate of growth, invasion of surrounding tissue, and is capable of metastasis. For example, breast cancer is a malignant neoplasm that arises in or from breast tissue (such as a ductal carcinoma) and lung cancer is a malignant neoplasm that arises in or from lung tissue (such as non-small cell lung cancer or small cell lung cancer). In other examples, prostate cancer is a malignant neoplasm that arises in or from prostate tissue and colorectal cancer is cancer that arises in or from large bowel (colon or rectal tissue). Cancer also includes hematological malignancies (such as leukemia) which arise in blood cells and/or bone marrow.

Residual cancer is cancer that remains in a subject after any form of treatment given to the subject to reduce or eradicate cancer. Metastatic cancer is a cancer at one or more sites in the body other than the site of origin of the original (primary) cancer from which the metastatic cancer is derived. Local recurrence is reoccurrence of the cancer at or near the same site (such as in the same tissue) as the original cancer.

CD47: CD47 is an atypical member of the immunoglobulin and the G protein-coupled receptor superfamilies. It consists of an N-terminal extracellular IgV domain, five transmembrane segments and an alternatively spliced cytoplasmic tail (Brown and Frazier, *Trends Cell Biol.* 11(3): 130-135, 2001). CD47 sequences are publically available, such as GenBank Accession Nos. NM_198793, NM_001777, and NM_010581 (nucleic acids) and NP_942088, NP_001768, and NP_034711 (protein), all of which are incorporated herein by reference as present in GenBank on Mar. 1, 2013. One of ordinary skill in the art can identify additional CD47 sequences, including variant sequences.

Chemotherapeutic agent: A chemical agent with therapeutic usefulness in the treatment of diseases characterized by abnormal cell growth. Such diseases include tumors, neoplasms, and cancer, as well as diseases characterized by hyperplastic growth such as psoriasis. In one embodiment, a chemotherapeutic agent is an agent of use in treating neoplasms such as solid tumors or hematopoietic malignancies. One of ordinary skill in the art can readily identify a chemotherapeutic agent of use (e.g., see Slapak and Kufe, *Principles of Cancer Therapy*, Chapter 86 in Harrison's Principles of Internal Medicine, 14th edition; Perry et al., *Chemotherapy*, Ch. 17 in Abeloff, *Clinical Oncology* $2^{nd}$ ed., 2000 Churchill Livingstone, Inc; Baltzer L, Berkery R (eds): *Oncology Pocket Guide to Chemotherapy*, 2nd ed. St. Louis, Mosby-Year Book, 1995; Fischer D S, Knobf M F, Durivage H J (eds): *The Cancer Chemotherapy Handbook,* 4th ed. St. Louis, Mosby-Year Book, 1993).

Cytotoxicity: The quality of being toxic to cells. Compounds that are cytotoxic damage cells and may cause or promote cell death (such as necrosis or apoptosis) or may inhibit cell growth or division. Chemotherapeutic or antineoplastic agents are examples of cytotoxic compounds that in some examples may selectively kill dividing cells. A specific form of cytotoxicity is cardiotoxicity, which refers to the quality of being cytotoxic to cardiac cells or tissue, for example cytotoxic to cardiomyocytes or cardiac myoblasts.

DNA damaging agent: Agents that interfere with DNA structure, DNA synthesis, or DNA replication. Some chemotherapeutic agents are DNA damaging agents, such as DNA intercalating agents, DNA alkylating agents, antimetabolites that inhibit nucleotide synthesis (such as purine analogs, pyrimidine analogs, or folate analogs), topoisomerase inhibitors, or agents that cause oxidative damage (for example, anthracyclines and platinum compounds).

Effective amount: A quantity of an agent or compound sufficient to achieve a desired effect in a subject being treated. An effective amount of a compound can be administered in a single dose, or in several doses, for example daily, during a course of treatment. However, the effective amount of the compound will be dependent on the compound applied, the subject being treated, the severity and type of the affliction, and the manner of administration of the compound.

Gene expression: The process by which the coded information of a nucleic acid transcriptional unit (including, for example, genomic DNA or cDNA) is converted into an operational, non-operational, or structural part of a cell, often including the synthesis of a protein. Gene expression can be influenced by external signals; for instance, exposure of a subject to an agent that inhibits gene expression. Expression of a gene also may be regulated anywhere in the pathway from DNA to RNA to protein. Regulation of gene expression occurs, for instance, through controls acting on transcription, translation, RNA transport and processing, degradation of intermediary molecules such as mRNA, or through activation, inactivation, compartmentalization or degradation of specific protein molecules after they have been made, or by combinations thereof. Gene expression may be measured at the RNA level or the protein level and by any method known in the art, including Northern blot, RT-PCR, Western blot, or in vitro, in situ, or in vivo protein activity assay(s).

The expression of a nucleic acid may be modulated compared to a control state, such as at a control time (for example, prior to administration of a substance or agent that affects regulation of the nucleic acid under observation) or in a control cell or subject, or as compared to another nucleic acid. Such modulation includes but is not necessarily limited to overexpression, underexpression, or suppression of expression. In addition, it is understood that modulation of nucleic acid expression may be associated with, and in fact may result in, a modulation in the expression of an encoded protein or even a protein that is not encoded by that nucleic acid.

It is understood that interfering with or inhibiting gene expression is relative, and does not require absolute suppression of the gene. Thus, in certain embodiments, interfering with or inhibiting gene expression of a target gene requires that, following application of an agent, the gene is expressed at least 5% less than prior to application (or compared to a control), at least 10% less, at least 15% less, at least 20% less, at least 25% less, or even more reduced. Thus, in some particular embodiments, application of an agent reduces expression of the target gene by about 30%, about 40%, about 50%, about 60%, or more for example, compared to a control. In specific examples, where the agent is particularly effective, expression is reduced by 70%, 80%, 85%, 90%, 95%, or even more compared to a control. Gene expression is substantially eliminated when expression of the gene is reduced by 90%, 95%, 98%, 99% or even 100%.

Inhibiting protein activity: To decrease, limit, or block an action, function or expression of a protein. The phrase "inhibit protein activity" is not intended to be an absolute term. Instead, the phrase is intended to convey a wide range of inhibitory effects that various agents may have on the normal (for example, uninhibited or control) protein activity. Inhibition of protein activity may, but need not, result in an increase in the level or activity of an indicator of the protein's activity. By way of example, this can happen when the protein of interest is acting as an inhibitor or suppressor of a downstream indicator. Thus, protein activity may be inhibited when the level or activity of any direct or indirect indicator of the protein's activity is changed (for example, increased or decreased) by at least 10%, at least 20%, at least 30%, at least 50%, at least 80%, at least 100% or at least 250% or more as compared to control measurements of the same indicator.

Inhibition of protein activity may also be effected, for example, by inhibiting expression of the gene encoding the protein or by decreasing the half-life of the mRNA encoding the protein.

Isolated: An isolated biological component (such as a nucleic acid, peptide or protein) has been substantially separated, produced apart from, or purified away from other biological components in the cell of the organism in which the component naturally occurs, for instance, other chromosomal and extrachromosomal DNA and RNA, and proteins. Nucleic acids, peptides and proteins that have been isolated thus include nucleic acids and proteins purified by standard purification methods. The term also embraces nucleic acids, peptides and proteins prepared by recombinant expression in a host cell as well as chemically synthesized nucleic acids. The terms isolated and purified do not require absolute purity; rather, it is intended as a relative term. Thus, for example, an isolated nucleic acid or peptide preparation is one in which the nucleic acid, peptide, or protein is more enriched than it is in its natural environment within a cell. Preferably, a preparation is purified such that the nucleic acid, peptide, or protein represents at least 50% of the total nucleic acid, peptide, or protein content of the preparation.

Morpholino: A morpholino oligo is structurally different from natural nucleic acids, with morpholino rings replacing the ribose or deoxyribose sugar moieties and non-ionic phosphorodiamidate linkages replacing the anionic phosphates of DNA and RNA. Each morpholino ring suitably positions one of the standard bases (A, G, C, T/U), so that a 25-base morpholino oligo strongly and specifically binds to its complementary 25-base target site in a strand of RNA via Watson-Crick pairing. Because the backbone of the morpholino oligo is not recognized by cellular enzymes of signaling proteins, it is stable to nucleases and does not trigger an innate immune response through the toll-like receptors. This avoids loss of oligo, inflammation or interferon induction. Morpholinos can be delivered by a number of techniques, including direct injection to tissues or via infusion pump and intravenous bolus. A morpholino is one example of a stabilized nucleic acid molecule.

Oligonucleotide: A plurality of joined nucleotides joined by native phosphodiester bonds, between about 6 and about 300 nucleotides in length. An oligonucleotide analog refers to moieties that function similarly to oligonucleotides but have non-naturally occurring portions. For example, oligonucleotide analogs can contain non-naturally occurring portions, such as altered sugar moieties or inter-sugar linkages, such as a phosphorothioate oligodeoxynucleotide. Functional analogs of naturally occurring polynucleotides can bind to RNA or DNA, and include stabilized oligonucleotides, such as peptide nucleic acid (PNA) molecules and morpholinos.

Particular oligonucleotides and oligonucleotide analogs can include linear sequences up to about 200 nucleotides in length, for example a sequence (such as DNA or RNA) that is at least 6 bases, for example at least 8, 10, 15, 20, 25, 30, 35, 40, 45, 50, 100 or even 200 bases long, or from about 6 to about 50 bases, for example about 10-25 bases, such as 12, 15 20, or 25 bases.

Pharmaceutically acceptable carriers: The pharmaceutically acceptable carriers useful in this disclosure are conventional. *Remington: The Science and Practice of Pharmacy*, The University of the Sciences in Philadelphia, Editor, Lippincott, Williams, & Wilkins, Philadelphia, Pa., 21$^{st}$ Edition (2005), describes compositions and formulations suitable for pharmaceutical delivery of the compounds herein disclosed.

In general, the nature of the carrier will depend on the particular mode of administration being employed. For instance, parenteral formulations usually comprise injectable fluids that include pharmaceutically and physiologically acceptable fluids such as water, physiological saline, balanced salt solutions, aqueous dextrose, glycerol or the like as a vehicle. For solid compositions (for example, powder, pill, tablet, or capsule forms), conventional nontoxic solid carriers can include, for example, pharmaceutical grades of mannitol, lactose, starch, or magnesium stearate. In addition to biologically-neutral carriers, pharmaceutical compositions to be administered can contain minor amounts of non-toxic auxiliary substances, such as wetting or emulsifying agents, preservatives, and pH buffering agents and the like, for example sodium acetate or sorbitan monolaurate.

Purified: In a more pure form than is found in nature. The term purified does not require absolute purity; rather, it is intended as a relative term. Thus, for example, a purified protein preparation is one in which the protein referred to is more pure than the protein in its natural environment within a cell.

The term substantially purified as used herein refers to a molecule (for example, a nucleic acid, polypeptide, oligonucleotide, etc.) that is substantially free of other proteins, lipids, carbohydrates, or other materials with which it is naturally associated. In one non-limiting embodiment, a substantially purified molecule is a polypeptide that is at least 50% free of other proteins, lipids, carbohydrates, or other materials with which it is naturally associated. In another embodiment, the polypeptide is at least at least 80% free of other proteins, lipids, carbohydrates, or other materials with which it is naturally associated. In yet other embodiments, the polypeptide is at least 90% or at least 95% free of other proteins, lipids, carbohydrates, or other materials with which it is naturally associated.

RNA interference (RNA silencing; RNAi): A gene-silencing mechanism whereby specific double-stranded RNA (dsRNA) trigger the degradation of homologous mRNA (also called target RNA). Double-stranded RNA is processed into small interfering RNAs (siRNA), which serve as a guide for cleavage of the homologous mRNA in the RNA-induced silencing complex (RISC). The remnants of the target RNA may then also act as siRNA; thus resulting in a cascade effect.

Small molecule inhibitor: A molecule, typically with a molecular weight less than 1000 Daltons, or in some embodiments, less than about 500 Daltons, wherein the molecule is capable of inhibiting, to some measurable extent, an activity of some target molecule.

Stabilized nucleic acid molecules: A variety of synthetic nucleic acid derivatives with increased stability as compared to native (e.g., non-modified) nucleic acids. Stabilized nucleic acid molecules include nucleic acids where the labile phosphodiester bonds in nucleic acids are replaced with more stable phosphoramidates or peptide amide backbones, or oligonucleotides including one or more such nucleic acid derivatives. Also included are nucleic acids having a substitution of the deoxyribosyl moiety with a more stable morpholine derivative (e.g., morpholinos) or oligonucleotides including one or more morpholino nucleic acids. In other examples, stabilized nucleic acid molecules include "locked" nucleic acids where the ribose moiety is modified with a bridge connecting the 2' oxygen and the 4' carbon, or oligonucleotides including one or more locked nucleic acid.

Subject: Living multi-cellular organisms, including vertebrate organisms, a category that includes both human and non-human mammals.

Target sequence: A target sequence is a portion of ssDNA, dsDNA, or RNA that, upon hybridization to an oligonucleotide or oligonucleotide analog (e.g., a morpholino), results in the inhibition of expression of the target. Either an antisense or a sense molecule can be used to target a portion of dsDNA, as both will interfere with the expression of that portion of the dsDNA. The antisense molecule can bind to the plus strand, and the sense molecule can bind to the minus strand. Thus, target sequences can be ssDNA, dsDNA, and RNA.

Thrombospondin 1 (TSP1): TSP1 contains three type 1 repeat structural domains and a carboxy-terminal domain that were identified as the loci of the full-length protein's anti-angiogenic functionality (Lawler, *Curr. Opin. Cell Biol.* 12(5): 634-640, 2000). TSP1 sequences are publically available, such as GenBank Accession Nos. NM_003246 and NM_011580 (nucleic acids) and NP_003237 and NP_035710 (protein), all of which are incorporated herein by reference as present in GenBank on Mar. 1, 2013. One of ordinary skill in the art can identify additional TSP1 sequences, including variant sequences.

Treating a disease: Includes inhibiting or preventing the partial or full development or progression of a disease, for example in a person who is known to have a predisposition to a disease. Furthermore, treating a disease refers to a therapeutic intervention that ameliorates at least one sign or symptom of a disease or pathological condition, or interferes with a pathophysiological process, after the disease or pathological condition has begun to develop.

Tumor: The product of neoplasia is a neoplasm (a tumor), which is an abnormal growth of tissue that results from excessive cell division. A tumor that does not invade surrounding tissue or metastasize is referred to as "benign." A tumor that invades the surrounding tissue and/or can metastasize is referred to as "malignant."

Under conditions sufficient for: A phrase that is used to describe any environment that permits the desired activity. In one example, this includes administering an effective amount of a composition that includes a peptide, antibody, or oligonucleotide (e.g., morpholino), sufficient to enable the desired activity.

The singular terms "a," "an," and "the" include plural referents unless context clearly indicates otherwise. Similarly, the word "or" is intended to include "and" unless the context clearly indicates otherwise. Hence "comprising A or B" means "including A, or including B, or including A and B." It is further to be understood that all base sizes or amino acid sizes, and all molecular weight or molecular mass values, given for nucleic acids or polypeptides are approximate, and are provided for description. Although methods and materials similar or equivalent to those described herein can be used in the practice or testing of the present invention, suitable methods and materials are described below. All publications, patent applications, patents, and other references mentioned herein are incorporated by reference in their entirety.

Unless otherwise explained, all technical and scientific terms used herein have the same meaning as commonly understood by one of ordinary skill in the art to which this invention belongs. In case of conflict, the present specification, including explanations of terms, will control. In addition, the materials, methods, and examples are illustrative only and not intended to be limiting.

III. Methods of Reducing Cytotoxicity and/or Increasing Anti-Tumor Effects of Chemotherapeutic Agents Disclosed herein are methods of reducing cytotoxicity of a chemotherapeutic agent to non-cancer cells by administering to a subject with cancer an effective amount of an agent that inhibits CD47 signaling and one or more chemotherapeutic agents (such as DNA damaging chemotherapeutic agents). Also disclosed herein are methods of increasing cytotoxicity of a chemotherapeutic agent to cancer cells (such as increasing the anti-tumor effect of a chemotherapeutic agent) by administering to a subject with cancer an effective amount of an agent that inhibits CD47 signaling and one or more chemotherapeutic agents. In some examples, administering to a subject with cancer an effective amount of an agent that inhibits CD47 signaling and one or more chemotherapeutic agents both reduces cytotoxicity of the chemotherapeutic agent to non-cancer cells and increases cytotoxicity of the chemotherapeutic agent to cancer cells. In some embodiments, the inhibitor of CD47 signaling is administered to the subject before, during, or after the administration of the chemotherapeutic agent(s).

In addition to desired cytotoxicity to cancer cells, many chemotherapeutic agents cause significant cytotoxicity to non-cancer ("normal") cells, often limiting the dose and/or duration of chemotherapy that can be administered to a subject. Common side effects of chemotherapeutic agents include myelosuppression (anemia, neutropenia, leukopenia, and/or thrombocytopenia), gastrointestinal effects (nausea, vomiting, and/or diarrhea), hair loss, cardiac damage (referred to as cardiotoxicity, including but not limited to arrhythmia, cardiomyopathy, and/or congestive heart failure), nephrotoxicity, hepatotoxicity, and peripheral neuropathy. These side effects are due to cytotoxicity of the chemotherapeutic agent to non-cancer cells. It has surprisingly been discovered that inhibition of CD47 signaling in combination with a chemotherapeutic agent (for example, before, after, or during administration of the chemotherapeutic agent) reduces damage to non-cancer cells or tissues, while maintaining or even increasing the cytotoxicity of the chemotherapeutic agent to cancer cells.

In some embodiments, the disclosed methods also include detecting a reduction of cytotoxicity of a chemotherapeutic agent to non-cancer cells in a subject administered an agent that inhibits CD47 signaling and a chemotherapeutic agent. One of ordinary skill in the art can identify methods to detect a reduction in cytotoxicity to non-cancer cells, as discussed below in Section IIIB. In additional embodiments, the disclosed methods also include selecting a subject at risk for cytotoxicity of a chemotherapeutic reagent to non-cancer cells for administration of an agent that inhibits CD47 signaling and a chemotherapeutic agent. One of ordinary skill in the art can identify a subject at risk for cytotoxicity of a chemotherapeutic agent to non-cancer cells. Risk factors for cytotoxicity are discussed below in Section IIIB.

Agents that inhibit CD47 signaling include anti-CD47 antibodies, or fragments thereof; CD47-binding peptides; CD47 antisense oligonucleotides (such as a CD47 morpholino); anti-TSP1 antibodies, or fragments thereof; TSP1-binding peptides; TSP1 antisense oligonucleotides (such as a TSP1 morpholino); small molecules capable of binding to CD47; small molecules capable of binding to TSP1; or combinations of two or more thereof. Inhibitors of CD47 signaling are discussed in more detail in Section IV, below.

In some examples, the agent that inhibits CD47 signaling is administered to the subject before the chemotherapeutic agent. For example, the agent that inhibits CD47 signaling may be administered at least about 1 hour to 1 week before administration of the chemotherapeutic agent (for example, at least about 1 hour to 72 hours, about 6 hours to 48 hours, about 12 hours to 36 hours, about 24 hours to 48 hours, about 1 day to 10 days, about 1 day to 7 days, about 2 days to 5 days, or about 3 days to 4 days before administration of the chemotherapeutic agent). In other examples, the agent that inhibits CD47 signaling may be administered to the subject more than about 1 hour, 2 hours, 3 hours, 4 hours, 5 hours, 6 hours, 8 hours, 10 hours, 12 hours, 16 hours, 18 hours, 24 hours, 36 hours, 48 hours, 60 hours, 3 days, 4 days, 5 days, 6 days, 7 days, 8 days, 9 days, or 10 days before administration of the chemotherapeutic agent. In further examples, the agent that inhibits CD47 signaling is administered to the subject no less than about 1 hour, 2 hours, 3 hours, 4 hours, 5 hours, 6 hours, 8 hours, 10 hours, 12 hours, 16 hours, 18 hours, 24 hours, 36 hours, 48 hours, 60 hours, 3 days, 4 days, 5 days, 6 days, 7 days, 8 days, 9 days, or 10 days before administration of the chemotherapeutic agent.

In other examples, the agent that inhibits CD47 signaling is administered to the subject after the chemotherapeutic agent. For example, the agent that inhibits CD47 signaling may be administered at least about 1 hour to 1 week after administration of the chemotherapeutic agent (for example, about 1 hour to 72 hours, about 6 hours to 48 hours, about 12 hours to 36 hours, about 24 hours to 48 hours, about 1 day to 10 days, about 1 day to 7 days, about 2 days to 5 days, or about 3 days to 4 days after administration of the chemotherapeutic agent). In some examples, the agent that inhibits CD47 signaling may be administered to the subject more than about 1 hour, 2 hours, 3 hours, 4 hours, 5 hours, 6 hours, 8 hours, 10 hours, 12 hours, 16 hours, 18 hours, 24 hours, 36 hours, 48 hours, 60 hours, 3 days, 4 days, 5 days, 6 days, 7 days, 8 days, 9 days, or 10 days after administration of the chemotherapeutic agent. In further examples, the agent that inhibits CD47 signaling is administered to the subject no less than about 1 hour, 2 hours, 3 hours, 4 hours, 5 hours, 6 hours, 8 hours, 10 hours, 12 hours, 16 hours, 18 hours, 24 hours, 36 hours, 48 hours, 60 hours, 3 days, 4 days, 5 days, 6 days, or 7 days after administration of the chemotherapeutic agent.

In still further examples, the agent that inhibits CD47 signaling is administered to the subject simultaneously or substantially simultaneously with the chemotherapeutic agent. In a particular example, a chemotherapeutic agent is administered starting immediately after the administration of an agent that inhibits CD47 signaling, for example, no more than 1 hour after administration of the agent that inhibits CD47 signaling (such as no more than 55, 50, 45, 40, 35, 30, 25, 20, 15, 10, or 5 minutes after administration of the agent that inhibits CD47 signaling). In another example, an agent that inhibits CD47 signaling is administered starting immediately after the administration of chemotherapeutic agent, for example, no more than 1 hour after administration of the chemotherapeutic agent (such as no more than 55, 50, 45, 40, 35, 30, 25, 20, 15, 10, or 5 minutes after administration of the chemotherapeutic agent). In further examples, the agent that inhibits CD47 signaling and the chemotherapeutic agent are administered simultaneously, for example at the same time (for example, by the same or different routes of administration) or in the same formulation.

The subject may have cancer which includes a solid tumor, malignant ascites, disseminated cancer, or a hematological malignancy. Examples of solid cancers, such as sarcomas and carcinomas, include but are not limited to fibrosarcoma, myxosarcoma, liposarcoma, chondrosarcoma, osteogenic sarcoma, and other sarcomas, synovioma, mesothelioma, Ewing's tumor, leiomyosarcoma, rhabdomyosarcoma, colon carcinoma, lymphoid malignancy, pancreatic cancer, breast cancer, lung cancers, ovarian cancer, prostate cancer, hepatocellular carcinoma, squamous cell carcinoma, basal cell carcinoma, adenocarcinoma, sweat gland carcinoma, sebaceous gland carcinoma, papillary carcinoma, papillary adenocarcinoma, medullary carcinoma, bronchogenic carcinoma, renal cell carcinoma, hepatoma, bile duct carcinoma, choriocarcinoma, Wilms' tumor, cervical cancer, testicular tumor, bladder carcinoma, and CNS tumors (such as a glioma, astrocytoma, medulloblastoma, craniopharyogioma, ependymoma, pinealoma, hemangioblastoma, acoustic neuroma, oligodendroglioma, menangioma, melanoma, neuroblastoma and retinoblastoma). Examples of hematological cancers include but are not limited to leukemias, including acute leukemias (such as acute lymphocytic leukemia, acute myeloblastic, acute myelogenous leukemia and myeloblastic, promyelocytic, myelomonocytic, monocytic and erythroleukemia), chronic leukemias (such as chronic myelocytic (granulocytic) leukemia, chronic myelogenous leukemia, and chronic lymphocytic leukemia), polycythemia vera, lymphoma, Hodgkin's disease, non-Hodgkin's lymphoma (indolent and high grade forms), multiple myeloma, Waldenstrom's macroglobulinemia, heavy chain disease, myelodysplastic syndrome, and myelodysplasia. In some examples, the subject may have a metastasis of a solid tumor or hematological malignancy, for example, a metastasis to lung, brain, liver, or bone.

In particular examples, the subject with cancer may have breast cancer, lung cancer, ovarian cancer, prostate cancer, thyroid cancer, bladder cancer, stomach cancer, multiple myeloma, soft tissue sarcoma, chronic lymphocytic leukemia, acute lymphocytic leukemia, non-Hodgkin's lymphoma, or a metastasis thereof.

A. Chemotherapeutic Agents

Chemotherapeutic agents of use in the disclosed methods include, but are not limited to alkylating agents, such as nitrogen mustards (for example, chlorambucil, chlormethine, cyclophosphamide, ifosfamide, and melphalan), nitrosoureas (for example, carmustine, fotemustine, lomustine, and streptozocin), platinum compounds (for example, carboplatin, cisplatin, oxaliplatin, and BBR3464), busulfan, dacarbazine, mechlorethamine, procarbazine, temozolomide, thiotepa, and uramustine; antimetabolites, such as folic acid (for example, methotrexate, pemetrexed, and raltitrexed), purines (for example, cladribine, clofarabine, fludarabine, mercaptopurine, and thioguanine), pyrimidines (for example, capecitabine), cytarabine, fluorouracil (e.g., 5-FU), and gemcitabine; plant alkaloids, such as *podophyllum* (for example, etoposide, and teniposide), taxane (for example, docetaxel and paclitaxel), *vinca* (for example, vinblastine, vincristine, vindesine, and vinorelbine); cytotoxic/antitumor antibiotics, such as anthracycline family members (for example, daunorubicin, doxorubicin, epirubicin, idarubicin, mitoxantrone, pirarubicin, vosaroxin, valrubicin, and mitoxantrone), bleomycin, hydroxyurea, geldanamycin, 17-N-allylamino-17-demethoxygeldanamycin (17-AAG), 17-dimethylaminoethylamino-17-demethoxygeldanamycin (17-DMAG), and mitomycin; topoisomerase inhibitors, such as camptothecin, 10-hydroxycamptothecin, irinotecan, SN-38, topotecan, rebeccamycin, or etoposide; monoclonal antibodies, such as alemtuzumab, bevacizumab, brentuximab, cetuximab, ibritumomab, ipilimumab, gemtuzumab, rituximab, ofatumumab, panitumumab, nimotuzumab, tositumomab, and trastuzumab; photosensitizers, such as aminolevulinic acid, methyl aminolevulinate, porfimer sodium, and verteporfin; tyrosine kinase inhibitors, such as afatinib, axitinib, bosutinib, crizotinib, dasatinib, erlotinib, fostamatinib, gefitinib, imatinib, lapatinib, lenvatinib, nilotinib, pazopanib, pegaptianib, sorafenib, sunitinib, and vemurafenib; and other agents, such as alitretinoin, altretamine, amsacrine, anagrelide, arsenic trioxide, asparaginase, bexarotene, bortezomib, celecoxib, denileukin diftitox, estramustine, hydroxycarbamide, pentostatin, masoprocol, mitotane, pegaspargase, and tretinoin. Additional chemotherapeutic agents are listed in Tables 1 and 2 herein. Chemotherapeutic agents can be administered individually, or in combination. Selection and therapeutic dosages of such agents are known to those of ordinary in the art, and can be determined by a skilled clinician.

Chemotherapeutic agents are frequently administered in combination regimens. The disclosed methods include administering an agent that inhibits CD47 signaling with a combination of chemotherapeutic agents. Exemplary chemotherapy combinations include but are not limited to adriamycin (doxorubicin), bleomycin, vinblastine, dacarbazine (ABVD); adriamycin (doxorubicin), cyclophosphamide (AC or CA); cyclophosphamide, adriamycin (doxorubicin), vincristine (CAV); cyclophosphamide, hydroxydaunorubicin (doxorubicin), vincristine (oncovin), prednisone (CHOP); CHOP plus rituximab (CHOP-R); epirubicin, cisplatin, fluorouracil (ECF); etoposide, prednisone, vincristine (oncovin), cyclophosphamide, hydroxydaunorubicin (doxorubicin) (EPOCH); fluorouracil, leucovorin (folinic acid), oxaliplatin (FOLFOX); and ifosfamide, carboplatin, etoposide (ICE). One of ordinary skill in the art can identify other combinations of chemotherapeutic agents of use in the methods disclosed herein.

In particular embodiments of the disclosed methods a subject is administered an agent that inhibits CD47 signaling and a DNA intercalating chemotherapeutic agent (such as an anthracycline). Anthracycline chemotherapeutic agents include anthracycline antibiotic compounds from *Streptomyces peucetius* and derivatives, analogs, or mimetics thereof, including anthracycline-like chemotherapeutic agents. In some examples, an anthracycline chemotherapeutic agent includes one or more of daunorubicin (standard or liposomal formulation), doxorubicin (standard or liposomal formulation), epirubicin, idarubicin, pirarubicin, valrubicin, or derivatives thereof, such as liposomal formulations thereof. In other examples, an anthracycline chemotherapeutic agent includes an anthracycline-like chemotherapeutic agent, such as mitoxantrone or pixantrone or a chemotherapeutic agent targeting topoisomerase-II, such as vosaroxin. In a particular, non-limiting example, the anthracycline chemotherapeutic agent is doxorubicin. Other DNA intercalating chemotherapeutic agents include acridine and psoralen.

In other embodiments of the disclosed methods, a subject is administered an agent that inhibits CD47 signaling and an agent that interferes with DNA synthesis or replication (such as antimetabolite chemotherapeutic agent). Antimetabolite chemotherapeutic agents include purine analogs, pyrimidine analogs, and folate analogs. Purine analog chemotherapeutic agents include fludarabine, mercaptopurine, thioguanine, cladribine, and pentostatin. Pyrimidine analog chemotherapeutic agents include 5-fluorouracil, floxuridine, cytarabine, capecitabine, and gemcitabine. Folate analog chemotherapeutic agents include methotrexate, pemetrexed, raltitrexed, and pralatrexate. In one non-limiting example, the antimetabolite chemotherapeutic agent is 5-fluorouracil.

In additional embodiments of the disclosed methods, a subject is administered an agent that inhibits CD47 signaling and an agent that interferes with DNA replication (such as a topoisomerase inhibitor chemotherapeutic agent). In some examples, the chemotherapeutic agent is a topoisomerase I inhibitor or a topoisomerase II inhibitor. Topoisomerase inhibitor chemotherapeutic agents include camptothecin, 10-hydroxycamptothecin, irinotecan, SN-38, topotecan, rebeccamycin, etoposide, teniposide, amsacirine, ellipicine, and etoposide. In one non-limiting example, the topoisomerase inhibitor chemotherapeutic agent is camptothecin.

In further embodiments of the disclosed methods, a subject is administered an agent that inhibits CD47 signaling and a chemotherapeutic agent that causes oxidative damage to DNA. In some examples, the chemotherapeutic agent is a platinum compound, such as cis-platin, oxaliplatin, or carboplatin. In other examples, the chemotherapeutic agent is geldanamycin or an analog thereof, such as 17-AAG or 17-DMAG.

B. Reduction of Cytotoxicity to Non-Cancer Cells

The disclosed methods reduce or inhibit (or in some examples even prevent) cytotoxicity of chemotherapeutic agents (such as DNA damaging agents) to non-cancer cells. In some embodiments, the methods include administering to a subject with cancer an agent that inhibits CD47 signaling and one or more chemotherapeutic agents, including but not limited to anthracycline, antimetabolite, or topoisomerase inhibitor chemotherapeutics. In additional embodiments, the methods also include detecting a reduction of cytotoxicity of the chemotherapeutic agent to non-cancer cells in the subject. In other embodiments, the methods further include selecting a subject at risk for cytotoxicity of the chemotherapeutic agent, for example, a subject at risk for cardiotoxicity of the chemotherapeutic agent.

In some embodiments, the disclosed methods reduce cytotoxicity of the chemotherapeutic agent to non-cancer cells as compared to a subject or a population of subjects administered the chemotherapeutic agent(s) without an agent that inhibits CD47 signaling. In some examples, administration of an agent that inhibits CD47 signaling and a chemotherapeutic agent may produce fewer or less severe symptoms of cytotoxicity to non-cancer cells than those observed in a subject or population of subjects administered the chemotherapeutic agent without an agent that inhibits CD47 signaling. In other examples, administration of an agent that inhibits CD47 signaling and a chemotherapeutic agent may produce fewer or less severe symptoms of cytotoxicity to non-cancer cells than those observed in the same subject administered the chemotherapeutic agent without an agent that inhibits CD47 signaling. In some examples, the cytotoxicity to non-cancer cells is reduced by at least 10% (such as at least 15%, 20%, 30%, 40%, 50%, 60%, 70%, 80%, 90%, 95%, or 100%) as compared to a control or a subject or population of subjects administered the chemotherapeutic agent without the inhibitor of CD47 signaling.

One major side effect of several widely used chemotherapeutic agents is cardiotoxicity. Although cardiotoxicity is generally associated with anthracycline or anthracycline-like chemotherapeutics, many other chemotherapeutics, including capecitabine, 5-FU, cytarabine, paclitaxel, *vinca* alkaloids, cyclophosphamide, ifosfamide, mitomycin C, tyrosine kinase inhibitors (such as sorafenib, sunitinib, and imatinib), trastuzumab, and bevacizumab, among others, also can result in cardiotoxicity in subjects. In some examples, the cardiotoxicity may be reversible, while in other examples, it may be irreversible.

In some embodiments, administration of an agent that inhibits CD47 signaling and a chemotherapeutic agent to a subject with cancer reduces, inhibits, or even prevents cardiotoxicity in the subject. Cardiotoxicity resulting from chemotherapy treatment includes any toxicity that affects the heart and can include electrophysiological abnormalities (such as ST and T wave changes, T wave flattening, decreased QRS voltage, and/or increased QT interval), cardiac arrhythmias (such as ventricular, supraventricular, or junctional tachycardia; atrial flutter; and/or atrial fibrillation), pericarditis, myocarditis, left ventricular dysfunction, cardiomyopathy, congestive heart failure, ischemia, hypotension or hypertension, cardiogenic shock, and myocardial fibrosis. Administration of an agent that inhibits CD47 signaling and a chemotherapeutic agent (for example, before, during, or after administration of the chemotherapeutic agent) reduces cardiotoxicity of the chemotherapeutic agent. In some examples, administration of an agent that inhibits CD47 signaling and a chemotherapeutic agent reduces signs and symptoms of cardiotoxicity, such as electrophysiological abnormalities, cardiac arrhythmias, left ventricular dysfunction, heart failure, and/or biochemical markers of cardiotoxicity. The disclosed methods may in some embodiments include detecting cardiotoxicity (such as a reduction in cardiotoxicity) in a subject administered an agent that inhibits CD47 signaling and a chemotherapeutic agent.

In some examples, the disclosed methods include selecting a subject at risk for (such as at increased risk for) cardiotoxicity of a chemotherapeutic agent and administering to the selected subject an agent that inhibits CD47 signaling and a chemotherapeutic agent (in either order or concurrently). Risk factors for cardiotoxicity from a chemotherapeutic agent include previous cardiovascular disease and/or hypertension, age, cumulative chemotherapy dose, and dosing schedule. However, risk factors vary to some extent depending upon the type of chemotherapeutic agent. For example, risk factors for anthracycline and anthracycline-like chemotherapeutic agents include cumulative dose of greater than 400 mg/m$^2$ (for example, greater than 550 mg/m$^2$, greater than 700 mg/m$^2$, or greater than 1000 mg/m$^2$), administration of more than 50 mg/m$^2$ dose per day, age of less than 4 years, increasing age, female patient, previous history of cardiovascular disease or hypertension, and mediastinal irradiation (for example pre-treatment with mediastinal irradiation). The main risk factor for cardiotoxicity in subjects treated with alkylating agents (such as cyclophosphamide, ifosfamide, or mitomycin) is dose (for example, greater than about 1.5 g/m$^2$/day for cyclophosphamide or greater than about 20-30 g/m$^2$ cumulative dose for ifosfamide or mitomycin). For 5-FU, the risk factors include high dose (for example greater than 800 mg/m$^2$), continuous infusion administration (rather than bolus administration), history of cardiovascular disease, and previous mediastinal irradiation. One of ordinary skill in the art can identify subjects at increased risk for cardiotoxicity from chemotherapy based on the type of chemotherapy, the subject's prior history, the planned course of treatment, and other factors. Such subjects can be selected for treatment with the disclosed methods in order to reduce cardiotoxicity of a chemotherapeutic agent. See, e.g., Gharib and Burnett, *Eur. J. Heart Failure* 4:235-242, 2002.

Methods for detecting cardiotoxicity of a chemotherapeutic agent (including a reduction in cardiotoxicity) include monitoring cardiac function of a subject before, during, and/or after administration of a chemotherapeutic agent with or without administration of an agent that inhibits CD47 signaling. In some examples, detecting cardiotoxicity includes detecting changes in one or more parameters of an electrocardiogram (ECG), including but not limited to ST and T wave changes, T wave flattening, decreased QRS voltage or prolongation of the QT interval. Detecting normal ECG parameters or an improvement in ECG parameter in the subject (for example in comparison to a control population or in the subject during or after treatment) indicates a reduction of cardiotoxicity. In other examples, detecting cardiotoxicity of a chemotherapeutic agent includes detecting a cardiac arrhythmia in the subject, such as ventricular, supraventricular, or junctional tachycardia, atrial flutter, or atrial fibrillation. Detecting normal cardiac rhythm or an improvement in cardiac rhythm in the subject (for example in comparison to a control population or in the subject during or after treatment) indicates a reduction of cardiotoxicity. In further examples, detecting cardiotoxicity includes measuring left ventricular ejection fraction (LVEF). Detecting a decrease in LVEF (for example in comparison to a control population or in the subject prior to treatment) indicates that cardiotoxicity is present, while maintenance of LVEF or an improvement in LVEF (for example in comparison to a control population or in the subject during or after treatment) indicates a reduction of cardiotoxicity. In additional examples, detecting cardiotoxicity includes measuring one or more biochemical markers of cardiotoxicity in the subject, such as circulating cardiac troponins and/or cardiac natriuretic peptides. Detecting an increase in cardiac troponin I and/or cardiac troponin T in a subject indicates cardiotoxicity, while a decrease in cardiac troponin I and/or cardiac troponin T (for example, in comparison to a population or reference value or in the subject during or after treatment) indicates a reduction in cardiotoxicity. Similarly, detecting an increase in cardiac natriuretic peptides (such as B type natriuretic peptide) in a subject indicates cardiotoxicity, while a decrease in cardiac natriuretic peptides (for example, in comparison to a population or reference value or in the subject during or after treatment) indicates a reduction in cardiotoxicity. See, e.g., Gharib and Burnett, *Eur. J. Heart Failure* 4:235-242, 2002; Dolci et al., *Am. J. Clin. Pathol.* 130:688-695, 2008. In some examples, the cardiotoxicity is reduced by at least 10% (such as at least 15%, 20%, 30%, 40%, 50%, 60%, 70%, 80%, 90%, 95%, or 100%) as compared to a control or a subject or population of subjects administered the chemotherapeutic agent without the inhibitor of CD47 signaling.

Additional cytotoxicities produced by chemotherapeutic agents include myelosuppression (for example, anemia, leukopenia, neutropenia, or thrombocytopenia), alopecia, gastrointestinal distress (such as nausea, vomiting, or diarrhea), and peripheral neuropathy. These cytotoxicities, especially when severe, can limit the aggressiveness of treatment, requiring dose reduction or change in therapy. Thus, in some examples, the methods disclosed herein may also be used to reduce cytotoxicity of chemotherapeutic agents to non-cancer cells, thereby reducing the number, severity, or presence of symptoms of one or more of anemia, leukopenia, neutropenia, thrombocytopenia, alopecia, nausea, vomiting, diarrhea, or peripheral neuropathy. In some examples, the disclosed methods further include detecting myelosuppression (such as a reduction in myelosuppression) in a subject administered an inhibitor of CD47 signaling and a chemotherapeutic agent. Methods for detecting myelosuppression caused by a chemotherapeutic agent (including a reduction in myelosuppression) include monitoring blood cell counts (such as neutrophil counts, platelet counts, red blood cell counts, hematocrit, or hemoglobin). In some examples, the disclosed methods include selecting a subject at risk for (such as at increased risk for) myelosuppression from a chemotherapeutic agent and administering to the selected subject an agent that inhibits CD47 signaling and a chemotherapeutic agent (in either order or concurrently). Risk factors for myelosuppression from a chemotherapeutic agent include age, nutritional status, surgery, cumulative chemotherapy dose, and dosing schedule. Subjects having cancers involving bone marrow (such as leukemias and multiple myeloma) are also at elevated risk for myelosuppression. However, risk factors vary to some extent depending upon the type of chemotherapeutic agent.

In additional examples, the disclosed methods reduce nephrotoxicity of chemotherapeutic agents (for example, nephrotoxicity of cisplatin, carboplatin, ifosfamide, or methotrexate). In some examples, nephrotoxicity is detected by presence of reduced glomerular filtration rate, tubular injury, renal insufficiency, and/or proteinuria. In other examples, the disclosed methods reduce hepatotoxicity of chemotherapeutic agents (for example, hepatotoxicity of 5-FU, floxuridine, irinotecan, oxaliplatin, cisplatin, or methotrexate). Hepatotoxicity may be detected by presence of elevated liver enzymes, elevated bilirubin, steatosis, steatohepatitis, or sinusoidal obstruction syndrome. See, e.g., King and Perry, *Oncologist* 6:162-176, 2001; Jones et al., *Pediatr. Blood Cancer* 51:724-731, 2008. In some embodiments, the disclosed methods further include detecting nephrotoxicity and/or hepatotoxicity (or a reduction thereof) in a subject administered an inhibitor of CD47 signaling and a chemotherapeutic agent.

C. Increasing Cytotoxicity to Cancer Cells

The disclosed methods also increase cytotoxicity of chemotherapeutic agents (such as DNA damaging chemotherapy agents) to cancer cells (e.g., decreasing cancer cell viability, increasing cancer cell death, and/or increasing anti-tumor effects). In some embodiments, the methods include administering to a subject with cancer an agent that inhibits CD47 signaling and one or more chemotherapeutic agents (in either order or concurrently) to increase the cytotoxic effects of the chemotherapeutic agent(s) to cancer cells. In some examples, the cytotoxic effects of the chemotherapeutic agent to cancer cells include decreasing tumor size (for example, tumor volume and/or tumor weight), tumor number (for example, number of primary tumors or number of tumor metastases), occurrence, number, or size of tumor metastases, or tumor recurrence. Cytotoxic effects of the chemotherapeutic agent to cancer cells may also include decreasing number of cancer cells, such as number of solid tumor or hematological cancer cells in the subject. Cytotoxicity to cancer cells and/or anti-tumor effects of the chemotherapeutic agent may also include decreasing the signs and/or symptoms of a tumor or cancer in the subject. An increase in cytotoxicity of the chemotherapeutic agent to cancer cells in the subject may also include increasing survival of the subject (for example, increasing overall survival, recurrence-free survival, and/or metastasis-free survival).

In some embodiments, the disclosed methods increase the cytotoxicity of a chemotherapeutic agent to cancer cells compared to the subject treated with the chemotherapeutic agent alone or compared to a subject or a population of subjects administered the chemotherapeutic agent without an agent that inhibits CD47 signaling. In some examples, administration of an agent that inhibits CD47 signaling and a chemotherapeutic agent decreases tumor size, tumor number, number of cancer cells, occurrence or size of metastases, or tumor recurrence in the subject compared to the same subject prior to treatment or after administration of the chemotherapeutic agent without an agent that inhibits CD47 signaling. In other examples, administration of an agent that inhibits CD47 signaling and a chemotherapeutic agent decreases tumor size, tumor number, number of cancer cells, occurrence of metastases, or tumor recurrence in the subject compared to a subject or population of subjects administered the chemotherapeutic agent without an agent that inhibits CD47 signaling. In some examples, tumor size, tumor number, number of cancer cells, occurrence, size, or number of metastases, or tumor recurrence or number of recurrences is reduced by at least 10% (such as at least 15%, 20%, 30%, 40%, 50%, 60%, 70%, 80%, 90%, 95%, or 100%) as compared to a control or a subject or population of subjects administered the chemotherapeutic agent without the inhibitor of CD47 signaling. In some examples, the methods further include detecting an increase in cytotoxicity of the chemotherapeutic agent to cancer cells as compared to a control, for example by detecting tumor size, tumor number, number of cancer cells, occurrence or size of metastases, or tumor recurrence in a subject administered the chemotherapeutic agent.

In particular non-limiting embodiments, the methods include increasing the cytotoxicity of an anthracycline or anthracycline-like chemotherapeutic agent to cancer cells by administering to a subject with cancer an agent that inhibits CD47 signaling and one or more anthracycline or anthracycline-like chemotherapeutic agents (in either order or concurrently). In particular examples, the anthracycline or anthracycline-like chemotherapeutic agent includes doxorubicin (standard or liposomal formulation), daunorubicin (standard or liposomal formulation), epirubicin, valrubicin, idarubicin, pirarubicin, vosaroxin, or mitoxantrone. In other non-limiting examples, the methods include increasing cytotoxicity of topoisomerase inhibitors (such as camptothecin, 10-hydroxycamptothecin, irinotecan, SN-38, topotecan, rebeccamycin, or etoposide), or antimetabolite agents (such as 5-fluorouracil, gemcitabine, capecitabine, cytrarabine, methotrexate, or pemetrexed) to cancer cells.

IV. Inhibitors of CD47 Signaling

The disclosed methods include inhibiting or blocking CD47 signaling (such as CD47/TSP1 signaling), for example to reduce cytotoxicity of a chemotherapeutic agent to non-cancer cells or to increase anti-tumor effects (e.g., cytotoxicity to cancer cells) of a chemotherapeutic agent. In some examples, the inhibitor of CD47 signaling inhibits TSP1-dependent signaling. In various embodiments, inhibiting CD47 signaling includes one or more of inhibiting the expression of CD47, inhibiting the expression of TSP1, removing endogenous TSP1 or CD47, or blockading or inhibiting the interaction between endogenous TSP1 and CD47.

Agents that block or inhibit CD47 signaling include but are not limited to peptides, antibodies, antisense oligonucleotides, morpholinos, or small molecule inhibitors. The agent that inhibits CD47 signaling includes, in various embodiments, a synthetic peptide having specific binding affinity for CD47; a synthetic peptide having specific binding affinity for TSP1; an oligonucleotide comprising at least about 15 contiguous bases and that hybridizes to the mRNA of CD47 under high stringency conditions; an oligonucleotide comprising at least about 15 contiguous bases and that hybridizes to the mRNA of TSP1 under high stringency conditions; an isolated or recombinant TSP1 or CD47 molecule or soluble fragment thereof, or molecule that binds thereto; an agent that decreases the expression of CD47; an agent that decreases the expression of TSP1; an agent that enhances the proteolysis of CD47; an agent that enhances the proteolysis of TSP1; an agent that enhances removal of CD47 from the cell surface; a CD47 antagonist; an antibody that specifically binds TSP1; an antibody that specifically binds CD47; or a mixture of two or more thereof. Exemplary inhibitors of CD47 signaling include those described in U.S. Pat. No. 8,236,313 and International Pat. Publ. No. WO 2010/017332, both of which are incorporated herein by reference in their entirety.

A. Suppression of Protein Expression

In some embodiments, inhibition or blockade of CD47 signaling is achieved by reducing or suppressing TSP1 or CD47 protein expression, for example in methods of reducing cytotoxicity of a chemotherapeutic agent to non-cancer cells or increasing cytotoxicity of a chemotherapeutic agent to cancer cells, such as exemplified herein.

Although the mechanism by which antisense RNA molecules interfere with gene expression has not been fully elucidated, it is believed that antisense RNA molecules (or fragments thereof) bind to the endogenous mRNA molecules and thereby inhibit translation or splicing of the endogenous mRNA or result in its degradation. A reduction of protein expression in a cell may be obtained by introducing into cells an antisense construct based on TSP1 or CD47 encoding sequences, including the human (or other mammalian) TSP1 cDNA or CD47 cDNA or gene sequence or flanking regions thereof. For antisense suppression, a nucleotide sequence from a TSP1- or CD47-encoding sequence, for example all or a portion of a TSP1 cDNA or gene or all or a portion of a CD47 cDNA or gene, is arranged in reverse orientation relative to the promoter sequence in the transformation vector. One of ordinary skill in the art will understand how other aspects of the vector may be chosen.

The introduced sequence need not be the full length of the cDNA or gene, or reverse complement thereof, and need not be exactly homologous to the equivalent sequence found in the cell type to be transformed. Generally, however, where the introduced sequence is of shorter length, a higher degree of homology to the native target sequence will be needed for effective antisense suppression. The introduced antisense sequence in the vector may be at least 15 nucleotides in length, and improved antisense suppression will typically be observed as the length of the antisense sequence increases. The length of the antisense sequence in the vector advantageously may be greater than about 20 nucleotides, greater than about 30 nucleotides, or greater than about 100 nucleotides. For suppression of the TSP1 gene itself, transcription of an antisense construct results in the production of RNA molecules that are the reverse complement of mRNA molecules transcribed from the endogenous TSP1 gene in the cell. For suppression of the CD47 gene itself, transcription of an antisense construct results in the production of RNA molecules that are the reverse complement of mRNA molecules transcribed from the endogenous CD47 gene in the cell.

Suppression of endogenous TSP1 or CD47 expression can also be achieved using ribozymes. Ribozymes are synthetic molecules that possess highly specific endoribonuclease activity. The production and use of ribozymes are disclosed in U.S. Pat. Nos. 4,987,071 and 5,543,508. The inclusion of ribozyme sequences within antisense RNAs may be used to confer RNA cleaving activity on the antisense RNA, such that endogenous mRNA molecules that bind to the antisense RNA are cleaved, which in turn leads to an enhanced antisense inhibition of endogenous gene expression.

Suppression can also be achieved using RNA interference, using known and previously disclosed methods. Several models have been put forward to explain RNAi, in particular the mechanisms by which the cleavage derived small dsRNAs or siRNAs interact with the target mRNA and thus facilitate its degradation (Hamilton et al., *Science* 286:950, 1999; Zamore et al., *Cell* 101:25, 2000; Hammond et al., *Nature* 404:293, 2000; Yang et al., *Curr. Biol.* 10:1191, 2000; Elbashir et al., *Genes Dev.* 15:188, 2001; *Bass Cell* 101:235, 2000). It has been proposed that the cleavage derived small dsRNAs or siRNAs act as a guide for the enzymatic complex required for the sequence specific cleavage of the target mRNA. Evidence for this includes cleavage of the target mRNA at regular intervals of about 21-23 nucleotides in the region corresponding to the input dsRNA (Zamore et al., *Cell* 101, 25, 2000), with the exact cleavage sites corresponding to the middle of sequences covered by individual 21 or 22 nucleotide small dsRNAs or siRNAs (Elbashir et al., *Genes Dev.* 15:188, 2001). Although mammals and lower organisms appear to share dsRNA-triggered responses that involve a related intermediate (small dsRNAs), it is likely that there will be differences as well as similarities in the underlying mechanism. dsRNAs can be formed from RNA oligomers produced synthetically (for technical details see material from the companies Xeragon and Dharmacon, both available on the internet). Small dsRNAs and siRNAs can also be manufactured using standard methods of in vitro RNA production. In addition, the Silencer™ siRNA Construction kit (and components thereof) available from Ambion (Catalog #1620; Austin, Tex.), which employs a T7 promoter and other well-known genetic engineering techniques to produce dsRNAs. Double stranded RNA triggers could also be expressed from DNA based vector systems.

Inhibition also can be accomplished using stabilized nucleic acid molecules, including morpholino oligonucleotides, for instance as described herein. The stabilized nucleic acid can be delivered directly to cells (for example, in vitro) or can be administered to a subject as herein described. In particular embodiments, the stabilized nucleic acid molecule is an antisense morpholino oligonucleotide complementary to CD47 (such as human and/or murine CD47) or TSP1 (such as human and/or murine TSP1). One non-limiting example is a CD47 morpholino with the nucleic acid sequence CGTCACAGGCAGGACCCACTGCCCA (SEQ ID NO: 3).

The nucleic acids and nucleic acid analogs that are used to suppress endogenous TSP1 or CD47 expression may be modified chemically or biochemically or may contain one or more non-natural or derivatized nucleotide bases, as will be readily appreciated by those of ordinary skill in the art. Such modifications include, for example, labels, methylation, substitution of one or more of the naturally occurring nucleotides with an analog, internucleotide modifications, such as uncharged linkages (for example, methyl phosphonates, phosphotriesters, phosphoramidates, carbamates, etc.), charged linkages (for example, phosphorothioates, phosphorodithioates, etc.), pendent moieties (for example, polypeptides), intercalators (for example, acridine, psoralen, etc.), chelators, alkylators, and/or modified linkages (for example, alpha anomeric nucleic acids, etc.). The term nucleic acid molecule also includes any topological conformation, including single-stranded, double-stranded, partially duplexed, triplexed, hair-pinned, circular and padlocked conformations. Also included are synthetic molecules that mimic polynucleotides in their ability to bind to a designated sequence via hydrogen bonding and other chemical interactions. Such molecules are known in the art and include, for example, those in which peptide linkages substitute for phosphate linkages in the backbone of the molecule.

Additionally, although particular exemplary sequences are disclosed herein, one of ordinary skill in the art will appreciate that the present methods also encompass sequence alterations of the disclosed agents that yield the same results as described herein. Such sequence alterations can include, but are not limited to, deletions, base modifications, mutations, labeling, and insertions.

Suppression of protein expression may also be achieved through agents that enhance proteolysis of CD47 or TSP1 (see, e.g., Allen et al., *Endocrinology* 150:1321-1329, 2009). In other particular examples, the suppression of CD47 expression involves an agent that enhances the removal of CD47 from the cell surface or decreases the transcription, mRNA processing, or translation of CD47. Similar embodiments are envisioned, regarding suppression of TSP1.

B. Suppression of Protein Activity

In some embodiments, inhibition or blockade of CD47 signaling is achieved by reducing or suppressing TSP1 or CD47 protein activity, for example in methods of reducing cytotoxicity of a chemotherapeutic agent to non-cancer cells or increasing cytotoxicity or anti-tumor effects of a chemotherapeutic agent, such as exemplified herein.

In some examples, an inhibitor of CD47 signaling includes an agent that decreases or blocks binding of a ligand (such as TSP1) to CD47. The determination that an agent (such as an antibody or a peptide) inhibits the association between TSP1 and CD47 may be made, for example, using assays known to one of ordinary skill in the art. For instance, the determination that an agent inhibits TSP1 binding to purified or recombinant CD47 can be made by comparing the binding activity alone with the binding activity in the presence of the agent using a solid phase ligand binding assay. An agent that inhibits the activity of TSP1 to signal through CD47 on cells will reduce the activity of a cGMP-dependent reporter in a suitable transfected cell assay by a certain amount, for example, by 20%, 30%, 40%, 50%, 60%, 70%, 80%, 90%, or even by 100%. In addition, an agent that inhibits the activity or CD47 or TSP1 can be identified using any one of the assays described herein, including, but not limited to, determining c-Myc expression in a cell. An agent that inhibits CD47 signaling will increase c-Myc expression (such as an increase in c-Myc mRNA or c-Myc protein) in a cell or population of cells by a certain amount, for example by 20%, 30%, 40%, 50%, 60%, 70%, 80%, 90%, 100%, 150%, 200%, 250%, or more as compared to a suitable control.

Thus, in various embodiments an inhibitor of CD47 signaling includes antibodies (such as monoclonal antibodies or humanized antibodies) that specifically bind to CD47 or TSP1. In some examples, an antibody that specifically binds CD47 is of use in the methods disclosed herein. In other examples, an antibody that specifically binds TSP1 is of use in the methods disclosed herein. Antibodies that specifically bind to CD47 or TSP1 include polyclonal antibodies, monoclonal antibodies, or humanized monoclonal antibodies, or fragments thereof. Methods of constructing such antibodies are known in the art (see, for example, Green et al., "Production of Polyclonal Antisera," in: *Immunochemical Protocols*, pages 1-5, Manson, ed., Humana Press, 1992; Coligan et al., "Production of Polyclonal Antisera in Rabbits, Rats, Mice and Hamsters," in: *Current Protocols in Immunology*, section 2.4.1, 1992; Kohler & Milstein, *Nature* 256:495, 1975; Coligan et al., sections 2.5.1-2.6.7; and Harlow et al. in: *Using Antibodies: a Laboratory Manual*, Cold Spring Harbor Pub., 1998). In addition, such antibodies may be commercially available. In some examples, an inhibitor of CD47 signaling includes an anti-CD47 antibody, such as anti-CD47 antibodies B6H12, BRIC126, 6H9, Clkm1, OVTL16, OX101, or mIAP301 (also referred to as ab301; Chang et al., *Neuroscience* 102:289-296, 2001; BD Biosciences catalog no. 555297), a binding fragment of any one of these, or a humanized version of any one of these, or an antibody or fragment thereof that competes with B6H12, BRIC126, 6H9, Clkm1, OVTL16, OX101, or mIAP301 for binding. In other examples, an inhibitor of CD47 signaling includes an anti-TSP1 antibody, such as C6.7 (Dixit et al., *Proc. Natl. Acad. Sci. USA* 82:3472-3476, 1985; Pierce catalog no. MA5-13390), HB8432, D4.6, A65M, A4.1, A6.1, or SPM321, a binding fragment of any one of these, or a humanized version of any one of these, or an antibody or fragment thereof that competes with C6.7, HB8432, D4.6, A65M, A4.1, A6.1 (e.g., Millipore catalog no. BA24), or SPM321 for binding. It is to be understood that CD47 signaling inhibitors for use in the present disclosure also include novel CD47 or TSP1 antibodies developed in the future.

In other embodiments, an inhibitor of CD47 signaling includes a peptide that specifically binds to CD47 or TSP1. In some examples an inhibitor of CD47 signaling is a CD47-binding peptide, such as a TSP1-derived CD47-binding peptide. Exemplary CD47-binding peptides include 7N3 (FIRVVMYEGKK; SEQ ID NO: 1) and 4N1 (also known as 459; RFYVVMWK; SEQ ID NO: 2). Additional CD47-binding peptides include those described in U.S. Pat. No. 8,236,313, incorporated herein by reference in its entirety. It is to be understood that CD47 signaling inhibitors for use in the present disclosure also include novel CD47 or TSP1 binding peptides developed in the future.

In additional embodiments, an inhibitor of CD47 signaling includes a small molecule (such as a small organic molecule). Some small molecule inhibitors may inhibit CD47 or TSP1 expression or activity. It is to be understood that CD47 signaling inhibitors for use in the present disclosure also include novel CD47 or TSP1 small molecule inhibitors developed in the future.

C. Pharmaceutical Compositions

Pharmaceutical compositions that include at least one inhibitor of CD47 signaling as described herein as an active ingredient, or that include both an agent that inhibits CD47 signaling and an additional agent (such as a chemotherapeutic agent) as active ingredients, may be formulated with an appropriate solid or liquid carrier, depending upon the particular mode of administration chosen.

A suitable administration format may best be determined by a medical practitioner for each subject individually. Various pharmaceutically acceptable carriers and their formulation are described in standard formulation treatises, for example, *Remington: The Science and Practice of Pharmacy*, The University of the Sciences in Philadelphia, Editor, Lippincott, Williams, & Wilkins, Philadelphia, Pa., 21$^{st}$ Edition (2005). See also Wang and Hanson, *J. Parenteral Sci. Technol.*, Technical Report No. 10, Supp. 42: 2S, 1988.

The dosage form of the pharmaceutical composition will be determined by the mode of administration chosen. For instance, in addition to injectable fluids, inhalational, topical, ophthalmic, peritoneal, and oral formulations can be employed. Inhalational preparations can include aerosols, particulates, and the like. In general, the goal for particle size for inhalation is about 1 µm or less in order that the pharmaceutical reach the alveolar region of the lung for absorption. Oral formulations may be liquid (for example, syrups, solutions, or suspensions), or solid (for example, powders, pills, tablets, or capsules). For solid compositions, conventional non-toxic solid carriers can include pharmaceutical grades of mannitol, lactose, starch, or magnesium stearate. Actual methods of preparing such dosage forms are known, or will be apparent, to those of ordinary skill in the art.

The compositions or pharmaceutical compositions can be administered by any route, including parenteral administration, for example, intravenous, intramuscular, intraperitoneal, intrasternal, or intra-articular injection or infusion, or by transdermal, sublingual, oral, topical, intra-nasal, ophthalmic, or transmucosal administration, or by pulmonary inhalation. When the active compounds are provided as parenteral compositions, for example, for injection or infusion, they are generally suspended in an aqueous carrier, for example, in an isotonic buffer solution at a pH of about 3.0 to about 8.0, preferably at a pH of about 3.5 to about 7.4, 3.5 to 6.0, or 3.5 to about 5.0. Useful buffers include sodium citrate-citric acid and sodium phosphate-phosphoric acid, and sodium acetate/acetic acid buffers. A form of repository or depot slow release preparation may be used so that therapeutically effective amounts of the preparation are delivered into the bloodstream over many hours or days following transdermal injection or delivery.

Active compounds (e.g., peptides, proteins, oligonucleotides, and so forth) are also suitably administered by sustained-release systems. Suitable examples of sustained-release formulations include suitable polymeric materials (such as, for example, semi-permeable polymer matrices in the form of shaped articles, for example, films, or microcapsules), suitable hydrophobic materials (for example as an emulsion in an acceptable oil) or ion exchange resins, and sparingly soluble derivatives (such as, for example, a sparingly soluble salt). Sustained-release compounds may be administered by intravascular, intravenous, intra-arterial, intramuscular, subcutaneous, intra-pericardial, or intra-coronary injection. Administration can also be oral, rectal, parenteral, intracisternal, intravaginal, intraperitoneal, topical (as by powders, ointments, gels, drops or transdermal patch), buccal, or as an oral or nasal spray.

Preparations for administration can be suitably formulated to give controlled release of the agent(s) (e.g., peptides, antibodies, oligonucleotides or other compounds that block CD47 and/or TSP1 activity or interaction). For example, the pharmaceutical compositions may be in the form of particles comprising a biodegradable polymer and/or a polysaccharide jellifying and/or bioadhesive polymer, an amphiphilic polymer, an agent modifying the interface properties of the particles and a pharmacologically active substance. These compositions exhibit certain biocompatibility features that allow a controlled release of the active substance. See, for example, U.S. Pat. No. 5,700,486.

In some embodiments, therapeutic agent(s) are delivered by way of a pump (see Sefton, *CRC Crit. Ref. Biomed. Eng.* 14:201, 1987; Buchwald et al., *Surgery* 88:507, 1980; Saudek et al., *N. Engl. J. Med.* 321:574, 1989) or by continuous subcutaneous infusions, for example, using a mini-pump. An intravenous bag solution may also be employed. The key factor in selecting an appropriate dose is the result obtained, as measured by increases or decreases in radioprotection, or by other criteria for measuring control or prevention of disease, as are deemed appropriate by the practitioner. Other controlled release systems are discussed in Langer (*Science* 249:1527-1533, 1990).

In another aspect of the disclosure, therapeutic agent(s) are delivered by way of an implanted pump, described, for example, in U.S. Pat. Nos. 6,436,091; 5,939,380; and 5,993,414. Implantable drug infusion devices are used to provide subjects with a constant and long term dosage or infusion of a drug or any other therapeutic agent. Essentially, such device may be categorized as either active or passive.

Active drug or programmable infusion devices feature a pump or a metering system to deliver the drug into the patient's system. An example of such an active drug infusion device currently available is the Medtronic SynchroMed™ programmable pump. Such pumps typically include a drug reservoir, a peristaltic pump to pump the drug out from the reservoir, and a catheter port to transport the pumped out drug from the reservoir via the pump to a patient's anatomy. Such devices also typically include a battery to power the pump, as well as an electronic module to control the flow rate of the pump. The Medtronic SynchroMed™ pump further includes an antenna to permit the remote programming of the pump.

Passive drug infusion devices, in contrast, do not feature a pump, but rather rely upon a pressurized drug reservoir to deliver the drug. Thus, such devices tend to be both smaller as well as cheaper as compared to active devices. An example of such a device includes the Medtronic IsoMed™ infusion system. This device delivers the drug into the patient through the force provided by a pressurized reservoir applied across a flow control unit.

The implanted pump can be completely implanted under the skin of a subject, thereby negating the need for a percutaneous catheter. These implanted pumps can provide the patient with therapeutic agent(s) at a constant or a programmed delivery rate. Constant rate or programmable rate pumps are based on either phase-change or peristaltic technology. When a constant, unchanging delivery rate is required, a constant-rate pump is well suited for long-term implanted drug delivery. If changes to the infusion rate are expected, a programmable pump may be used in place of the constant rate pump system. Osmotic pumps may be much smaller than other constant rate or programmable pumps, because their infusion rate can be very low. An example of such a pump is described listed in U.S. Pat. No. 5,728,396.

The therapeutic agents may also be delivered passively and in sustained fashion as part of and incorporated into implantable devices, such as vascular stents which can be placed directly into diseased blood vessels through several standard approaches, including direct surgical insertion or percutaneously with angiographic control.

For oral administration, the pharmaceutical compositions can take the form of, for example, tablets or capsules prepared by conventional means with pharmaceutically acceptable excipients such as binding agents (for example, pre-gelatinized maize starch, polyvinylpyrrolidone or hydroxypropyl methylcellulose); fillers (for example, lactose, microcrystalline cellulose or calcium hydrogen phosphate); lubricants (for example, magnesium stearate, talc or silica); disintegrants (for example, potato starch or sodium starch glycolate); or wetting agents (for example, sodium lauryl sulfate). The tablets can be coated by methods well known in the art. Liquid preparations for oral administration can take the form of, for example, solutions, syrups or suspensions, or they can be presented as a dry product for constitution with water or other suitable vehicle before use. Such liquid preparations can be prepared by conventional means with pharmaceutically acceptable additives such as suspending agents (for example, sorbitol syrup, cellulose derivatives or hydrogenated edible fats); emulsifying agents (for example, lecithin or *acacia*); non-aqueous vehicles (for example, almond oil, oily esters, ethyl alcohol or fractionated vegetable oils); and preservatives (for example, methyl or propyl-p-hydroxybenzoates or sorbic acid). The preparations can also contain buffer salts, flavoring, coloring, and sweetening agents as appropriate.

For administration by inhalation, the compounds for use according to the present disclosure are conveniently delivered in the form of an aerosol spray presentation from pressurized packs or a nebulizer, with the use of a suitable propellant, for example, dichlorodifluoromethane, trichlorofluoromethane, dichlorotetrafluoroethane, carbon dioxide or other suitable gas. In the case of a pressurized aerosol, the dosage unit can be determined by providing a valve to deliver a metered amount. Capsules and cartridges for use in an inhaler or insufflator can be formulated containing a powder mix of the compound and a suitable powder base such as lactose or starch.

For topical administration, the compounds can be, for example, mixed with a liquid delivery agent for administration locally. The agents used therapeutically (such as peptides, antibodies and morpholinos) are readily soluble or suspendable in water and saline, and as such these would be useful for delivery since water or saline do not cause adverse biological tissue effects. This allows sufficiently high doses to be administered locally or systemically, without secondary toxicity from the delivery vehicle.

Pharmaceutical compositions that comprise at least one therapeutic agent (such as an inhibitor of CD47 signaling) as described herein as an active ingredient will normally be formulated with an appropriate solid or liquid carrier, depending upon the particular mode of administration chosen. The pharmaceutically acceptable carriers and excipients useful in this disclosure are conventional. For instance, parenteral formulations usually comprise injectable fluids that are pharmaceutically and physiologically acceptable fluid vehicles such as water, physiological saline, other balanced salt solutions, aqueous dextrose, glycerol or the like. Excipients that can be included are, for instance, proteins, such as human serum albumin or plasma preparations. If desired, the pharmaceutical composition to be administered may also contain minor amounts of non-toxic auxiliary substances, such as wetting or emulsifying agents, preservatives, and pH buffering agents and the like, for example sodium acetate or sorbitan monolaurate. Actual methods of preparing such dosage forms are known, or will be apparent, to those skilled in the art.

For example, for parenteral administration, agent(s) can be formulated generally by mixing them at the desired degree of purity, in a unit dosage injectable form (solution, suspension, or emulsion), with a pharmaceutically acceptable carrier, for instance, one that is non-toxic to recipients at the dosages and concentrations employed and is compatible with other ingredients of the formulation. A pharmaceutically acceptable carrier is a non-toxic solid, semisolid or liquid filler, diluent, encapsulating material or formulation auxiliary of any type.

Generally, the formulations are prepared by contacting the agent(s) each uniformly and intimately with liquid carriers or finely divided solid carriers or both. Then, if necessary, the product is shaped into the desired formulation. Optionally, the carrier is a parenteral carrier, and in some embodiments it is a solution that is isotonic with the blood of the recipient. Examples of such carrier vehicles include water, saline, Ringer's solution, and dextrose solution. Non-aqueous vehicles such as fixed oils and ethyl oleate are also useful herein, as well as liposomes.

The pharmaceutical compositions that comprise at least one therapeutic agent, in some embodiments, will be formulated in unit dosage form, suitable for individual administration of precise dosages. The amount of active compound(s) administered will be dependent on the subject being treated, the severity of the affliction, and the manner of administration, and is best left to the judgment of the prescribing clinician. Within these bounds, the formulation to be administered will contain a quantity of the active component(s) in amounts effective to achieve the desired effect in the subject being treated. The therapeutically effective amount of an agent that inhibits CD47 signaling, such as a peptide, antibody, or oligonucleotide (e.g., morpholino or other antisense molecule) will be dependent on the peptide or inhibitor utilized, the subject being treated, the severity and type of the affliction, and the manner of administration. The exact dose is readily determined by one of skill in the art based on the potency of the specific compound, the age, weight, sex and physiological condition of the subject.

The peptides/proteins of the present disclosure (for example, CD47 or TSP1 peptides, or a peptide that inhibits or alters binding between TSP1 and CD47, including a peptide from an antibody or an artificial antibody with this functional characteristic, or a peptide or protein that inhibits the expression or activity of either of these proteins) also can be administered as naked DNA encoding the peptide or protein. To simplify the manipulation and handling of the nucleic acid encoding the peptide, the nucleic acid is generally inserted into a cassette, where it is operably linked to a promoter. Preferably, the promoter is capable of driving expression of the protein in cells of the desired target tissue. The selection of appropriate promoters can readily be accomplished. Preferably, the promoter is a high expression promoter, for example the 763-base-pair cytomegalovirus (CMV) promoter, the Rous sarcoma virus (RSV) promoter (Davis et al., *Hum. Gene. Ther.* 4:151-159, 1993), or the MMT promoter.

Other elements that enhance expression also can be included, such as an enhancer or a system that results in high levels of expression, such as a tat gene or tar element. This cassette is inserted into a vector, for example, a plasmid vector such as pUC118, pBR322, or other known plasmid vector, that includes, for example, an *E. coli* origin of replication. See, Sambrook, et al., *Molecular Cloning: A Laboratory Manual*, Cold Spring Harbor Laboratory Press (1989). The plasmid vector may also include a selectable marker such as the β-lactamase gene for ampicillin resistance, provided that the marker polypeptide does not adversely affect the metabolism of the organism being treated. The cassette also can be bound to a nucleic acid binding moiety in a synthetic delivery system, such as the system disclosed in PCT publication WO 95/22618.

Optionally, the DNA may be used with a microdelivery vehicle such as cationic liposomes and adenoviral vectors. (For a review of the procedures for liposome preparation, targeting and delivery of contents, see Mannino and Gould-Fogerite, *BioTechniques*, 6:682, 1988); Feigner and Holm, *Bethesda Res. Lab. Focus*, 11(2):21, 1989); and Maurer, *Bethesda Res. Lab. Focus*, 11(2):25, 1989). Replication-defective recombinant adenoviral vectors can be produced in accordance with known techniques. (See Quantin, et al., *Proc. Natl. Acad. Sci. USA*, 89:2581-2584, 1992; Stratford-Perricadet, et al., *J. Clin. Invest.*, 90:626-630, 1992; and Rosenfeld, et al., *Cell*, 68:143-155, 1992).

The effective dose of the nucleic acid will be a function of the particular expressed protein, the target tissue, the subject, and his or her clinical condition. Effective amounts of DNA are between about 1 and 4000 µg, or about 1000 and 2000 µg, or between about 2000 and 4000 µg. In certain situations, it is desirable to use nucleic acids encoding two or more different proteins in order to optimize the therapeutic outcome. For example, DNA encoding a therapeutic peptide, such as a CD47 or TSP1 peptide (for example, peptide p7N3 FIRVVMYEGKK (SEQ ID NO: 1) or peptide 4N1): RFYVVMWK (SEQ ID NO: 2)) can be used. Alternatively, DNA encoding a CD47 or TSP1 peptide can be combined with other genes or their encoded gene products to enhance the activity of targeted cells.

In order to facilitate injection, the nucleic acid is formulated with a pharmaceutically acceptable carrier. Examples of suitable carriers include, but are not limited to, saline, albumin, dextrose and sterile water. The nucleic acid is injected into the ischemic tissue using standard injection techniques by use of, for example, a hypodermic needle, for example a hypodermic needle size between No. 29 and No. 16. The nucleic acid also may be injected by an externally applied local injection apparatus, such as that used to inject antigens for allergy testing; or a transcutaneous patch capable of delivery to subcutaneous muscle. The nucleic acid is injected at one site, or at multiple sites throughout the ischemic tissue.

Once injected, the nucleic acid capable of expressing the desired protein or peptide is taken up and expressed by the cells of the tissue. Because the vectors containing the nucleic acid of interest are not normally incorporated into the genome of the cells, expression of the protein of interest takes place for only a limited time. Typically, the peptide or protein is only expressed at therapeutic levels for about two days to several weeks, preferably for about one to two weeks. Reinjection of the DNA can be utilized to provide additional periods of expression of the peptide or protein. If desired, use of a retrovirus vector to incorporate the heterologous DNA into the genome of the cells will increase the length of time during which the therapeutic polypeptide is expressed, from several weeks to indefinitely.

The therapeutic agents can also be administered directly as part of a surgical or other medical procedure, or at the bedside by a treating physician. Drug quality product (e.g., peptide, antibody or morpholino) can be diluted for instance in sterile saline and given by injection using sterile 1 cc syringes and small bore needles (25 gauge and less) to a subject in need of treatment. Precise control and localization of therapeutic effects can thus be obtained.

Controlled release parenteral formulations can be made as implants, oily injections, or as particulate systems. For a broad overview of protein delivery systems, see Banga, *Therapeutic Peptides and Proteins: Formulation, Processing, and Delivery Systems*, Technomic Publishing Company, Inc., Lancaster, Pa., 1995. Particulate systems include microspheres, microparticles, microcapsules, nanocapsules, nanospheres, and nanoparticles. Microcapsules contain the therapeutic peptide as a central core. In microspheres, the therapeutic agent is dispersed throughout the particle. Particles, microspheres, and microcapsules smaller than about 1 µm are generally referred to as nanoparticles, nanospheres, and nanocapsules, respectively. Capillaries have a diameter of approximately 5 µm so that only nanoparticles are administered intravenously. Microparticles are typically around 100 µm in diameter and are administered subcutaneously or intramuscularly (see Kreuter, *Colloidal Drug Delivery Systems*, J. Kreuter, ed., Marcel Dekker, Inc., New York, N.Y., pp. 219-342, 1994; Tice & Tabibi, *Treatise on Controlled Drug Delivery*, A. Kydonieus, ed., Marcel Dekker, Inc. New York, N.Y., pp. 315-339, 1992).

Also contemplated is the use of nanoparticles as delivery agents, which can be targeted to specific cells, tissues or organ for instance by incorporation on their surface ligands of receptors specific in their expression to the targeted cells, tissues or organs, The targeting entity can be the same or different than the therapeutically active agent carried by the nanoparticle. Further, distribution of nanoparticles to certain tissues spaces (e.g. the blood versus the central nervous system protected by the blood-brain barrier) can be determined by altering the size of the nanoparticles thereby allowing or preventing their transit of such barriers between tissue compartments.

Polymers can be used for ion-controlled release. Various degradable and nondegradable polymeric matrices for use in controlled drug delivery are known in the art (Langer, *Accounts Chem. Res.* 26:537, 1993). For example, the block copolymer, polaxamer 407 exists as a viscous yet mobile liquid at low temperatures but forms a semisolid gel at body temperature. It has shown to be an effective vehicle for formulation and sustained delivery of recombinant interleukin-2 and urease (Johnston et al., *Pharm. Res.* 9:425, 1992; Pec, *J. Parent. Sci. Tech.* 44(2):58, 1990). Alternatively, hydroxyapatite has been used as a microcarrier for controlled release of proteins (Ijntema et al., *Int. J. Pharm.* 112:215, 1994). In yet another aspect, liposomes are used for controlled release as well as drug targeting of lipid-capsulated compounds (Betageri et al., *Liposome Drug Delivery Systems*, Technomic Publishing Co., Inc., Lancaster, Pa., 1993). Numerous additional systems for controlled delivery of therapeutic proteins are known (e.g., U.S. Pat. Nos. 5,055,303; 5,188,837; 4,235,871; 4,501,728; 4,837,028; 4,957,735; and 5,019,369; 5,055,303; 5,514,670; 5,413,797; 5,268,164; 5,004,697; 4,902,505; 5,506,206; 5,271,961; 5,254,342; and 5,534,496).

The specific form of the agents and their manner of administration depends in part upon the particular tissue to be treated. The compounds or pharmaceutical compositions containing them can be applied, for example, as a mouthwash to coat the oral mucosal tissue, as a spray or syringe to coat the mucosal tissues of the nose and/or throat, or as a cream or paste, an enema, or other forms of topical administration known to one of ordinary skill in the art, as appropriate.

The amount of agent to be delivered, as well as the dosing schedule necessary to provide the desired effects, will be influenced by the bioavailability of the specific compound selected (and/or an active metabolite thereof), the type and extent of chemotherapeutic dosage and schedule, and other factors that will be apparent to those of skill in the art. The same dosage and concentrations can be used when the agent that inhibits CD47 signaling is administered after chemotherapeutic treatment. The administration (e.g., before, during, or after chemotherapy treatment) may be used alone, or in any combination of two or all three administrations, as needed.

V. Kits

Also disclosed herein are kits that can be used to reduce cytotoxicity of a chemotherapeutic agent to non-cancer cells and/or to increase anti-tumor effects of a chemotherapeutic agent. In some embodiments, the kit includes one or more agent that blocks CD47 signaling (such as one or more of an anti-CD47 antibody or fragment thereof, a CD47-binding peptide, a CD47 antisense oligonucleotide, a CD47 morpholino, an anti-TSP1 antibody or fragment thereof, a TSP1-binding peptide, a TSP1 antisense oligonucleotide, or a TSP1 morpholino) and a chemotherapeutic agent (such as an anthracycline chemotherapeutic agent). In other embodiments, the kit includes a small molecule capable of binding to CD47 or a small molecule capable of binding to TSP1 and a chemotherapeutic agent.

In one example, the kit includes a CD47 morpholino, such as a morpholino including the sequence of SEQ ID NO: 3 and a chemotherapeutic agent (such as an anthracycline chemotherapeutic agent, for example, daunorubicin or doxorubicin). In another example, the kit includes an anti-CD47 antibody or fragment thereof (such as monoclonal antibody MIAP301, monoclonal antibody OX101, monoclonal antibody B6H12, or monoclonal antibody BRIC126) and a chemotherapeutic agent (such as an anthracycline chemotherapeutic agent, for example, daunorubicin or doxorubicin). In a further example, the kit includes a CD47 binding peptide (such as a peptide including the amino acid sequence of SEQ ID NO: 1 or SEQ ID NO: 2) and a chemotherapeutic agent (such as an anthracycline chemotherapeutic agent, for example, daunorubicin or doxorubicin). In another example, the kit includes an anti-TSP1 antibody or fragment thereof (such as monoclonal antibody A6.1 or monoclonal antibody C6.7) and a chemotherapeutic agent (such as an anthracycline chemotherapeutic agent, for example, daunorubicin or doxorubicin).

The kits may further include additional components such as instructional materials and additional reagents, for example buffers or pharmaceutically acceptable carriers. The instructional materials may be written, in an electronic form (such as a computer diskette or compact disk), or may be visual (such as video files).

The following examples are provided to illustrate certain particular features and/or embodiments. These examples should not be construed to limit the disclosure to the particular features or embodiments described.

Example 1

Blockade of CD47 Sensitizes Breast Tumors to Anthracycline Chemotherapy and Protects Cardiovascular Tissue Materials and Methods Cell Culture:

4T1 mouse breast cancer cells or MDA-MB-231 human breast cancer cells were cultured in RPMI 1640 medium supplemented with 10% FBS, penicillin/streptomycin, and glutamine at 37° C. and 5% $CO_2$. For treatment with anthracycline, doxorubicin was used at 10 μg/mL. CD47 morpholino was used to block CD47 expression at a 10 μM dose.

Mouse Model:

Balb/c mice were injected with $5 \times 10^3$ 4 T1 breast cancer cells in the mammary fat pad. Tumors were left untreated, treated with 100 μl of 10 μg/mL doxorubicin (Dox) or with 10 μg/mL Dox in combination with 10 μM CD47 Morpholino (CD47 M). Doxorubicin treatment was given intravenously weekly. Treatment with CD47 M was given intraperitoneally 48 hours prior to doxorubicin injection.

Cell Survival:

Cell viability was measured by 3-(4,5-dimethylthiazol-2-yl)-5-(3-carboxymethoxyphenyl)-2-(4-sulfophenyl)-2H-tetrazolium (MTS) assay or lactate dehydrogenase (LDH) release and cell death by terminal deoxynucleotidyl transferase dUTP nick end labeling (TUNEL). LDH release was quantified in cell culture supernatant using the CytoTox 960 Non-Radioactive Cytotoxicity Assay following manufacturer's instructions (Promega, Catalog No. G1780).

Immunohistochemistry:

Staining of tissue sections was performed as previously shown (Soto-Pantoja et al., *Autophagy* 8:1628-1642, 2012; Soto-Pantoja et al., *Sci. Rep.* 3:1038, 2013). Briefly, slides were deparaffinized in xylene and rehydrated in graded alcohol. Antigen retrieval was performed using microwave antigen retrieval method with Target Retrieval Solution, pH 6.1 (Dako, Carpinteria, Calif.). Endogenous peroxidase activity was quenched by 0.3% $H_2O_2$ in water. Slides were incubated with respective antibodies. Sections were treated with streptavidin-biotin and DAB (3,3-diaminobenzidine)

was used as chromogen. Hematoxylin was used for counterstaining. The intensity of the staining was evaluated under light microscopy.

PCR:

Total RNA was isolated using TRIZOL® reagent (Life Technologies, Carlsbad, Calif.), following the manufacturer's instructions. For each analysis, 5 µg of RNA was reverse-transcribed using the SUPERSCRIPT® III first strand synthesis kit (Life Technologies). Quantitative realtime PCR was performed using SYBR® Green on an MJ Research OPTICON® I instrument. The results were quantified as Ct values, where Ct is defined as the threshold cycle of PCR at which the amplified product is first detected and expressed as fold gene expression (the ratio of target/control).

Measurement of Oxygen Consumption Rate (OCR) and Extracellular Acidification Rate (ECAR):

4T1 breast cancer cells or B16 melanoma cells ($2\times10^4$ cells) were plated in the presence or absence of CD47 morpholino (10 µM). After a 48 hour period of incubation, cells were treated with doxorubicin for 1 hour (10 µg/ml). OCR and ECAR were measured using an XF24 analyzer (Seahorse Bioscience, N. Billerica, Mass.).

Cell Viability:

Wild type or CD47 null Jurkat T cells were plated at a density of $7\times10^3$/well in 96 well plates or 500 cells/well in 1536 well plates. Cells were treated with increasing amounts of doxorubicin. Cell viability was measured 48 or 72 hours after treatment by MTS reduction or using CellTiter-Glo® cell viability assay (Promega, Madison Wis.).

Results

Blockade of CD47 Sensitizes Breast Tumors to Anthracycline Chemotherapy:

4T1B breast cancer cells were implanted in the mammary fat-pad of Balb/C mice. The mice were treated weekly with saline, doxorubicin, CD47 M, or the combination of CD47 M with doxorubicin. Tumor growth was measured using calipers and was followed for 30 days. Treatment with CD47 morpholino was done two days prior to each treatment with doxorubicin for four weeks. The tumors in the saline control mice demonstrated rapid tumor growth while treatment with doxorubicin or CD47 morpholino alone slightly delayed tumor growth (FIG. 1A). In contrast, orthotopic tumors treated with the CD47 morpholino followed by doxorubicin treatment exhibited dramatically delayed tumor growth relative to doxorubicin or CD47 morpholino alone (FIG. 1A). These data indicate that blockade of CD47 enhances doxorubicin therapy to reduce tumor growth.

Figure 1B:
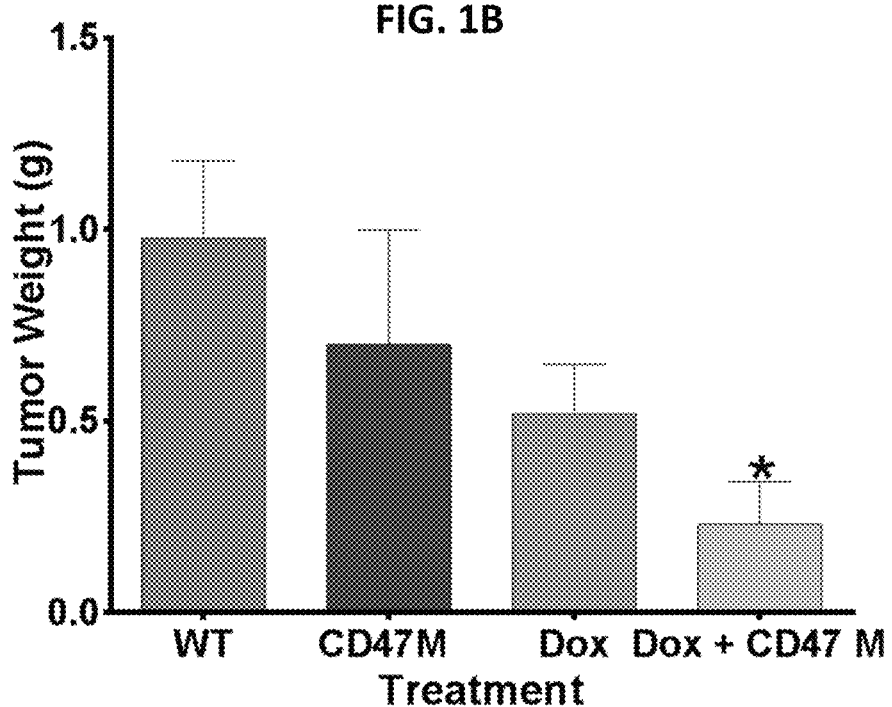
FIG. 1B is a graph showing the weight of the tumors in FIG. 1A at the end of the study. *, p<0.05, n=5 per group.

Tumors were excised at the end of the study and weighed. Tumors of mice treated with saline tripled in size (FIG. 1B). On the other hand, even though doxorubicin or CD47 morpholino treatment caused a reduction in tumor weight, combination of CD47 blockade and doxorubicin further reduced tumor mass by 50% or more (FIG. 1B). Thus blockade CD47 enhances the reduction of breast tumor growth by doxorubicin in a syngeneic tumor model, indicating that CD47 potentiates anthracycline-mediated breast tumor therapy.

Figure 12A:
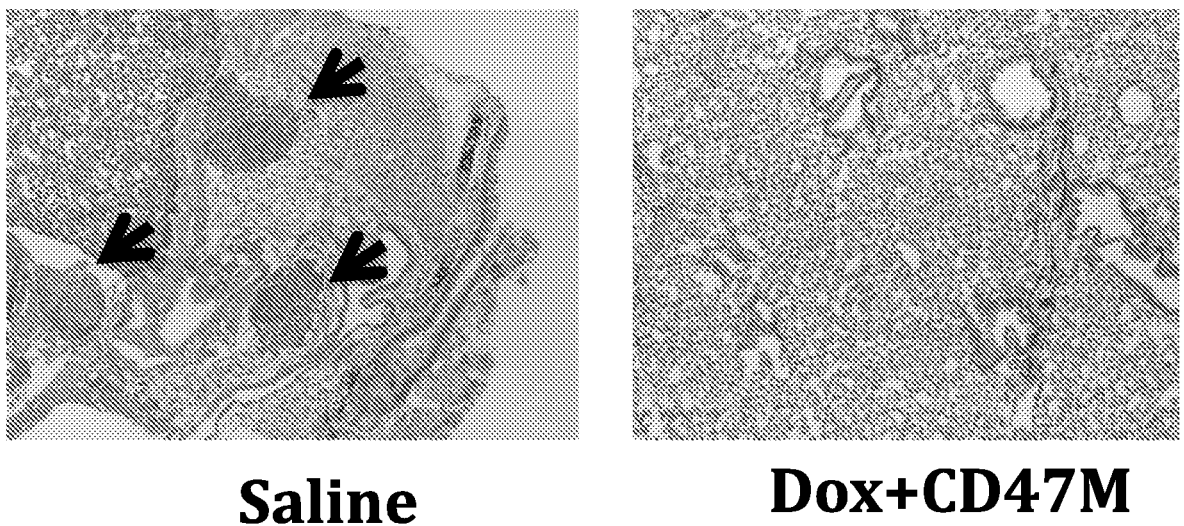
FIG. 12A is a pair of digital images of representative hematoxylin and eosin stained lung tissue from mice injected with 4T1 breast cancer cells in the mammary fat pad and treated with saline (left) or doxorubicin and CD47 morpholino (right). The saline-treated animal had metastases in the lung (arrows), while the animal treated with doxorubicin plus CD47 M had no lung metastases.
Figure 12B:
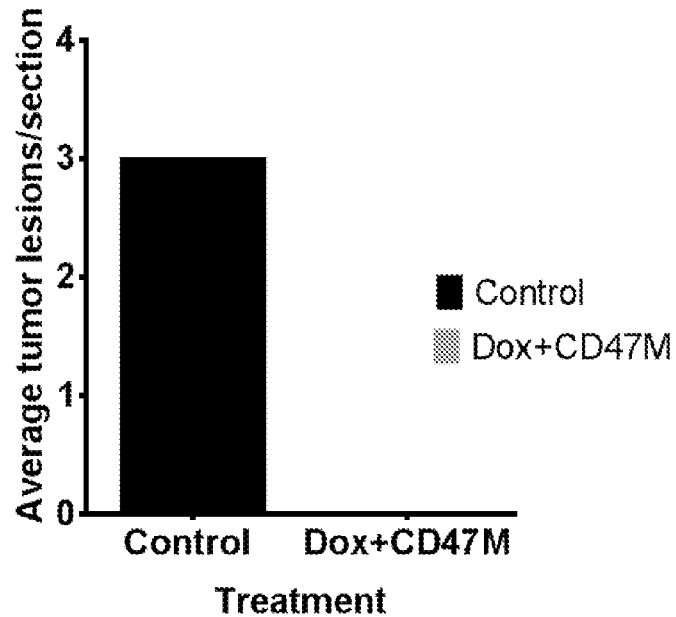
FIG. 12B is a graph showing average number of tumor lesions per lung section in mice injected with 4T1 breast cancer cells in the mammary fat pad and treated with saline (control) or doxorubicin and CD47 morpholino (Dox+CD47M).

Blockade of CD47 in Combination with Doxorubicin Reduces Metastasis:

The 4T1 breast cancer model is a well known model for metastasis of orthotopic breast tumors to lung and other organs. Mice were injected in the mammary fat pad with 4T1 cells. CD47 morpholino was administered intraperitoneally at a dose of 10 µM per mouse. Doxorubicin was adminstered intravenously at a dose of 10 mg/kg. The CD47 morpholino was administered weekly and the Doxorubicin administration was done weekly 48 hours after CD47 treatment. Five mice per group were treated. Lungs were exised, paraffin embedded, and hematoxylin and eosin stain was used to determine tissue structure. Mice treated with saline showed formation of tumors in the lung indicating that cells injected in the mammary fatpad metastazised to lung (FIG. 12A, left panel). On the other hand, combination of Dox and CD47 M completely reduced metastasis to lung (FIG. 12A, right panel). No metastases were observed in lungs from mice treated with Dox and CD47 M (FIG. 12B). This indicates that the combination treatment reduces metastasis to reduce tumor burden.

Blockade of CD47 Regulates Oxygen Consumption Rate and Extracellular Acidification Rate in 4T1 Breast Cancer Cells.

Figure 2A:
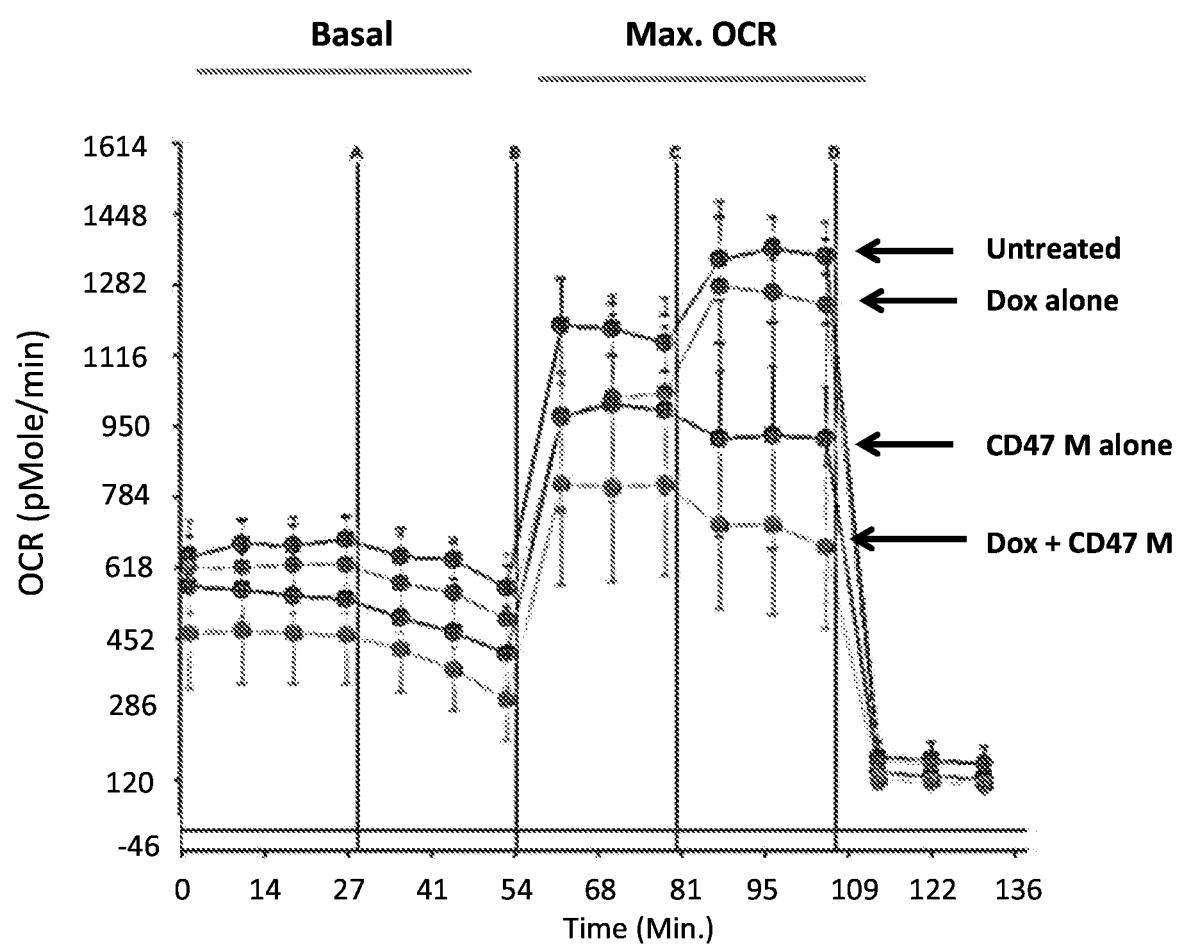
FIG. 2A is a graph showing oxygen consumption rate (OCR) in 4T1 breast cancer cells untreated or treated with 10 µM CD47 morpholino (CD47M). After 48 hours, cells were administered doxorubicin as indicated.
Figure 2B:
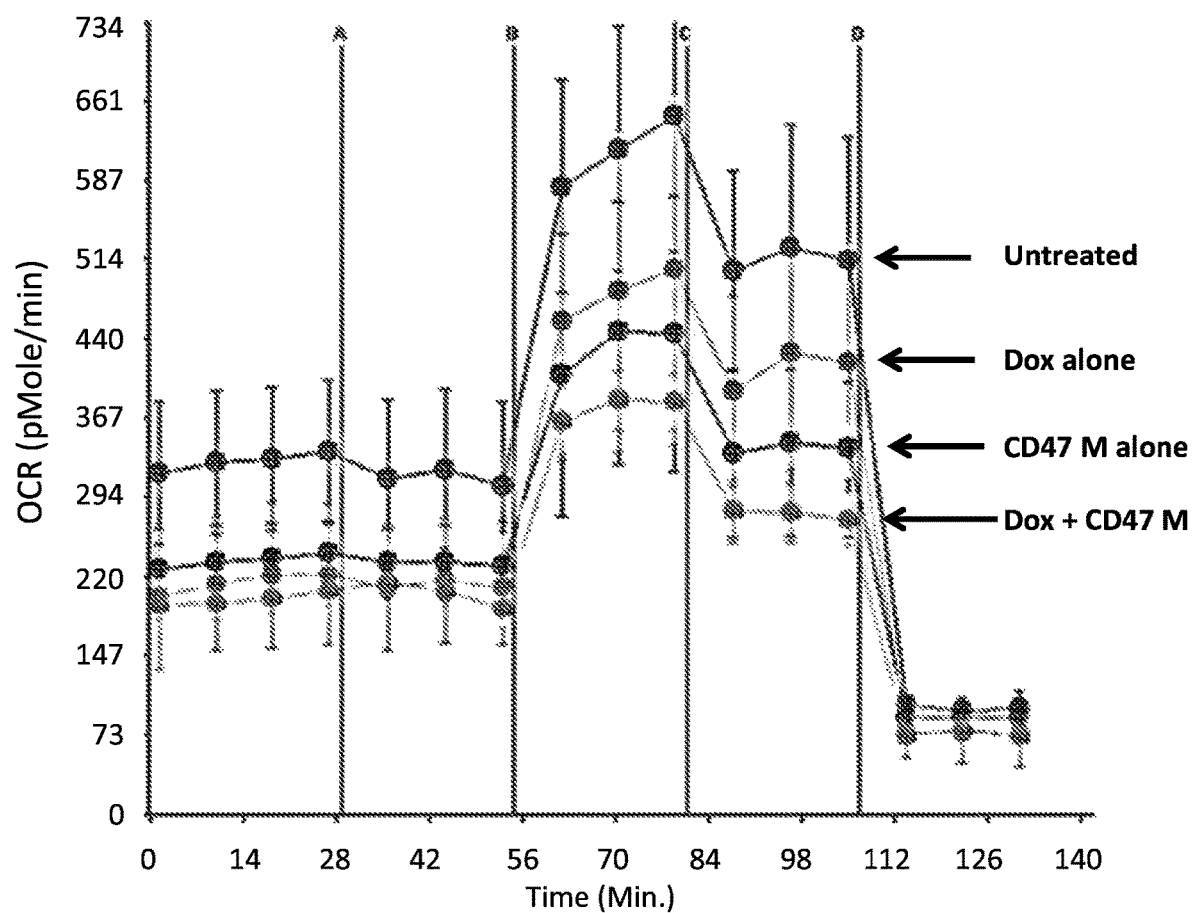
FIG. 2B is a graph showing OCR in B16 mouse melanoma cells untreated or treated with 10 µM CD47 morpholino (CD47M). After 48 hours, cells were administered doxorubicin as indicated.

To start elucidating the molecular mechanism of breast cancer sensitization to anthracycline therapy with CD47 blockade oxygen consumption rate (OCR) was tested. OCR is a measurement of mitochondrial respiration and is extremely sensitive to changes in metabolic demand (Tao et al., *Anal. Biochem.* 381:43-52, 2008). Increased OCR is an indicator of mitochondrial dysfunction in transformed cells associated with tumor aggressiveness and resistance to therapy (Vaupel and Mayer, *Int. J. Biochem. Cell Biol.* 44:1477-1481, 2012). To measure OCR, 4T1 breast cancer cells or B16 melanoma cells were plated in 24-well plates using the XF24 flux analyzer (Seahorse Bioscience). Cells were exposed to known mitochondrial poisons (oligomicin, carbonilcyanide p-triflouromethoxy-phenylhydrazone FCCP, or actinomycin A) to determine basal and maximal OCR. Untreated 4T1 cells showed an increased oxygen consumption rate, which is associated with mitochondrial dysfunction and cancer resistance. Treatment with doxorubicin also showed the same pattern in both 4T1 breast cancer cells and B16 melanoma cells (FIGS. 2A and B). On the other hand, blockade with CD47 alone caused a reduction in OCR, but blockade with CD47 and doxorubicin significantly reduced the oxygen consumption rate (FIGS. 2A and B). This shows that blockade of CD47 alone and in conjunction with anthracycline treatment decreases OCR in cancer cells.

Figure 2C:
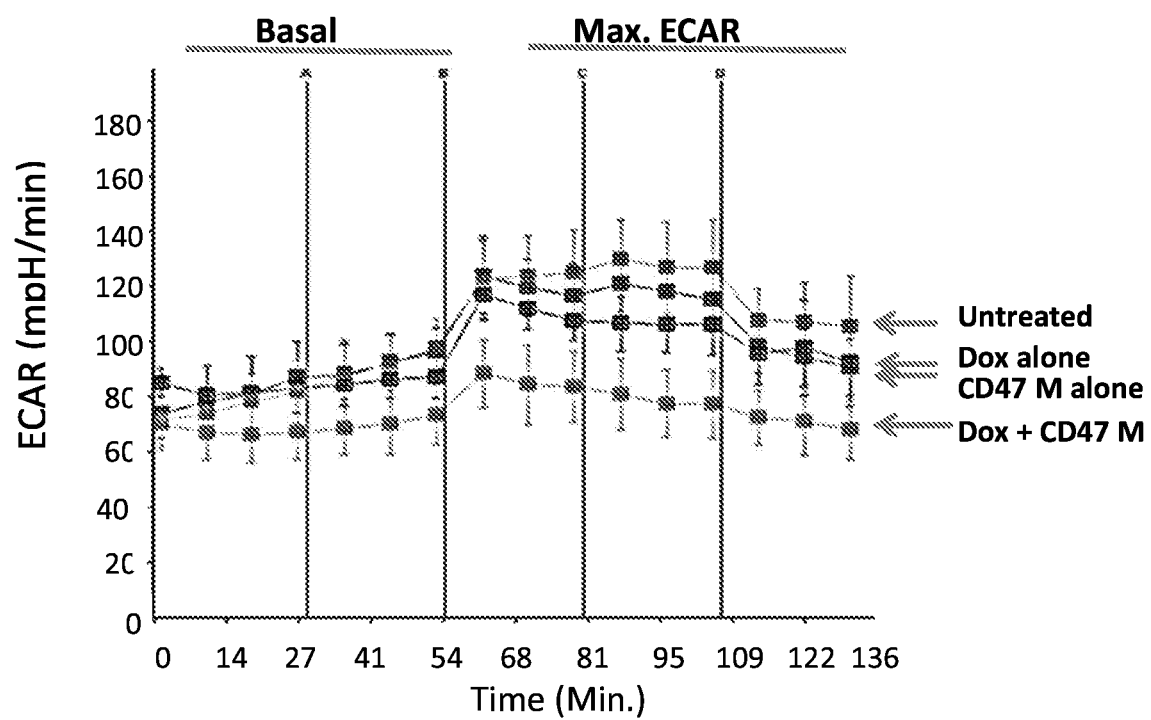
FIG. 2C is a graph showing extracellular acidification rate (ECAR) in 4T1 breast cancer cells untreated or treated with 10 µM CD47 morpholino (CD47M). After 48 hours, cells were administered doxorubicin as indicated.

It is well known that cancer cells show increased glycolytic flux. Cells with elevated glycolysis exhibit increased lactic acid production and therefore an increased extracellular acidification rate. Increased glycolysis is a hallmark of tumor aggressiveness, and targeting tumor acidity is demonstrated to reduce tumor burden. The extracellular acidification rate (ECAR) was measured in 4T1B cells using the XF24 flux analyzer following the same treatments stated above. As shown in FIG. 2C, control 4T1B cells showed high acidification in the media, as did the groups of cells treated with doxorubicin alone. Blockade with CD47 caused a slight decrease in the ECAR (FIG. 2C). However, combination with doxorubicin significantly reduced the acidification rate (FIG. 2C), indicating that blockade of CD47 reduces the glycolytic flux as measured by reduction in ECAR to sensitize breast cancer cells to death by chemotherapy treatment.

Figure 10:
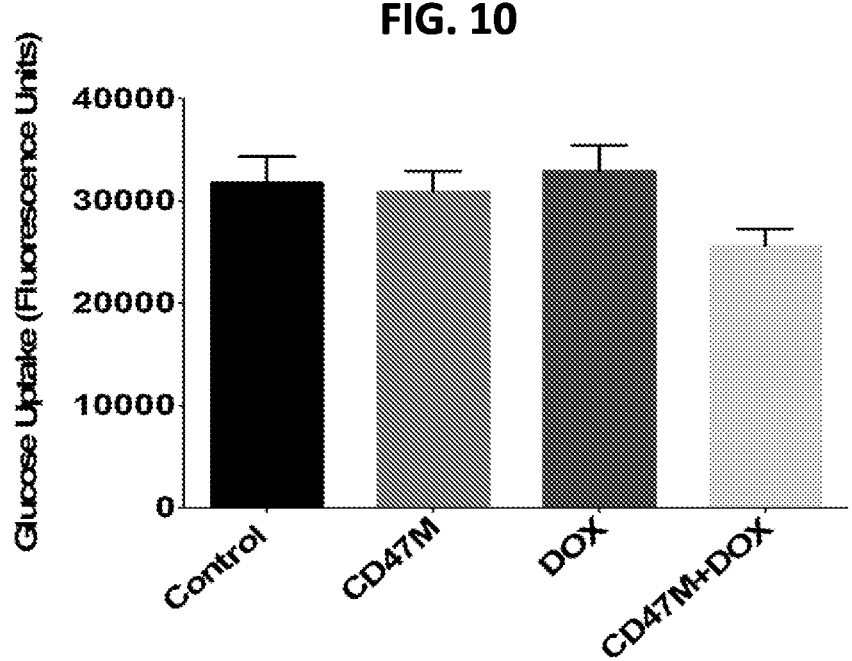
FIG. 10 is a graph showing glucose uptake in 4T1B cells treated with saline, doxorubicin (DOX), CD47 morpholino (CD47M), or combination CD47 morpholino and doxorubicin treatment. Glucose uptake was measured 24 hours after treatment.
Figure 11:
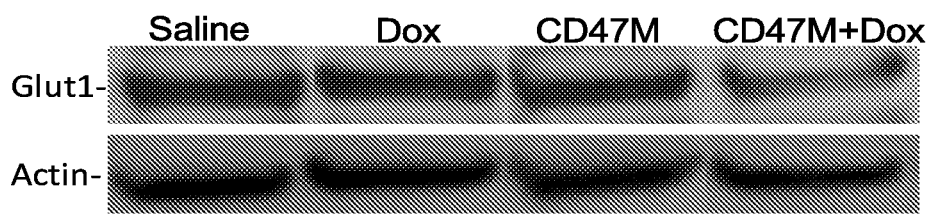
FIG. 11 is a digital image of a Western blot of GLUT-1 (top panel) and actin (bottom panel) in tumors from mice treated with saline, doxorubicin (DOX), CD47 morpholino (CD47M), or combination doxorubicin and CD47 morpholino treatment.

In addition, combination treatment with CD47 M and dox reduced glucose uptake in vitro. 4T1B cells were plated and treated and a group was treated with CD47 M. After 48 hours, one group of untreated cells and one of the CD47 M treated cells were treated with Dox. Glucose uptake was measured 24 hours after treatment by adding 2-NBDG, which is a fluorescently labeled deoxyglucose analog that is used primarily to directly monitor glucose uptake by living cells. This confirmed that the combination treatment modified glucose metabolism to sensitize cells to Dox treatment (FIG. 10). Furthermore, blockade of CD47 in combination with dox decreased expression of the Glut-1 glucose transporter in vivo (FIG. 11). Tumors of mice were exised and protein expression was determined by western blot hybridization. Expression of Glut-1 was not affected by treatment with saline, doxorubicin or CD47 morpholino (CD47M) alone. However the combination of Dox and CD47 M reduced Glut-1 transporter expression in vivo. Glut-1 facilitates the transport of glucose in cells and is a poor prognostic factor in breast cancer and other cancer types. This indicates that reduction of Glut-1 could mediate in part the effects on bioenergetics observed previously and the reduction of tumor growth observed in the in vivo studies above.

Figure 3A:
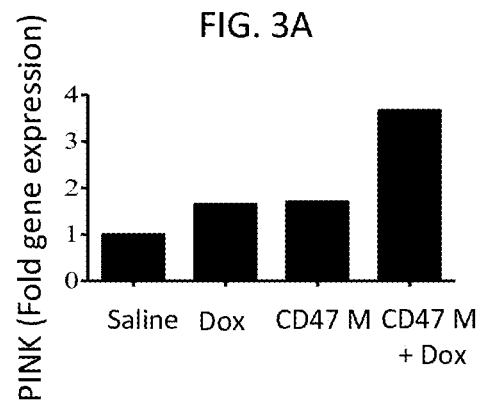
FIGS. 3A and 3B are a pair of graphs showing RT-PCR quantification of PTEN-Induced Putative Kinase (PINK) (A) and PARKIN (B) gene expression in 4T1 breast cancer cells treated as shown.
Figure 3B:
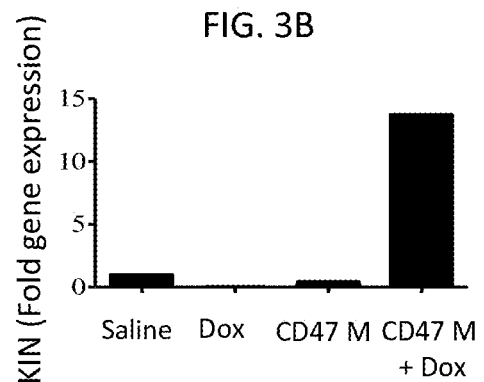
Figure 3C:
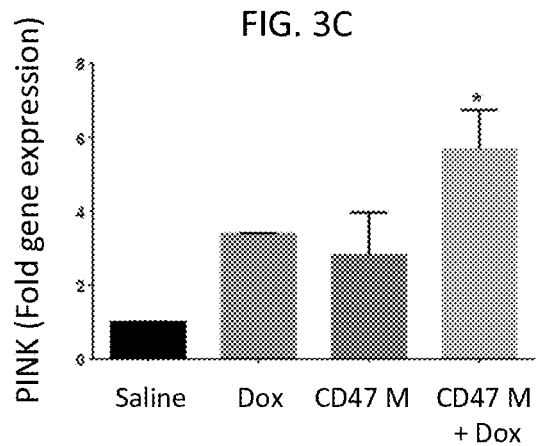
FIGS. 3C and 3D are a pair of graphs showing RT-PCR quantification of PINK (C) and PARKIN (D) gene expression in 4T1 breast tumors at time of collection from mice treated as shown.
Figure 3D:
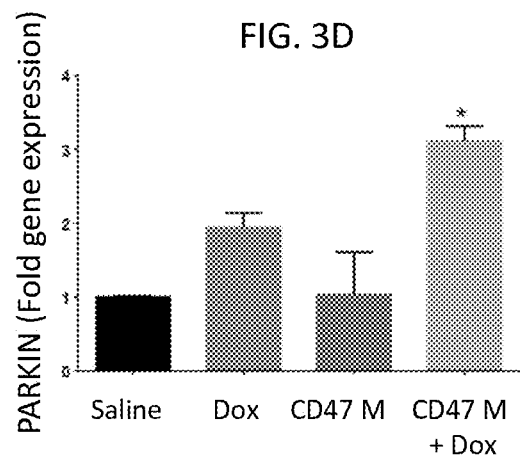

Blockade of CD47 Increases Mitophagy Gene Expression In Vitro and In Vivo:

As shown in FIGS. 1A and B a profound sensitization of breast tumor to anthracycline chemotherapy resulted from CD47 blockade. Autophagy can promote either survival or death of tissue. Selective mitochondrial turnover by mitophagy in tumor tissue can shift this pathway to a pro-death response (Gargini et al., *Autophagy* 7:466-476, 2011). To further understand the mechanism of mitophagy in breast cancer cells, 4T1 breast cancer cells were plated and treated with CD47 morpholino for 48 hours. After incubation, cells were treated with 10 µg/ml of doxorubicin. After 24 hours incubation, cells were harvested and RNA was isolated. Gene expression was determined by qRT-PCR. While control, doxorubicin treatment, and CD47 blockade alone showed minimal effects, combination treatment with doxorubicin and CD47 morpholino increased PINK and PARKIN 3- to 10-fold respectively (FIGS. 3A and B). Moreover, increases in both PINK and PARKIN occurred in vivo in RNA isolated from 4T1 breast cancer tumors grown in mice receiving the combination treatment (FIGS. 3C and D). This suggests that blockade of CD47 in combination with doxorubicin treatment increases both PINK and PARKIN to increase mitochondrial turnover and that the tumor sensitization observed in this animal model was associated with an increase in mitophagy.

Blockade of CD47 Protects Cardiac Tissue from Death Associated with Anthracycline Treatment.

Figure 13:
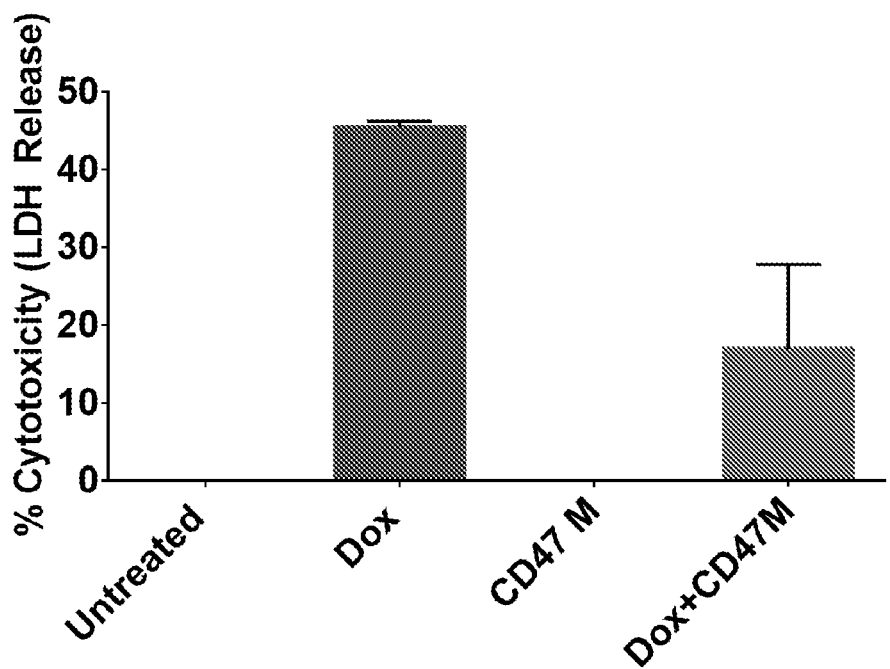
FIG. 13 is a graph showing cytotoxicity (lactate dehydrogenase release in H9c2 cardiac myoblast cells treated with doxorubicin (Dox), CD47 morpholino (CD47M), or a combination of doxorubicin and CD47 morpholino.

One of the most prevalent side effects of anthracycline therapy is cardiac toxicity. H9c2 cardiac myoblast cells were plated and one group was treated with CD47 Morpholino. After 48 hours incubation one group of untreated cells and one of the CD47 M treated cells were administered Dox (10 mg/ml). Lactate dehydrogenase (LDH) release was determined 24 hours after treatment as a measure of cell cytotoxicity. Treatment with Dox alone increased LDH release when compared to untreated cells; however, treatment with CD47M reduced the Dox-induced cardiac cell cytotoxicity (FIG. 13). This indicates that blockade of CD47 reduces Dox mediated cardiac cell death.

Figure 4:
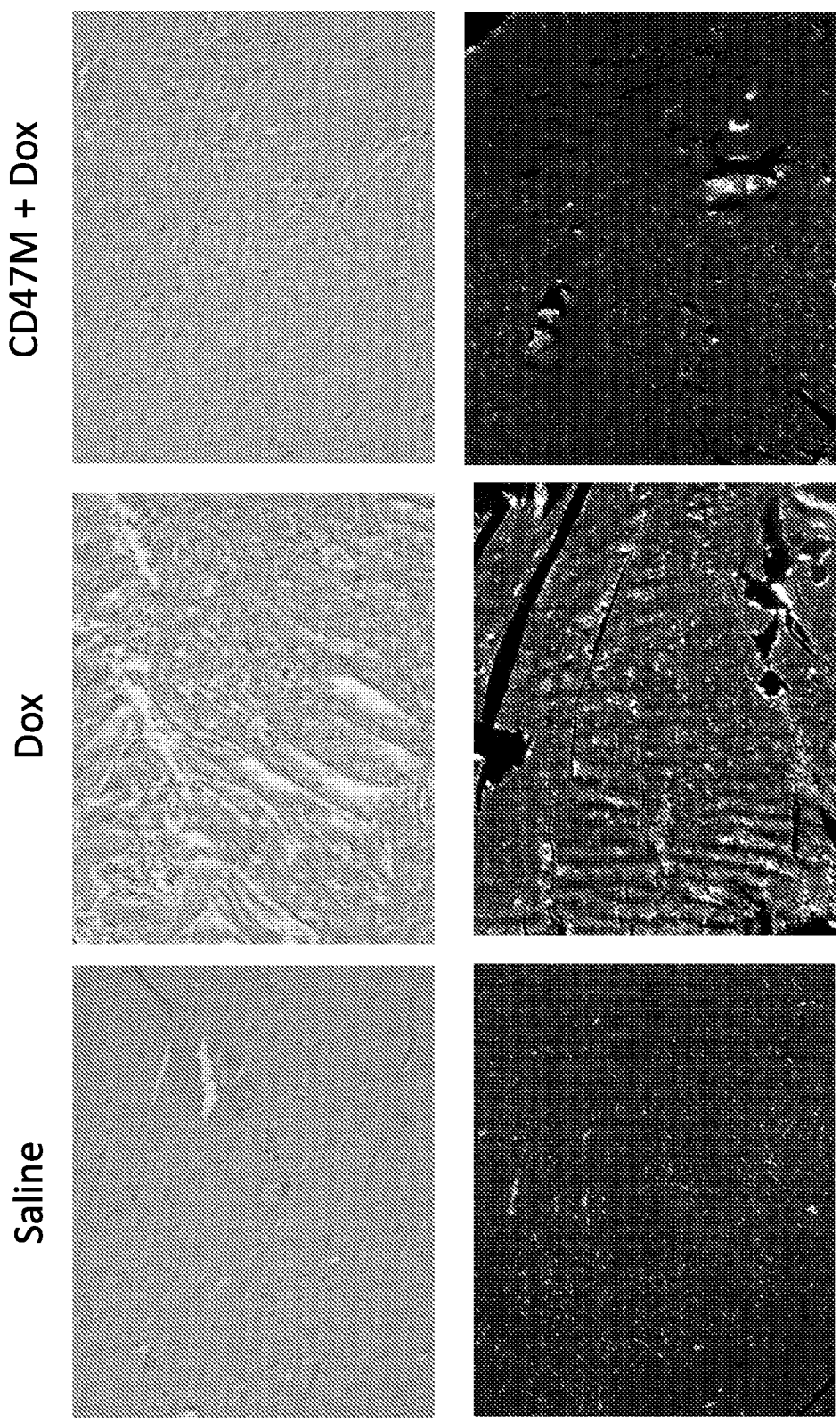
FIG. 4 is a series of digital images of hematoxylin & eosin (H&E) stained (top panels) or TUNEL stained (bottom panels) cardiac tissue from mice after four rounds of saline, doxorubicin treatment, or doxorubicin treatment in combination with CD47 morpholino.

Hearts were collected from mice at the end of the tumor studies after four rounds of weekly doxorubicin treatment in the presence or absence of CD47 blockade. Sections were paraffin embedded and stained with H&E to determine tissue histology. Hearts of saline treated animals show no evidence of toxicity (FIG. 4, top panel, left). Hearts of mice treated with doxorubicin showed the characteristic degeneration of cardiac muscle caused by doxorubicin treatment (Li et al., *Circulation* 113:535-543, 2006) (FIG. 4A, top panel, middle). Blockade of CD47 using the antisense morpholino prevented this cardiac damage (FIG. 4, top panel, right).

Figure 16B:
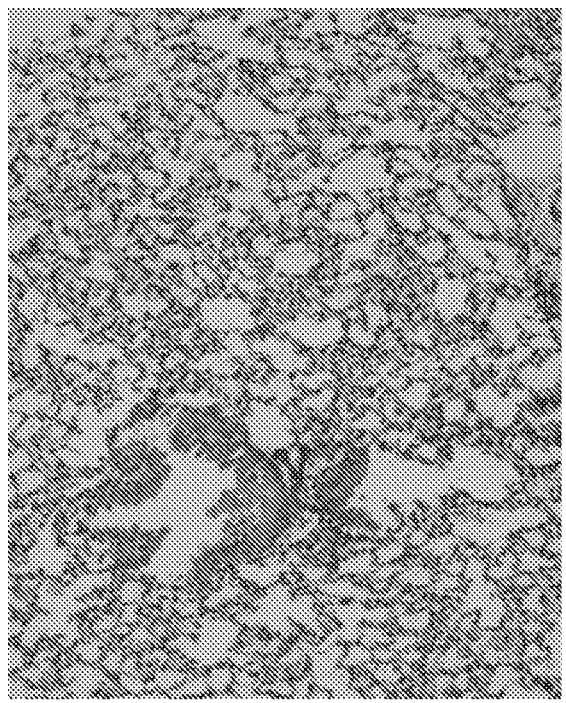
FIGS. 16A and B are digital images of lung sections from mice treated with Dox (FIG. 16A) or Dox plus CD47 morpholino (FIG. 16B).
Figure 16A:
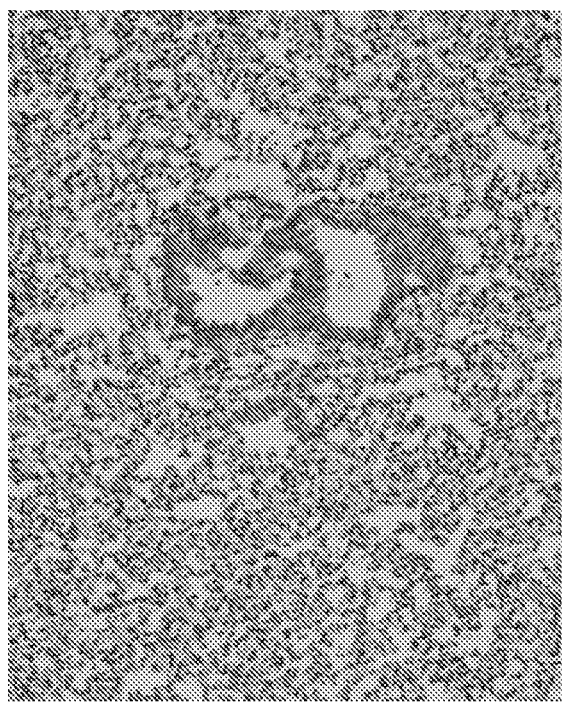

Tissue sections were subjected to TUNEL staining to detect cell death. Hearts of mice treated with saline showed basal cell death and those of mice treated with doxorubicin showed high TUNEL positive staining, indicating cell death in cardiac tissue (FIG. 4, bottom panel, left and middle). However, blockade of CD47 caused a remarkable protection from death associated with doxorubicin treatment (FIG. 4, bottom panel, right). This indicates that blockade of CD47 selectively protects cardiac tissue in a syngeneic model of breast cancer and prevents anthracycline induced cardiac toxicity. In addition, lung tissue in the mice treated with CD47 blockade in combination with doxorubicin appeared to be in better condition than lung tissue in the mice treated with doxorubicin alone by visual observation. There was less fibrosis in lung tissue from mice treated with Dox alone as compared to mice treated with CD47 morpholino in combination with Dox (FIGS. 16A and B). This suggests that the protective effect of CD47 blockade from anthracycline cytotoxicity is not limited solely to heart tissue.

Blockade of CD47 Induces Protective Autophagy in Heart Tissue:

WT and CD47 null mice were treated with doxorubicin to determine effects on autophagy gene expression. Atg5 and Atg7 mRNA levels were markedly increased in hearts of CD47 null mice treated with doxorubicin (FIGS. 5A and B). On the other hand a slight reduction of Atg5 (FIG. 5A) was observed in hearts of WT mice treated with doxorubicin only, and minor effects on autophagy with the rest of the treatment groups. This indicates that the cardioprotection observed with CD47 treatment is associated with an increase in autophagy gene expression.

Human CD47-Deficient T Cells are Resistant to Anthracycline Associated Cell Cytotoxicity:

In order to determine if the protection from doxorubicin associated cell death is cell autonomous, WT and CD47 deficient Jurkat T cells were treated with increasing concentration of doxorubicin. WT T-cells showed decreased viability with doxorubicin treatment while CD47 deficient cells showed a dose-dependent protection from doxorubicin-associated cytotoxicity (FIG. 6). This indicates that the protection observed with CD47 blockade also extends to T-cells, which could indicate that it could protect normal tissue from death associated to doxorubicin treatment. This also demonstrates that loss of CD47 in human cells is cytoprotective against doxorubicin treatment.

Figure 7C:
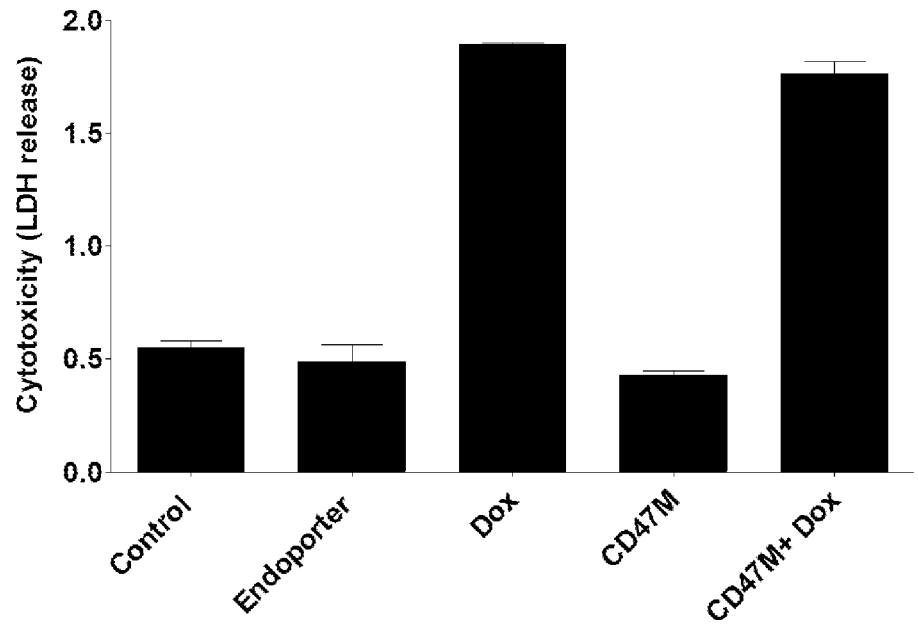
Figure 7D:
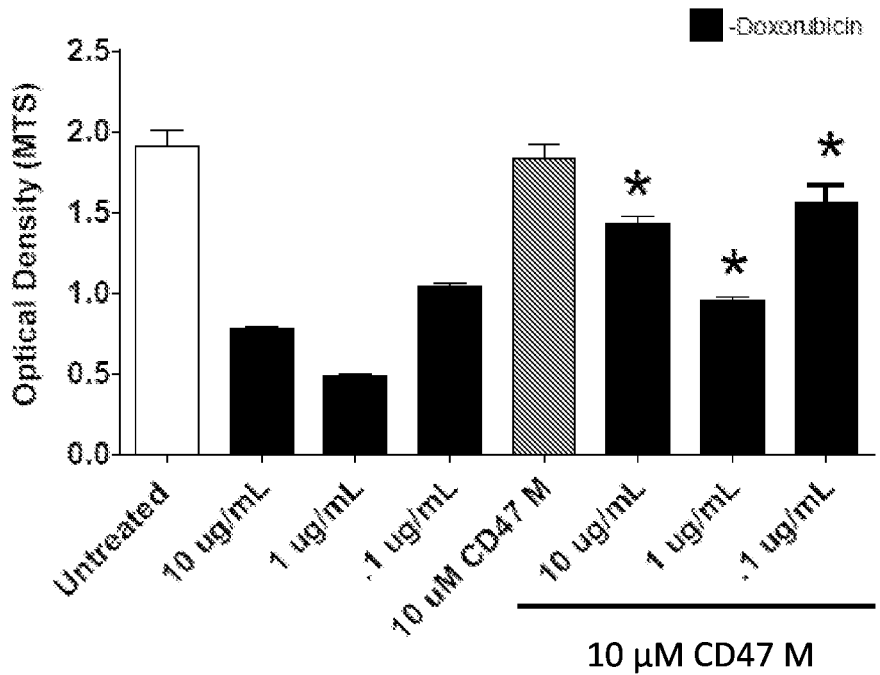

Blockade of CD47 does not Protect Breast Cancer Cells from Cytotoxicity Associated with Anthracycline Treatment:

4T1 breast cancer cells were treated with CD47 morpholino and treated with increasing concentrations of doxorubicin. Treatment with doxorubicin caused a reduction in cell viability (FIG. 7A). Moreover, blockade of CD47 had no effect in the decrease in viability observed with doxorubicin treatment (FIG. 7A). Blockade of CD47 also reduced viability of B16 mouse melanoma cells and CT26 mouse colon carcinoma cells treated with doxorubicin (FIGS. 7B and C). However, blockade of CD47 protected human umbilical vein endothelial cells from doxorubicin toxicity (FIG. 7D). This indicates that blockade of CD47 selectively protects normal but not cancer cells.

Figure 8:
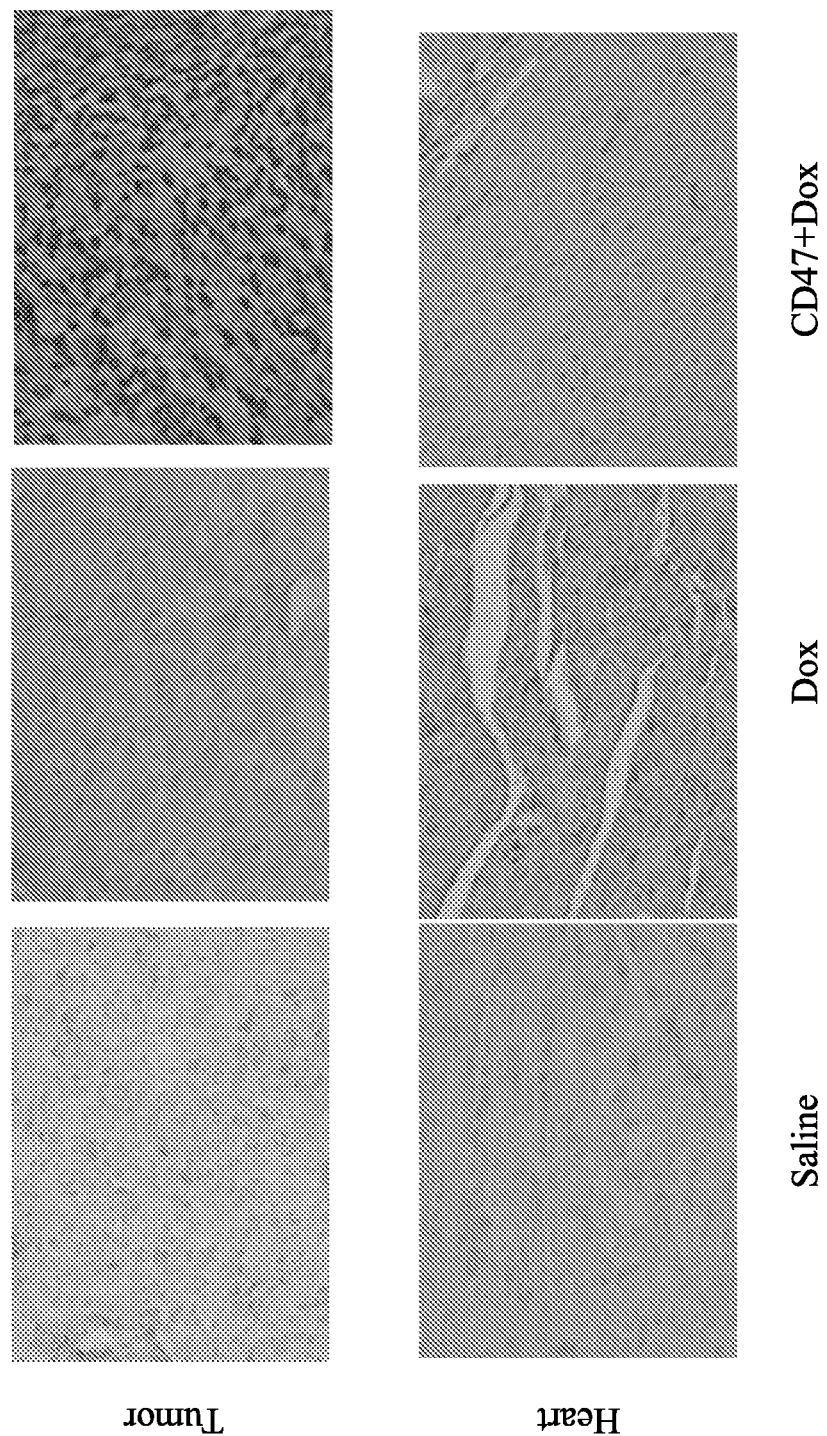
FIG. 8 is a series of digital images showing PINK protein expression (visualized as brown staining) in sections of tumor (top panel) or heart (bottom panel) from tumor bearing mice, treated as indicated.

Blockade with CD47 Causes Differential Expression of PINK in Tumor and Heart Tissue:

Tissue sections from the initial tumor model were immune-stained for PINK. A marked increase in PINK expression in tumor sections was observed in mice treated with CD47 morpholino in combination with anthracycline when compared to those of saline or doxorubicin alone (FIG. 8, top panel, right). This suggests that mitophagy is upregulated in tumor tissue sensitized to doxorubicin chemotherapy by CD47 blockade. No change in PINK expression was observed in hearts from the three treatment groups, (FIG. 8, bottom panel) suggesting a tissue specific regulation of PINK, and therefore mitophagy, in tumor versus normal heart tissue.

Example 2

Blockade of CD47 Decreases Antimetabolite and Topoisomerase Inhibitor Cytotoxicity to Non-Tumor Cells Wild type or CD47 null Jurkat cells were plated at a density of $7 \times 10^3$/well in 96 well plates. Cells were treated with 10 μg/ml 5-FU or 50 mg/ml camptothecin. Cell viability was measured 72 hours after treatment by MTS reduction.

Figure 9:
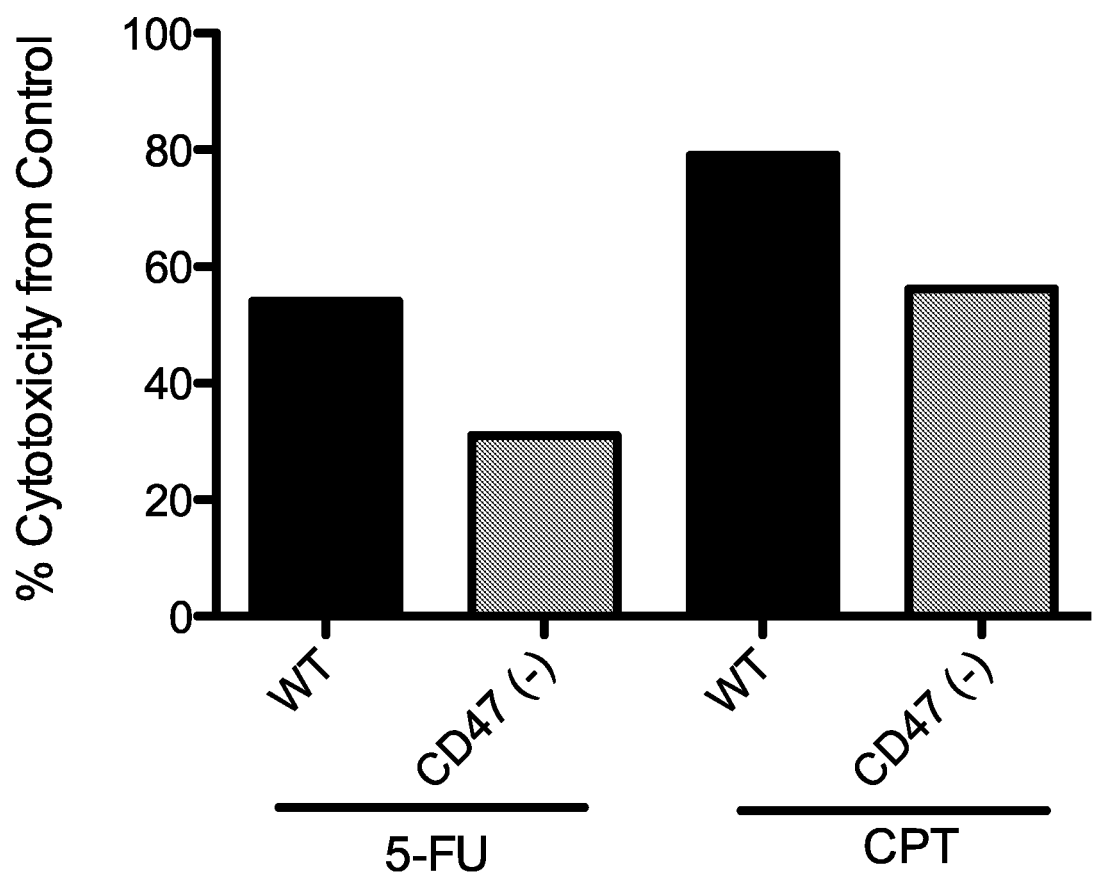
FIG. 9 is a graph showing cell viability (expressed as percent increase in cytotoxicity relative to untreated control cells) in WT or CD47 null (CD47-) Jurkat cells cultured in the presence of 5-fluorouracil (5-FU) or camptothecin (CPT).

Treatment with 5-FU caused 59% cytotoxicity to wild type Jurkat cells, but only 31% cytotoxicity to CD47 deficient Jurkat cells (FIG. 9). Moreover, treatment with camptothecin caused 79% cytotoxicity to wild type Jurkat cells and 56% in CD47 deficient Jurkat cells. These data demonstrate that inhibition of CD47 signaling decreases the cytotoxicity of these chemotherapy agents in non-tumor cells.

Example 3

Blockade of CD47 Decreases Cytotoxicity of Chemotherapeutic Compounds to Non-Tumor Cells This example demonstrates that blockade of CD47 decreases cytotoxicity of a broad spectrum of chemotherapeutic compounds in non-tumor cells.

A panel of 1913 approved and experimental chemotherapeutic agents were screened for inhibition of viability of non-tumor cells. Wild-type or CD47 deficient Jurkats cells were plated in sterile, tissue culture-treated 1536-well white solid-bottom plates. A total of 500 cells per well were seeded using a Multidrop Reagent dispenser with a small pin cassette. Compounds were dispensed at concentrations ranging from $10^{-9}$ to $10^{-4}$ M, and the plates were covered with stainless steel Kalypsys microplate lids and placed into an incubator at 37° C., with 5% $CO_2$ and 95% relative humidity. The plates were incubated for 48 hours, and then 3 μL CellTiter-Glo® assay reagent (Promega, Madison, Wis.) was added. Relative luminescence units (RLU) were quantified using a ViewLux™ imager (PerkinElmer, Waltham, Mass.) to determine viability of cells.

Table 1 shows compounds that exhibited decreased maximal inhibition of cell survival at 48 hours in CD47 null Jurkat cells compared to WT Jurkat cells. Table 2 shows compounds that exhibited decreased potency for inhibiting cell viability (AC50 values) in CD47 null Jurkat cells compared to WT Jurkat cells. Of the 1913 compounds tested, 411 were active, but showed no significant differences in AC50 values between WT and CD47 null Jurkat cells.

TABLE 1

Compounds with decreased maximal inhibition of cell survival in CD47 deficient (CD47 KO) Jurkat T cells

| Name | Maximal Response CD47 KO (RLU) | Maximal Response WT (RLU) | Δ Maximal Response CD47KO-WT | z-score Δ Maximal Response CD47KO-WT |
|---|---|---|---|---|
| Silybin | 40.999 | 13.77 | 27.229 | 1.369495095 |
| Zosuquidar trihydrochloride | 39.638 | 17.315 | 22.323 | 1.070129203 |
| Valspodar | 83.876 | 56.155 | 27.721 | 1.399517113 |
| DCC-2036 | 41.19 | 3.812 | 37.378 | 1.988790741 |
| Cladribine | 59.738 | 21.67 | 38.068 | 2.030894791 |
| Daidzin | 144.949 | 115.579 | 29.37 | 1.500139688 |
| JK 184 | 39.212 | 13.602 | 25.61 | 1.27070313 |
| Rolofylline | 84.234 | 61.315 | 22.919 | 1.106497338 |
| Dobutamine hydrochloride | 40.55 | 8.698 | 31.852 | 1.651592225 |
| Isoprenaline hydrochloride | 53.781 | 7.997 | 45.784 | 2.501727898 |
| Eprosartan mesylate | 90.261 | 63.38 | 26.881 | 1.348260009 |
| EBPC | 122.465 | 100.134 | 22.331 | 1.070617366 |
| Triciribine | 120.768 | 92.368 | 28.4 | 1.440949938 |
| MK-2206 | 30.241 | 1.791 | 28.45 | 1.444000956 |
| AZD-5363 | 25.014 | 1.231 | 23.783 | 1.15921893 |
| Akt-l-1 | 72.553 | 10.094 | 62.459 | 3.519242422 |
| Triciribine phosphate | 80.607 | 52.513 | 28.094 | 1.422277707 |
| GDC-0068 | 31.005 | 2.029 | 28.976 | 1.476097666 |
| Masoprocol | 31.706 | 3.946 | 27.76 | 1.401896907 |
| Licofelone | 32.374 | 9.166 | 23.208 | 1.124132222 |
| MK-886 | 40.805 | 13.757 | 27.048 | 1.35845041 |
| VE-821 | 64.063 | 17.653 | 46.41 | 2.539926644 |
| SNS-314 | 60.794 | 31.863 | 28.931 | 1.47335175 |
| AMG-900 | 52.081 | 26.057 | 26.024 | 1.29596556 |
| JNJ-7706621 | 44.022 | 4.83 | 39.192 | 2.099481677 |
| Alisertib | 53.002 | 28.645 | 24.357 | 1.194244617 |
| AT-9283 | 24.648 | 2.937 | 21.711 | 1.032784742 |
| TAK-901 | 33.892 | 4.465 | 29.427 | 1.503617849 |
| PF-03814735 | 25.285 | 2.512 | 22.773 | 1.097588365 |
| MK-5108 | 85 | 50.854 | 34.146 | 1.791572934 |
| ABT-737 | 29.852 | 1.054 | 28.798 | 1.465236042 |
| TW-37 | 34.779 | 13.439 | 21.34 | 1.010146188 |
| I-BET762 | 41.586 | 9.858 | 31.728 | 1.6440257 |
| Aloxistatin | 132.797 | 104.466 | 28.331 | 1.436739533 |
| Emricasan | 69.759 | 26.974 | 42.785 | 2.318727835 |
| PAC-1 | 41.834 | 10.752 | 31.082 | 1.604606547 |
| AC-265347 | 108.022 | 76.539 | 31.483 | 1.629075712 |
| SB262470 NPS-2143 | 97.874 | 19.594 | 78.28 | 4.484645557 |
| AG-041R | 52.368 | 9.739 | 42.629 | 2.309208658 |
| PHA-767491A | 50.652 | 3.817 | 46.835 | 2.565860298 |
| Flavopiridol??? | 37.554 | 2.486 | 35.068 | 1.847833707 |
| AT-7519 | 27.655 | 1.678 | 25.977 | 1.293097603 |
| PHA-793887 | 33.85 | 1.453 | 32.397 | 1.684848322 |
| RGB-286147 | 39.37 | 1.775 | 37.595 | 2.00203216 |
| BS-194 | 43.598 | 1.928 | 41.67 | 2.250690132 |
| R-547 | 36.61 | 3.1 | 33.51 | 1.752763984 |
| Dinaciclib | 47.924 | 3.92 | 44.004 | 2.393111655 |
| Milciclib | 34.643 | 3.772 | 30.871 | 1.591731251 |
| SNS-032 | 34.22 | 0.946 | 33.274 | 1.738363179 |
| PTC-124 | 109.291 | 77.858 | 31.433 | 1.626024694 |
| Lumacaftor | 34.976 | 4.41 | 30.566 | 1.57312004 |
| AZD-7762 | 39.585 | 9.778 | 29.807 | 1.526805586 |
| AM-630 | 36.125 | 12.87 | 23.255 | 1.127000179 |
| Tolcapone | 72.927 | 36.753 | 36.174 | 1.915322226 |
| KI-20227 | 42.569 | 12.143 | 30.426 | 1.56457719 |
| CAA0225 | 41.833 | 13.449 | 28.384 | 1.439973612 |
| Methyltestosterone | 45.934 | 19.391 | 26.543 | 1.327635127 |
| Exemestane | 77.388 | 48.822 | 28.566 | 1.451079318 |
| Baicalein | 91.667 | 63.506 | 28.161 | 1.426366072 |
| Methyldopa | 66.092 | 2.736 | 63.356 | 3.573977686 |
| Methotrexate | 54.169 | 9.002 | 45.167 | 2.464078335 |
| Vidofludimus | 64.725 | 19.287 | 45.438 | 2.480614853 |
| NSC-48006 | 46.143 | 20.924 | 25.219 | 1.246844169 |
| Gimeracil | 106.453 | 83.034 | 23.419 | 1.137007519 |
| Fenoldopam | 93.129 | 61.271 | 31.858 | 1.651958347 |
| AG-1024 | 55.705 | 21.585 | 34.12 | 1.789986404 |
| Sapitinib | 42.354 | 14.043 | 28.311 | 1.435519126 |
| Mubritinib | 45.69 | 17.243 | 28.447 | 1.443817895 |
| Estriol | 120.332 | 72.648 | 47.684 | 2.617666584 |

TABLE 1-continued

Compounds with decreased maximal inhibition of cell survival in CD47 deficient (CD47 KO) Jurkat T cells

| Name | Maximal Response CD47 KO (RLU) | Maximal Response WT (RLU) | Δ Maximal Response CD47KO-WT | z-score Δ Maximal Response CD47KO-WT |
|---|---|---|---|---|
| YK-4-279 | 38.318 | 14.615 | 23.703 | 1.154337301 |
| Cerulenin | 39.947 | 10.602 | 29.345 | 1.498614179 |
| SG-00529 | 39.325 | 14.623 | 24.702 | 1.215296642 |
| Orantinib | 36.73 | 6.657 | 30.073 | 1.543037002 |
| Tivozanib | 30.389 | 8.955 | 21.434 | 1.015882102 |
| Vargatef | 50.125 | 12.253 | 37.872 | 2.0189348 |
| Lenvatinib | 51.428 | 5.012 | 46.416 | 2.540292766 |
| Motesanib | 68.692 | 21.286 | 47.406 | 2.600702924 |
| JNJ-38158471 | 64.339 | 28.354 | 35.985 | 1.903789378 |
| HMSL10084 | 24.556 | 2.486 | 22.07 | 1.054691051 |
| Osthol | 60.073 | 35.688 | 24.385 | 1.195953188 |
| Dihydromyricetin | 36.707 | 15.036 | 21.671 | 1.030343927 |
| Spermidine | 82.208 | 20.847 | 61.361 | 3.452242065 |
| TWS-119 | 41.471 | 15.256 | 26.215 | 1.307620449 |
| Ezatiostat | 113.889 | 68.407 | 45.482 | 2.483299749 |
| ICI-D7288 | 27.963 | 5.518 | 22.445 | 1.077573687 |
| SB-408124 | 50.614 | 23.067 | 27.547 | 1.38889957 |
| PCI-34051 | 74.801 | 33.723 | 41.078 | 2.214566078 |
| 2-Methoxyestradiol | 45.435 | 21.899 | 23.536 | 1.144146901 |
| IOX2 | 113.814 | 89.375 | 24.439 | 1.199248287 |
| Atorvastatin calcium | 57.007 | 34.989 | 22.018 | 1.051517992 |
| Mizolastine | 89.324 | 60.168 | 29.156 | 1.487081331 |
| Ac-SAH-p53-8 | 37.723 | 11.534 | 26.189 | 1.306033919 |
| Fluvoxamine maleate | 34.845 | 0.209 | 34.636 | 1.821472911 |
| Rizatriptan benzoate | 83.76 | 62.211 | 21.549 | 1.022899443 |
| Amoxapine | 60.648 | 28.037 | 32.611 | 1.697906679 |
| Ziprasidone hydrochloride | 42.21 | 17.586 | 24.624 | 1.210537054 |
| Picropodophyllin | 37.377 | 12.497 | 24.88 | 1.226158266 |
| BMS-754807 | 82.867 | 47.422 | 35.445 | 1.870838383 |
| BMS-345541 | 23.272 | 1.923 | 21.349 | 1.010695371 |
| PS-1145 | 97.256 | 67.733 | 29.523 | 1.509475804 |
| PF-184 | 51.177 | 15.645 | 35.532 | 1.876147154 |
| Mycophenolic acid | 58.678 | 19.34 | 39.338 | 2.108390649 |
| Ribavirin | 113.259 | 82.278 | 30.981 | 1.59844349 |
| Mycophenolate mofetil | 71.329 | 19.156 | 52.173 | 2.891586986 |
| NCGC00241410-01 | 41.906 | 11.766 | 30.14 | 1.547125367 |
| Merck 5 | 71.573 | 49.62 | 21.953 | 1.047551669 |
| Tyrphostin B42 | 67.867 | 35.116 | 32.751 | 1.70644953 |
| NCGC00183808-01 | 74.518 | 35.566 | 38.952 | 2.08483679 |
| NCGC00241036-01 | 73.954 | 46.14 | 27.814 | 1.405192006 |
| Sophocarpine | 83.612 | 40.909 | 42.703 | 2.313724165 |
| Flupirtine maleate | 69.164 | 44.09 | 25.074 | 1.237996216 |
| Monastrol | 69.287 | 32.433 | 36.854 | 1.956816072 |
| S-Trityl-L-cysteine | 80.305 | 33.811 | 46.494 | 2.545052354 |
| SU-6656 | 72.735 | 39.636 | 33.099 | 1.727684615 |
| Phenelzine | 51.795 | 13.556 | 38.239 | 2.041329272 |
| Hydroxychloroquine sulfate | 112.507 | 88.656 | 23.851 | 1.163368315 |
| PD-184352 | 42.673 | 14.102 | 28.571 | 1.45138442 |
| XMD8-92 | 39.731 | 15.283 | 24.448 | 1.19979747 |
| HMSL10058 | 49.422 | 14.124 | 35.298 | 1.86186839 |
| HLI-373989 | 27.558 | 1.53 | 26.028 | 1.296209641 |
| Nutlin-3 | 49.966 | 7.821 | 42.145 | 2.279674803 |
| EMD-1214063 | 39.443 | 4.948 | 34.495 | 1.81286904 |
| AMG-1 | 40.721 | 12.765 | 27.956 | 1.413856898 |
| Tivantinib | 35.424 | 9.411 | 26.013 | 1.295294336 |
| NVP-BVU-972 | 80.831 | 49.524 | 31.307 | 1.618336128 |
| Doxycycline | 47.095 | 19.309 | 27.786 | 1.403483436 |
| PD-166793 | 46.846 | 10.39 | 36.456 | 1.932529968 |
| Eltrombopagolamine | 33.444 | 9.025 | 24.419 | 1.19802788 |
| Pravadoline | 110.289 | 83.446 | 26.843 | 1.345941236 |
| WYE-354 | 31.102 | 2.442 | 28.66 | 1.456815232 |
| Ridaforolimus | 33.391 | 8.791 | 24.6 | 1.209072565 |
| Carbidopa | 43.994 | 12.731 | 31.263 | 1.615651232 |
| Chlorambucil | 92.524 | 16.98 | 75.544 | 4.317693849 |
| Ganciclovir | 69.097 | 6.562 | 62.535 | 3.523879969 |
| Hydrochlorothiazide | 42.166 | 15.923 | 26.243 | 1.309329019 |
| Levodopa | 77.71 | 43.316 | 34.394 | 1.806705983 |
| Bufexamac | 80.782 | 34.171 | 46.611 | 2.552191737 |
| Methacycline hydrochloride | 46.269 | 18.154 | 28.115 | 1.423559135 |
| Amoxicillin sodium | 61.467 | 27.97 | 33.497 | 1.751970719 |
| Antimycin A | 46.04 | 24.41 | 21.63 | 1.027842092 |
| Fluocinolone acetonide | 57.23 | 25.744 | 31.486 | 1.629258773 |
| Triamcinolone acetonide | 99.996 | 71.308 | 28.688 | 1.458523802 |
| Emetine | 33.945 | 5.168 | 28.777 | 1.463954614 |
| Aspartame | 127.356 | 103.971 | 23.385 | 1.134932826 |
| Neohesperidin dihydrochalcone | 31.011 | 9.336 | 21.675 | 1.030588009 |
| Oxytetracycline | 71.104 | 40.887 | 30.217 | 1.551823934 |
| Chlormethine | 77.133 | 42.804 | 34.329 | 1.80273596 |
| Prostaglandin E2 | 68.744 | 41.698 | 27.046 | 1.358328369 |
| Cytarabine | 50.088 | 6.781 | 43.307 | 2.350580463 |
| Cyclosporine A | 34.992 | 13.202 | 21.79 | 1.03760535 |
| ThioTEPA | 81.874 | 23.813 | 58.061 | 3.250874873 |
| Terbinafine hydrochloride | 58.754 | 36.243 | 22.511 | 1.081601031 |
| Rabeprazole | 115.444 | 92.342 | 23.102 | 1.117664064 |
| 16,16-dimethyl PGE2 | 73.807 | 31.844 | 41.963 | 2.268569098 |
| Elactocin | 30.361 | 6.663 | 23.698 | 1.154032199 |
| Niguldipine | 133.155 | 102.048 | 31.107 | 1.606132056 |
| Mitomycin | 25.245 | 1.358 | 23.887 | 1.165565048 |
| Echinomycin | 55.044 | 8.075 | 46.969 | 2.574037026 |
| Malotilate | 81.666 | 32.716 | 48.95 | 2.694918362 |
| Adapalene | 48.053 | 20.674 | 27.379 | 1.378648149 |
| Argatroban | 92.128 | 64.584 | 27.544 | 1.388716509 |
| Oxaliplatin | 109.492 | 49.399 | 60.093 | 3.374868247 |
| Limonin | 137.297 | 106.306 | 30.991 | 1.599053694 |
| Valaciclovir | 73.063 | 45.639 | 27.424 | 1.381394065 |
| Prednisolone | 71.927 | 43.795 | 28.132 | 1.424596481 |
| Idoxuridine | 101.516 | 79.933 | 21.583 | 1.024974135 |
| Fludarabine phosphate | 46.884 | 12.348 | 34.536 | 1.815370875 |
| Minocycline | 52.108 | 7.169 | 44.939 | 2.450165693 |
| Estramustine | 135.618 | 105.466 | 30.152 | 1.547857611 |
| Ibandronate sodium hydrate | 127.096 | 103.48 | 23.616 | 1.14902853 |
| Carboplatin | 152.695 | 118.461 | 34.234 | 1.796942725 |
| Nateglinide | 111.519 | 76.528 | 34.991 | 1.843135139 |
| Danoprevir | 101.689 | 75.521 | 26.168 | 1.304752492 |
| Bleomycin sulfate | 76.042 | 18.436 | 57.606 | 3.223110609 |
| Elvitegravir | 44.755 | 12.72 | 32.035 | 1.662758951 |
| Asiatic acid | 87.171 | 61.399 | 25.772 | 1.280588429 |
| Baicalin | 78.198 | 52.935 | 25.263 | 1.249529065 |
| Puerarin | 110.056 | 12.378 | 97.678 | 5.668318525 |
| 10-Deacetylbaccatin | 76.768 | 39.362 | 37.406 | 1.990499311 |
| Entecavir | 63.062 | 7.89 | 55.172 | 3.074587049 |
| Cyclocytidine HCl | 59.998 | 9.572 | 50.426 | 2.784984415 |
| UK-383367 | 49.091 | 13.282 | 35.809 | 1.893049794 |
| Picoplatin | 53.529 | 11.955 | 41.574 | 2.244832177 |
| AGI-5198 | 45.976 | 24.153 | 21.823 | 1.039619022 |
| Bioymifi | 48.515 | 10.488 | 38.027 | 2.028392956 |
| NSC319726 | 47.192 | 9.878 | 37.314 | 1.984885438 |
| Moxonidine hydrochloride hydrate | 66.695 | 34.088 | 32.607 | 1.697662598 |
| Rilmenidine | 87.857 | 56.878 | 30.979 | 1.59832145 |
| SR9011 | 30.529 | 7.859 | 22.67 | 1.091303268 |
| Ro 51 | 35.756 | 4.309 | 31.447 | 1.626878979 |
| GW-791343 | 37.839 | 3.378 | 34.461 | 1.810794347 |
| AZ 11645373 | 35.262 | 3.025 | 32.237 | 1.675085064 |
| INO-1001 | 130.285 | 106.954 | 23.331 | 1.131637727 |
| Olaparib | 90.538 | 63.542 | 26.996 | 1.355277351 |
| Niraparib | 81.286 | 48.69 | 32.596 | 1.696991374 |
| Lirimilast | 87.201 | 61.864 | 25.337 | 1.254044571 |
| ASR-isobudimer-SO$_2$Ph-4-CH$_2$OC(O)NMe$_2$ | 50.082 | 27.802 | 22.28 | 1.067505327 |

TABLE 1-continued

Compounds with decreased maximal inhibition of cell survival in CD47 deficient (CD47 KO) Jurkat T cells

| Name | Maximal Response CD47 KO (RLU) | Maximal Response WT (RLU) | Δ Maximal Response CD47KO-WT | z-score Δ Maximal Response CD47KO-WT |
|---|---|---|---|---|
| BTM-2C-dimer ketone | 61.349 | 28.3 | 33.049 | 1.724633597 |
| Mifepristone | 38.548 | 7.203 | 31.345 | 1.620654902 |
| IC-87114 | 35.263 | 4.013 | 31.25 | 1.614857968 |
| GNE-493 | 47.021 | 18.068 | 28.953 | 1.474694198 |
| PIK-293 | 50.9 | 15.445 | 35.455 | 1.871448587 |
| CH-5132799 | 32.385 | 10.205 | 22.18 | 1.061403291 |
| GSK-2636771 | 51.53 | 26.827 | 24.703 | 1.215357662 |
| TGX-221 | 40.352 | 17.942 | 22.41 | 1.075437974 |
| CAL-101 | 32.28 | 9.332 | 22.948 | 1.108266928 |
| Oleanolic acid | 56.286 | 26.521 | 29.765 | 1.524242731 |
| IVX-214 | 32.053 | 8.077 | 23.976 | 1.17099586 |
| Triptolide | 65.405 | 5.613 | 59.792 | 3.356501118 |
| GW-7647 | 50.573 | 4.907 | 45.666 | 2.494527495 |
| Ciprofibrate | 94.451 | 12.532 | 81.919 | 4.706698652 |
| GW-6471 | 36.938 | 6.324 | 30.614 | 1.576049018 |
| GW-501516 | 97.955 | 75.948 | 22.007 | 1.050846769 |
| SR1664 | 67.276 | 25.029 | 42.247 | 2.28589888 |
| A-769662 | 125.676 | 69.086 | 56.59 | 3.161113922 |
| Enzastaurin | 40.303 | 13.534 | 26.769 | 1.341425729 |
| Actinomycin D | 42.128 | 2.014 | 40.114 | 2.15574245 |
| Rifapentine | 52.75 | 2.402 | 50.348 | 2.780224827 |
| AP-768 | 130.711 | 99.963 | 30.748 | 1.584225746 |
| Piroxicam | 106.754 | 80.791 | 25.963 | 1.292243318 |
| Acemetacin | 130.505 | 103.666 | 26.839 | 1.345697154 |
| Nimesulide | 82.485 | 17.364 | 65.121 | 3.681678623 |
| PF-431396 | 40.108 | 5.036 | 35.072 | 1.848077788 |
| Parietin | 123.156 | 97.435 | 25.721 | 1.27747639 |
| Pluripotin | 85.4 | 58.958 | 26.442 | 1.321472071 |
| Glycyl-H-1152 | 99.473 | 62.229 | 37.244 | 1.980614013 |
| Hydroxyurea | 47.712 | 5.365 | 42.347 | 2.292000916 |
| Gemcitabine | 43.326 | 10.147 | 33.179 | 1.732566244 |
| HPI-1 | 60.299 | 26.899 | 33.4 | 1.746051744 |
| ABC-294640 | 32.778 | 8.808 | 23.97 | 1.170629738 |
| PD-173955 | 35.348 | 8.871 | 26.477 | 1.323607783 |
| Cryptotanshinone | 31.687 | 5.548 | 26.139 | 1.302982901 |
| BIBR 1532 | 45.071 | 23.105 | 21.966 | 1.048344934 |
| Imiquimod | 72.849 | 50.894 | 21.955 | 1.04767371 |
| Tanshinone I | 62.314 | 23.03 | 39.284 | 2.10509555 |
| Topotecan hydrochloride | 30.703 | 8.516 | 22.187 | 1.061830434 |
| Camptothecin | 37.178 | 9.64 | 27.538 | 1.388350387 |
| 10-hydroxy-camptothecin | 33.266 | 9.333 | 23.933 | 1.168371984 |
| Irinotecan | 40.251 | 15.402 | 24.849 | 1.224266635 |
| Rebeccamycin | 41.489 | 12.004 | 29.485 | 1.50715703 |
| Doxorubicin | 61.232 | 5.625 | 55.607 | 3.101130906 |
| Pirarubicin | 26.932 | 4.326 | 22.606 | 1.087397965 |
| Etoposide | 69.938 | 10.441 | 59.497 | 3.338500112 |
| Dexrazoxane hydrochloride | 114.137 | 70.455 | 43.682 | 2.373463099 |
| Epirubicin hydrochloride | 49.805 | 4.322 | 45.483 | 2.483360769 |
| Propylthiouracil | 111.151 | 82.824 | 28.327 | 1.436495452 |
| Ansamitocin P3 | 32.337 | 5.732 | 26.605 | 1.33141839 |
| Noscapine | 38.52 | 10.875 | 27.645 | 1.394879565 |
| Paclitaxel | 55.703 | 19.451 | 36.252 | 1.920081814 |
| Colchicine | 45.702 | 9.264 | 36.438 | 1.931431602 |
| Indibulin | 48.851 | 21.582 | 27.269 | 1.371935909 |
| 4-Demethyl-epipodophyllotoxin | 78.185 | 17.735 | 60.45 | 3.396652516 |
| Vincristine sulfate | 37.863 | 9.981 | 27.882 | 1.409341391 |
| Demecolcine | 39.703 | 14.285 | 25.418 | 1.258987221 |
| Epothilone B | 49.832 | 27.108 | 22.724 | 1.094598368 |
| Docetaxel | 57.66 | 24.806 | 32.854 | 1.712734627 |
| Combretastatin A-4 | 36.125 | 12.882 | 23.243 | 1.126267935 |
| E-7010 | 44.092 | 10.419 | 33.673 | 1.762710303 |
| Epothilone A | 52.727 | 26.393 | 26.334 | 1.314881872 |
| Lexibulin hydrochloride | 46.894 | 13.896 | 32.998 | 1.721521559 |
| Cephalomannine | 45.625 | 22.158 | 23.467 | 1.139936496 |
| Ombrabulin | 38.265 | 9.585 | 28.68 | 1.458035639 |
| RO495 | 38.025 | 13.348 | 24.677 | 1.213771133 |
| Trifluridine | 57.881 | 10.459 | 47.422 | 2.60167925 |
| Raltitrexed | 59.656 | 22.166 | 37.49 | 1.995625022 |
| Vatalanib | 60.983 | 14.015 | 46.968 | 2.573976006 |
| Warfarin sodium | 121.897 | 100.275 | 21.622 | 1.027353929 |
| MK-1775 | 36.376 | 14.928 | 21.448 | 1.016736387 |
| Bendamustine | 122.856 | 25.146 | 97.71 | 5.670271176 |

TABLE 2

Compounds with decreased potency for inhibiting cell viability in CD47KO Jurkat T cells

| Name | AC50 (μM) CD47 KO | AC50 (μM) WT | Δ LogAC50 CD47KO-WT |
|---|---|---|---|
| Cladribine | 1.049 | 0.1482 | 0.85 |
| AZD-5363 | 7.4266 | 0.1663 | 1.65 |
| Akt-I-1 | 16.6261 | 2.3485 | 0.85 |
| Navitoclax | 5.8992 | 0.2348 | 1.4 |
| ABT-737 | 14.818 | 1.8655 | 0.9 |
| Obatoclax | 1.4818 | 0.3722 | 0.6 |
| I-BET151 | 20.931 | 5.8992 | 0.55 |
| Purvalanol B | 52.5764 | 14.818 | 0.55 |
| GSK-923295 | 4.6859 | 0.2635 | 1.25 |
| CHIR-124 | 1.4818 | 0.1177 | 1.1 |
| SCH-900776 | 1.4818 | 0.3722 | 0.6 |
| AEE-788 | 20.931 | 1.8655 | 1.05 |
| WZ-3146 | 13.2066 | 4.1763 | 0.5 |
| XL-647 | 11.7704 | 3.7221 | 0.5 |
| AST-1306 | 1.049 | 0.2635 | 0.6 |
| YK-4-279 | 0.935 | 0.1663 | 0.75 |
| Orantinib | 16.6261 | 1.4818 | 1.05 |
| Vargatef | 14.818 | 3.3173 | 0.65 |
| Lenvatinib | 16.6261 | 2.6351 | 0.8 |
| Trichostatin A | 0.6619 | 0.2093 | 0.5 |
| Entinostat | 2.6351 | 0.8333 | 0.5 |
| AR-42 | 0.935 | 0.2957 | 0.5 |
| Mocetinostat | 2.6351 | 0.5899 | 0.65 |
| M344 | 0.5258 | 0.1663 | 0.5 |
| 2-Methoxyestradiol | 6.619 | 0.4686 | 1.15 |
| 6-mercaptopurine | 1.6626 | 0.5258 | 0.5 |
| Alvespimycin hydrochloride | 0.6619 | 0.1663 | 0.6 |
| AVN-944 | 8.3328 | 0.3722 | 1.35 |
| NCGC00344999-01 | 2.6351 | 0.1321 | 1.3 |
| AZ-960 | 14.818 | 0.8333 | 1.25 |
| Ispinesib | 58.9917 | 0.0019 | 4.5 |
| VU0482089-2 | 5.8992 | 1.8655 | 0.5 |
| INK-128 | 4.1763 | 0.3317 | 1.1 |
| Fenbendazole | 2.0931 | 0.5899 | 0.55 |
| Ciclopirox | 14.818 | 1.049 | 1.15 |
| Oxibendazole | 0.5899 | 0.0053 | 2.05 |
| Melphalan | 23.485 | 1.4818 | 1.2 |
| Methylrosaniline chloride | 1.3207 | 0.2348 | 0.75 |
| Halofantrine | 16.6261 | 0.4686 | 1.55 |
| Cinchonidine | 20.931 | 3.3173 | 0.8 |
| Entecavir | 4.6859 | 0.3317 | 1.15 |
| Cyclocytidine HCl | 1.177 | 0.2348 | 0.7 |
| Oridonin | 7.4266 | 2.3485 | 0.5 |
| RO-4929097 | 18.6548 | 1.8655 | 1 |
| Crenolanib | 14.818 | 2.6351 | 0.75 |
| Artesunate (AS) | 14.818 | 2.3485 | 0.8 |
| CAY10626 | 6.619 | 1.049 | 0.8 |
| 3-Methyladenine | 0.5899 | 0.1321 | 0.65 |
| NVP-BGT226 | 0.5258 | 0.0662 | 0.9 |
| Volasertib | 0.3317 | 0.0662 | 0.7 |
| IVX-214 | 1.4818 | 0.4686 | 0.5 |
| Resistomycin | 4.6859 | 1.177 | 0.6 |
| Gemcitabine | 0.1865 | 0.0526 | 0.55 |

TABLE 2-continued

Compounds with decreased potency for inhibiting cell viability in CD47KO Jurkat T cells

| Name | AC50 (µM) CD47 KO | AC50 (µM) WT | Δ LogAC50 CD47KO-WT |
|---|---|---|---|
| NVP-LDE-225 | 18.6548 | 3.7221 | 0.7 |
| PD-166285 | 4.6859 | 0.5899 | 0.9 |
| AIM-100 | 16.6261 | 4.1763 | 0.6 |
| Topotecan hydrochloride | 2.0931 | 0.0418 | 1.7 |
| Camptothecin | 0.1865 | 0.0094 | 1.3 |
| 10-hydroxy-camptothecin | 0.3317 | 0.0209 | 1.2 |
| SN-38 | 0.2957 | 0.0037 | 1.9 |
| Irinotecan | 1.8655 | 0.3317 | 0.75 |
| Rebeccamycin | 0.7427 | 0.1482 | 0.7 |
| Mitoxantrone | 1.8655 | 0.1663 | 1.05 |
| Idarubicin hydrochloride | 0.6619 | 0.1482 | 0.65 |
| Pirarubicin | 13.2066 | 1.4818 | 0.95 |
| Epirubicin hydrochloride | 1.049 | 0.2635 | 0.6 |
| Vosaroxin | 12.8702 | 1.1471 | 1.05 |
| Teniposide | 4.1763 | 0.1663 | 1.4 |
| APR-246 | 16.6261 | 1.4818 | 1.05 |
| Vinorelbine | 0.0209 | 0.0066 | 0.5 |
| Plinabulin | 2.148 | 0.1914 | 1.05 |
| Bayer-18 | 16.6261 | 2.6351 | 0.8 |

Figure 14B:
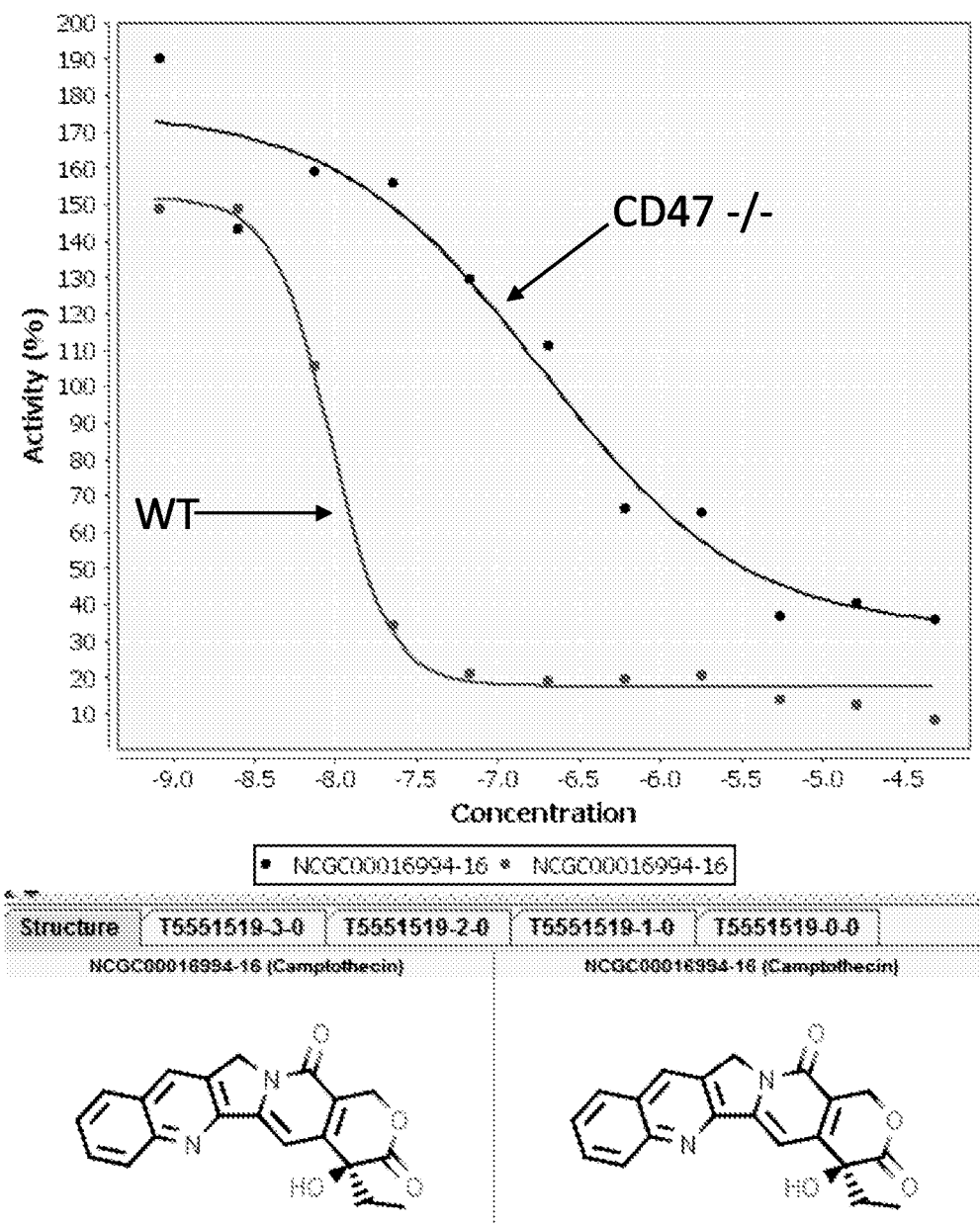
Figure 14D:
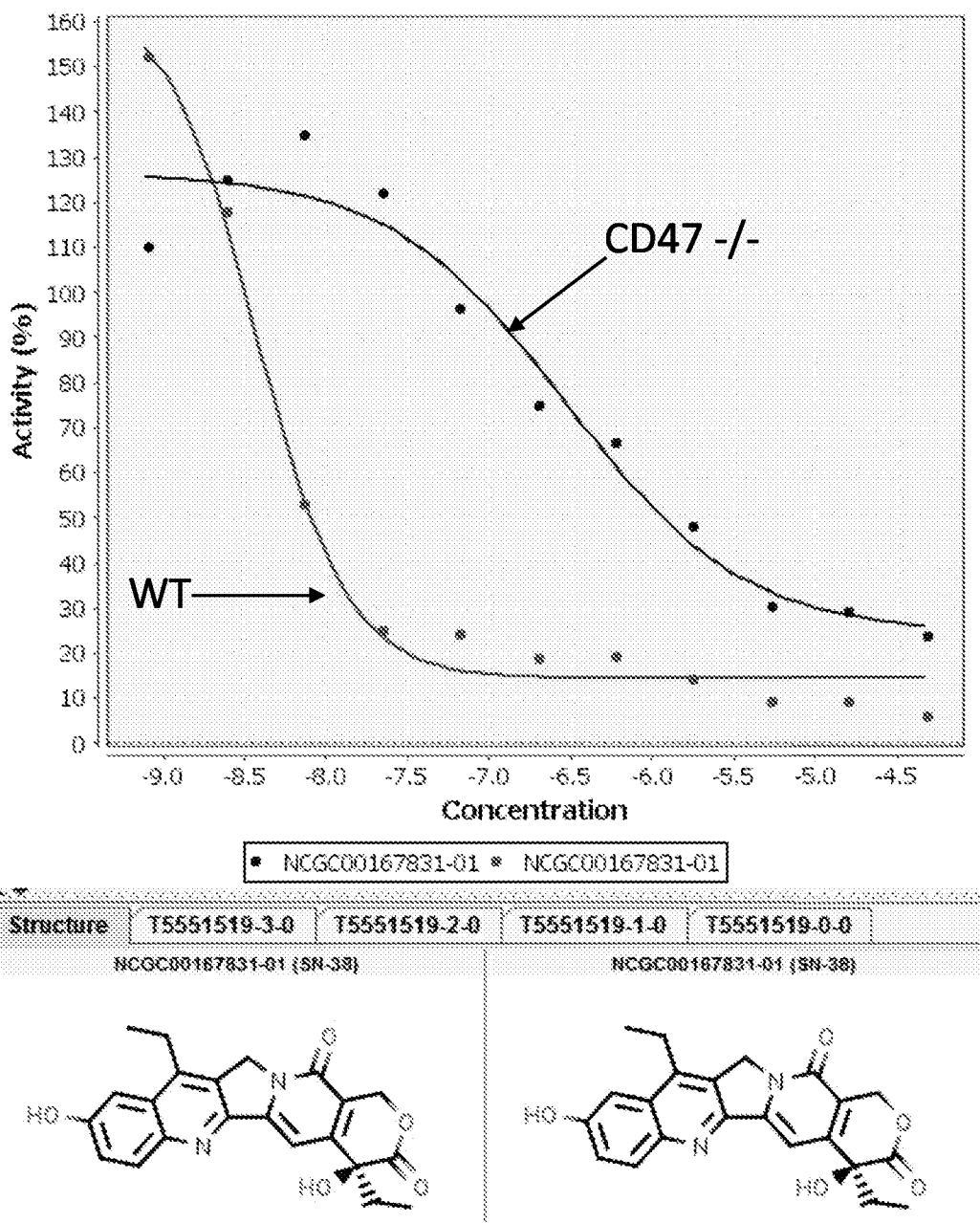
Figure 14F:
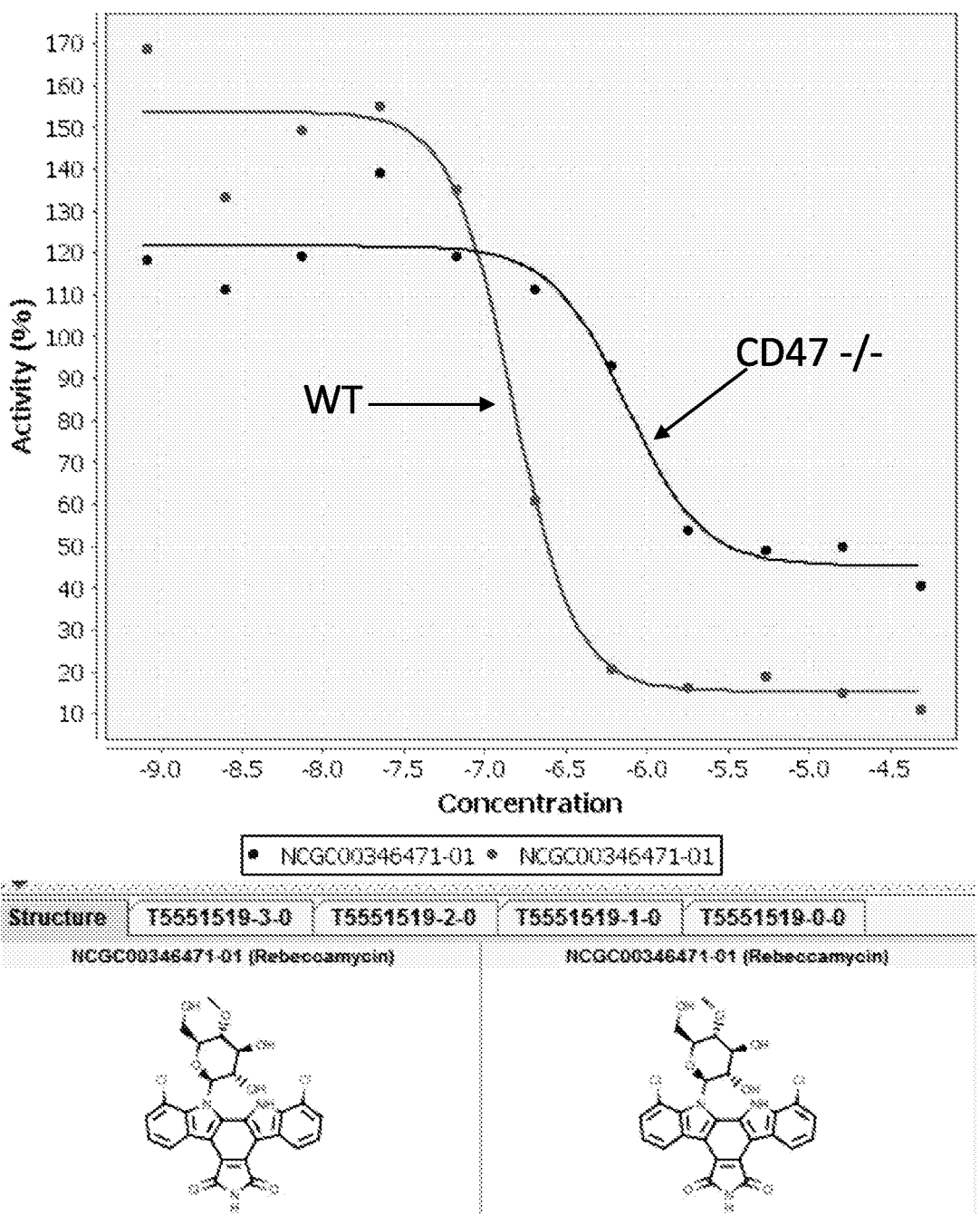
Figure 15B:
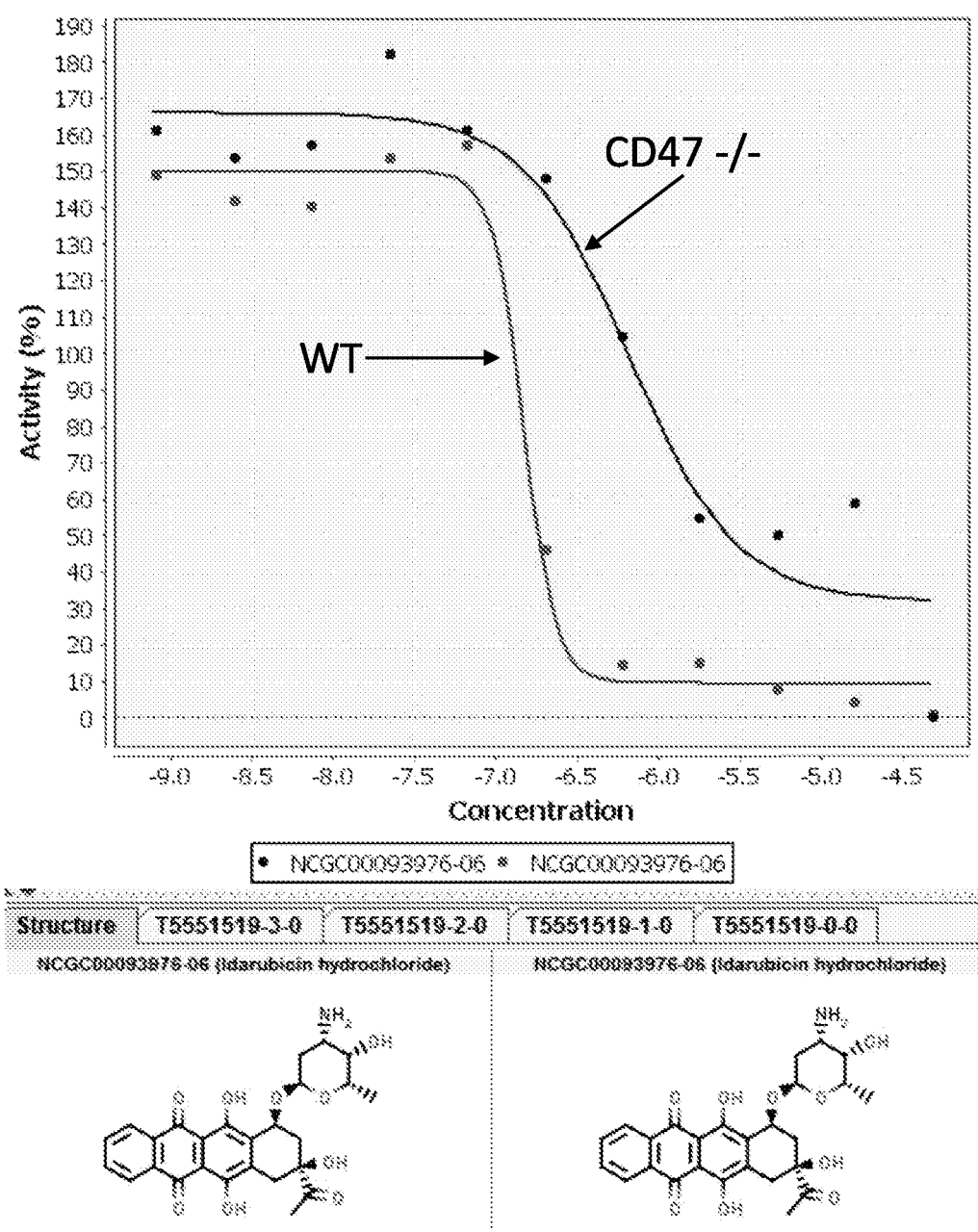
Figure 15C:
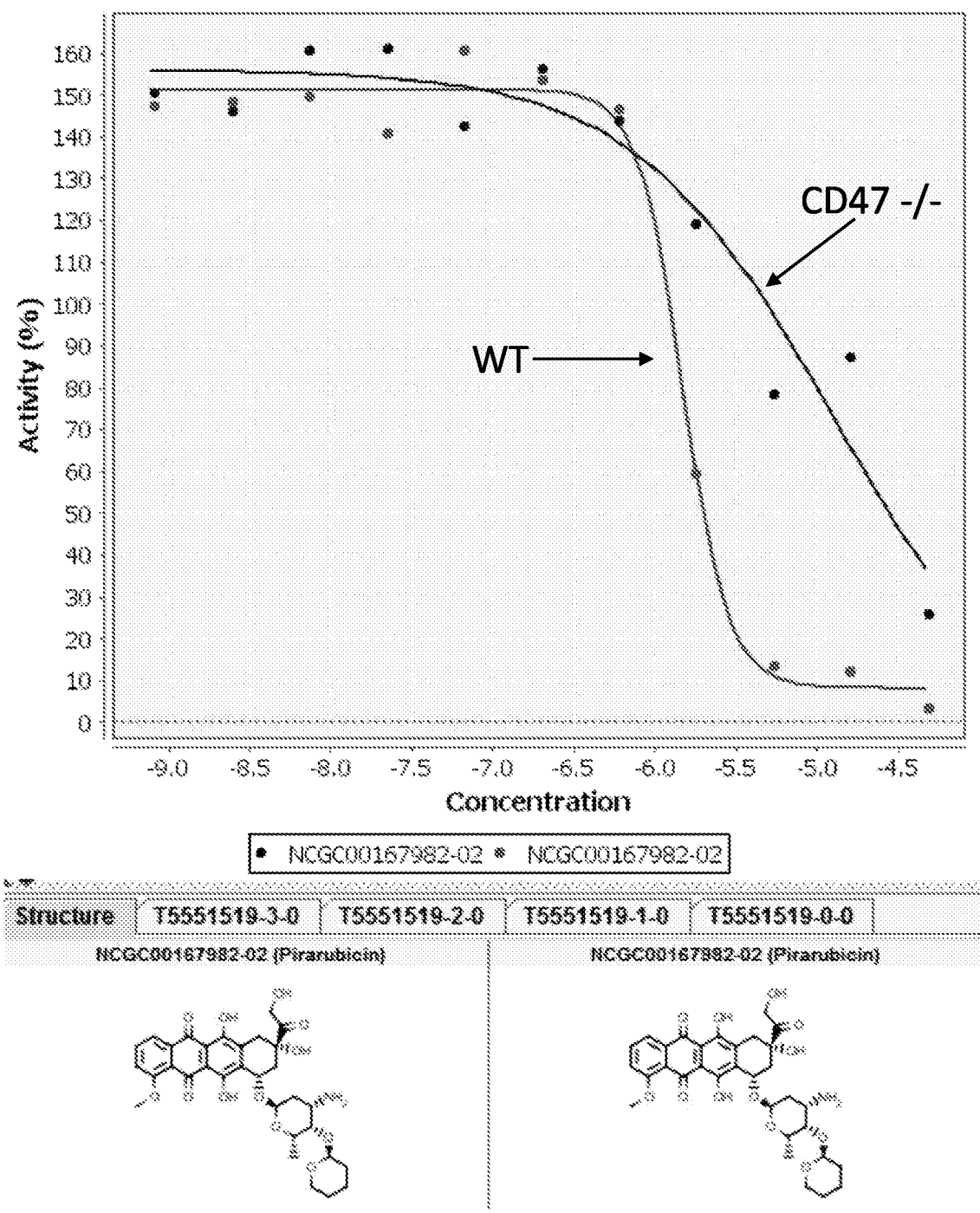
Figure 15D:
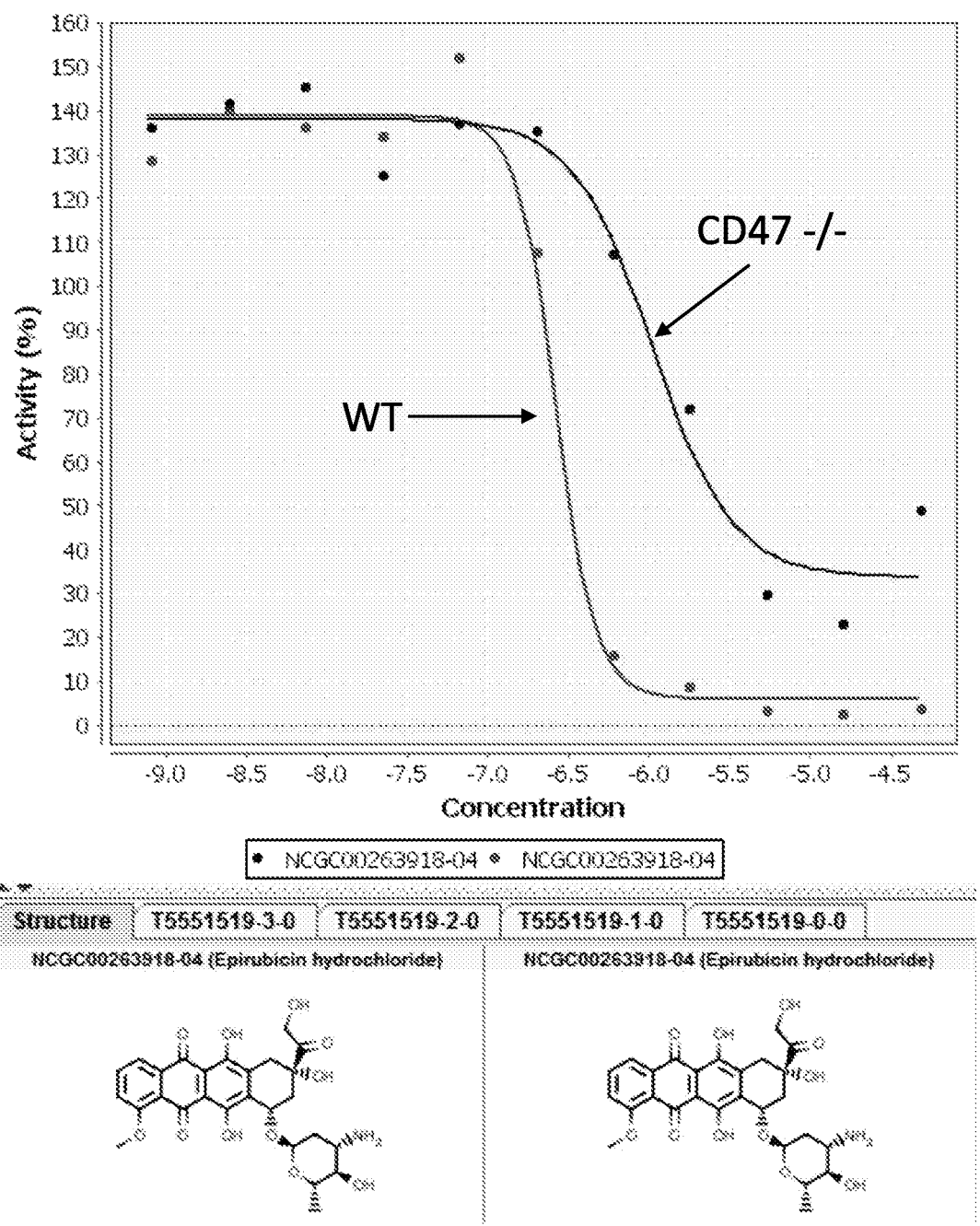

Deficiency of CD47 protected cells from increasing concentrations of anthracycline family members, including mitoxantrone, idarubicin, pirarubicin, and epirubicin (FIG. 14A-D) and the quinolone vosaroxin (FIG. 14E), which targets topoisomerase-II, as do other anthracyclines. This study also confirmed the protective effect of CD47 blockade for doxorubicin cytotoxicity in non-tumor cells (FIG. 14F). Cells deficient in CD47 were also protected from cytotoxicity of topoisomerase-I inhibitors of the camptothecin family, including topotecan, camptothecin, 10-hydroxycamptothecin, SN-38, irinotecan, and rebeccamycin (FIG. 15A-F).

In addition to CD47-dependent sensitivity to the pyrimidine synthesis inhibitor 5-fluororouracil (Example 2), CD47-deficient Jurkat T cells exhibited significantly decreased maximal inhibition of viability when treated with the nucleotide biosynthesis inhibitors cladribine, fludarabine, cytarabine, and gemcitabine (Table 1). A significant decrease in inhibitory potency as assessed by the calculated 50% inhibitory dose (AC50) was also observed for cladribine, 6-mercaptopurine, and gemcitabine (Table 2). This activity also extended to additional metabolic DNA synthesis inhibitors including entecavir and rifapentine (Tables 1 and 2). Furthermore, CD47-expressing and deficient Jurkat T cells exhibited differing sensitivities to the *vinca* alkaloid analog vinorelbine, nitrogen mustards that alkylate and cross link DNA including chlorambucil and bendamustine, the DNA alkylating agent ThioTEPA, the platinum compound oxaliplatin that cross links purine bases in DNA, and the well-characterized DNA strand break-inducing drug bleomycin sulfate (Tables 1 and 2). Therefore, therapeutic suppression of CD47 confers protection of nonmalignant cells against a wide range of DNA damaging chemotherapeutic drugs. The selectivity of cytoprotection by CD47 blockade is indicated by the large number of drugs tested in this screen that exhibited no significant differences in cytotoxicity for wild type versus CD47-deficient Jurkat T cells. Some classes of targeted therapeutics, such as mTOR inhibitors, generally showed significantly increased potency in cells lacking CD47, indicating that combining CD47 blockade with at least some members of this class of therapeutics may not be beneficial.

In view of the many possible embodiments to which the principles of the disclosure may be applied, it should be recognized that the illustrated embodiments are only examples and should not be taken as limiting the scope of the invention. Rather, the scope of the invention is defined by the following claims. We therefore claim as our invention all that comes within the scope and spirit of these claims.

We claim:

1. A method of reducing cytotoxicity of an anthracycline, a topoisomerase inhibitor, or a nucleotide synthesis inhibitor to non-cancer cells in a subject in need thereof, comprising administering to the subject an effective amount of:
   an antisense CD47 morpholino oligonucleotide; and
   the anthracycline, the topoisomerase inhibitor, or the nucleotide synthesis inhibitor,
   wherein the antisense CD47 morpholino oligonucleotide is administered to the subject before, during, or after administration of the anthracycline, the topoisomerase inhibitor, or the nucleotide synthesis inhibitor.

2. The method of claim 1, wherein the anthracycline is doxorubicin, daunorubicin, epirubicin, idarubicin, or valrubicin.

3. The method of claim 1, wherein the nucleotide synthesis inhibitor is cladribine, clofarabine, fludarabine, mercaptopurine, thioguanine, pentostatin, capecitabine, cytarabine, 5-fluorouracil, floxuridine, or gemcitabine.

4. The method of claim 1, wherein the topoisomerase inhibitor is camptothecin, topotecan, irinotecan, or etoposide.

5. The method of claim 1, wherein the antisense CD47 morpholino oligonucleotide comprises the nucleic acid sequence CGTCACAGGCAGGACCCACTGCCCA (SEQ ID NO: 3).

6. The method of claim 1, wherein the subject has breast cancer, lung cancer, ovarian cancer, prostate cancer, thyroid cancer, bladder cancer, stomach cancer, multiple myeloma, soft tissue sarcoma, leukemia, or lymphoma.

7. The method of claim 1, wherein the cytotoxicity of the anthracycline, the topoisomerase inhibitor, or the nucleotide synthesis inhibitor to non-cancer cells is cardiotoxicity, nephrotoxicity, hepatotoxicity, myelosuppression, alopecia, gastrointestinal distress, or peripheral neuropathy.

8. The method of claim 1, wherein the antisense CD47 morpholino oligonucleotide is administered to the subject prior to administration of the anthracycline, the topoisomerase inhibitor, or the nucleotide synthesis inhibitor.

9. The method of claim 8, wherein the antisense CD47 morpholino oligonucleotide is administered to the subject at least about 24 hours prior to administration of the anthracycline, the topoisomerase inhibitor, or the nucleotide synthesis inhibitor or at least about 48 hours prior to the administration of the anthracycline, the topoisomerase inhibitor, or the nucleotide synthesis inhibitor.

10. The method of claim 1, further comprising detecting cytotoxicity to non-cancer cells in the subject by detecting a reduction or inhibition of cardiotoxicity in the subject compared to a control.

11. The method of claim 1, further comprising selecting a subject who is at risk for cytotoxicity of the anthracycline, the topoisomerase inhibitor, or the nucleotide synthesis inhibitor to non-cancer cells for administration of the antisense CD47 morpholino oligonucleotide and the anthracycline, the topoisomerase inhibitor, or the nucleotide synthesis inhibitor, wherein the subject has pre-existing heart disease, hypertension, previous mediastinal irradiation, female gender, and/or age less than 4 years, or the subject has received a cumulative dose of greater than 400 mg/m$^2$ and/or administration of an anthracycline at more than 50 mg/m$^2$ dose per day.

12. A method of reducing cytotoxicity of an anthracycline, a topoisomerase inhibitor, or a nucleotide synthesis inhibitor to non-cancer cells in a subject in need thereof, comprising:
   (a) administering an antisense CD47 morpholino oligonucleotide to the subject;
   (b) administering the anthracycline, the topoisomerase inhibitor, or the nucleotide synthesis inhibitor to the subject, wherein (a) and (b) can be performed in either order or concurrently; and
   (c) detecting a reduction of cytotoxicity to non-cancer cells in the subject by detecting a reduction or inhibition of cardiotoxicity, nephrotoxicity, hepatotoxicity, myelosuppression, alopecia, gastrointestinal distress, or peripheral neuropathy in the subject compared to a control.

13. The method of claim 12, further comprising selecting a subject who is at risk for cytotoxicity of the DNA damaging agent to non-cancer cells for administration of the antisense CD47 morpholino oligonucleotide and the anthracycline, the topoisomerase inhibitor, or the nucleotide synthesis inhibitor, wherein the subject has pre-existing heart disease, hypertension, previous mediastinal irradiation, female gender, and/or age less than 4 years, or the subject has received a cumulative dose of greater than 400 mg/m$^2$ and/or administration of an anthracycline at more than 50 mg/m$^2$ dose per day.

* * * * *

SEQUENCE LISTING

```
<160> NUMBER OF SEQ ID NOS: 3

<210> SEQ ID NO 1
<211> LENGTH: 11
<212> TYPE: PRT
<213> ORGANISM: Artificial Sequence
<220> FEATURE:
<223> OTHER INFORMATION: Thrombospondin 1-derived CD47 binding peptide

<400> SEQUENCE: 1

Phe Ile Arg Val Val Met Tyr Glu Gly Lys Lys
1               5                   10

<210> SEQ ID NO 2
<211> LENGTH: 8
<212> TYPE: PRT
<213> ORGANISM: Artificial Sequence
<220> FEATURE:
<223> OTHER INFORMATION: CD47 binding peptide

<400> SEQUENCE: 2

Arg Phe Tyr Val Val Met Trp Lys
1               5

<210> SEQ ID NO 3
<211> LENGTH: 25
<212> TYPE: DNA
<213> ORGANISM: Artificial Sequence
```

```
<220> FEATURE:
<223> OTHER INFORMATION: CD47 antisense morpholino oligonucleotide

<400> SEQUENCE: 3
cgtcacaggc aggacccact gccca                                            25
```